(12) United States Patent
Chen et al.

(10) Patent No.: US 9,744,347 B2
(45) Date of Patent: Aug. 29, 2017

(54) SYSTEMS AND METHODS FOR REDUCING POWER CONSUMPTION IN AN IMPLANTABLE MEDICAL DEVICE

(71) Applicant: Greatbatch Ltd., Clarence, NY (US)

(72) Inventors: Joey Chen, Valencia, CA (US); Kerry Bradley, Glendale, CA (US); Leslie Halberg, Valencia, CA (US)

(73) Assignee: GREATBATCH, LTD., Clarence, NY (US)

( * ) Notice: Subject to any disclaimer, the term of this patent is extended or adjusted under 35 U.S.C. 154(b) by 346 days.

(21) Appl. No.: 14/321,234

(22) Filed: Jul. 1, 2014

(65) Prior Publication Data

US 2015/0012062 A1 Jan. 8, 2015

Related U.S. Application Data

(60) Provisional application No. 61/841,965, filed on Jul. 2, 2013.

(51) Int. Cl.
*A61N 1/372* (2006.01)
*A61N 1/05* (2006.01)
(Continued)

(52) U.S. Cl.
CPC ............ *A61N 1/0551* (2013.01); *A61B 5/064* (2013.01); *A61B 8/0841* (2013.01); *A61N 1/05* (2013.01);
(Continued)

(58) Field of Classification Search
CPC ............ A61N 1/37252; A61N 1/37223; A61N 1/36153; A61N 1/37276; A61N 1/3727; A61N 1/37282
(Continued)

(56) References Cited

U.S. PATENT DOCUMENTS 5,127,404 A * 7/1992 Wyborny ............. A61N 1/3708
128/903
5,284,154 A 2/1994 Raymond et al.
(Continued)

FOREIGN PATENT DOCUMENTS

CN 101325985 12/2008
FR 2339894 8/1977
(Continued)

OTHER PUBLICATIONS

Gordon M. Greenblatt, M.D. et al. "Needle Nerve Stimulator-Locator: Nerve Blocks with a New Instrument for Locating Nerves" Anesthesia and Analgesia, vol. 41, No. 5, Sep.-Oct. 1962, pp. 599-602.
(Continued)

*Primary Examiner* — Alyssa M Alter
(74) *Attorney, Agent, or Firm* — Haynes and Boone, LLP; Eric Li

(57) ABSTRACT

A medical device for providing a stimulation therapy includes stimulation circuitry configured to provide a plurality of electrical pulses to be delivered to a patient. The stimulation circuitry contains a microcontroller configured to generate the electrical pulses. Each electrical pulse includes a primary phase, an interphase after the primary phase, and a recovery phase after the primary phase. Consecutive electrical pulses are separated by a standby period. The microcontroller is configured to operate in an active mode during at least one of: the primary phase and the interphase. The microcontroller is configured to operate in a power-conservation mode during a substantial majority of the standby period. The microcontroller consumes substantially less power when operating in the power-conservation mode than in the active mode.

20 Claims, 37 Drawing Sheets

(51) Int. Cl.
*A61B 5/06* (2006.01)
*A61B 8/08* (2006.01)
*A61N 1/36* (2006.01)
*A61N 1/378* (2006.01)
*A61N 1/375* (2006.01)

(52) U.S. Cl.
CPC ....... *A61N 1/0553* (2013.01); *A61N 1/36017* (2013.01); *A61N 1/36021* (2013.01); *A61N 1/36071* (2013.01); *A61N 1/36125* (2013.01); *A61N 1/36139* (2013.01); *A61N 1/36146* (2013.01); *A61N 1/36153* (2013.01); *A61N 1/3752* (2013.01); *A61N 1/3787* (2013.01); *A61N 1/37223* (2013.01); *A61N 1/37235* (2013.01); *A61N 1/37252* (2013.01)

(58) Field of Classification Search
USPC .......................................................... 607/59
See application file for complete search history.

(56) References Cited

U.S. PATENT DOCUMENTS

| | | | |
|---|---|---|---|
| 5,417,719 | A | 5/1995 | Hull et al. |
| 5,702,429 | A | 12/1997 | King |
| 5,775,331 | A | 7/1998 | Raymond et al. |
| 5,941,906 | A | 8/1999 | Barreras, Sr. et al. |
| 6,236,892 | B1 | 5/2001 | Feler |
| 6,366,814 | B1 | 4/2002 | Boveja et al. |
| 6,687,538 | B1 | 2/2004 | Hrdlicka et al. |
| 6,725,096 | B2 | 4/2004 | Chinn et al. |
| 7,009,313 | B1 | 3/2006 | Parramon et al. |
| 7,104,965 | B1 | 9/2006 | Jiang et al. |
| 7,174,215 | B2 | 2/2007 | Bradley |
| 7,221,981 | B2 | 5/2007 | Gliner |
| 7,444,184 | B2 | 10/2008 | Boveja et al. |
| 7,450,992 | B1 | 11/2008 | Cameron |
| 7,680,540 | B2 | 3/2010 | Jensen et al. |
| 7,697,985 | B2 | 4/2010 | Kaiser et al. |
| 7,697,995 | B2 | 4/2010 | Cross, Jr. et al. |
| 7,751,884 | B2 | 7/2010 | Ternes et al. |
| 7,801,615 | B2 | 9/2010 | Meadows et al. |
| 7,806,862 | B2 | 10/2010 | Molnar |
| 8,195,304 | B2 | 6/2012 | Strother et al. |
| 8,233,984 | B2 | 7/2012 | Forsberg et al. |
| 8,335,569 | B2 | 12/2012 | Aghassian |
| 8,380,314 | B2 | 2/2013 | Panken et al. |
| 8,457,756 | B2 | 6/2013 | Rahman |
| 8,504,160 | B2 | 8/2013 | Lee et al. |
| 8,538,548 | B2 | 9/2013 | Shi et al. |
| 8,588,927 | B2 | 11/2013 | Roy et al. |
| 8,600,505 | B2 | 12/2013 | Libbus et al. |
| 8,606,362 | B2 | 12/2013 | He et al. |
| 8,612,002 | B2 | 12/2013 | Faltys et al. |
| 8,628,475 | B2 | 1/2014 | Wang |
| 8,634,893 | B2 | 1/2014 | Skubitz et al. |
| 8,634,927 | B2 | 1/2014 | Olson et al. |
| 8,644,947 | B2 | 2/2014 | Zhu et al. |
| 8,700,178 | B2 | 4/2014 | Anderson |
| 2002/0133204 | A1* | 9/2002 | Hrdlicka .................. A61N 1/08 607/11 |
| 2006/0184209 | A1* | 8/2006 | John .................... A61N 1/0531 607/45 |
| 2006/0195159 | A1 | 8/2006 | Bradley et al. |
| 2006/0253182 | A1 | 11/2006 | King |
| 2007/0293910 | A1* | 12/2007 | Strother ............. A61N 1/37276 607/48 |
| 2008/0103559 | A1 | 5/2008 | Thacker et al. |
| 2009/0312817 | A1 | 12/2009 | Hogle et al. |
| 2010/0198308 | A1 | 8/2010 | Zhou et al. |
| 2011/0208265 | A1 | 8/2011 | Erickson et al. |
| 2012/0004709 | A1 | 1/2012 | Chen et al. |
| 2012/0123502 | A1 | 5/2012 | Aghassian et al. |
| 2012/0239108 | A1 | 9/2012 | Foutz et al. |
| 2013/0079635 | A1 | 3/2013 | Patrick et al. |
| 2013/0110201 | A1 | 5/2013 | Bonde et al. |
| 2013/0245715 | A1 | 9/2013 | Peterson |
| 2013/0310897 | A1 | 11/2013 | Marnfeldt et al. |
| 2013/0310909 | A1 | 11/2013 | Simon et al. |
| 2013/0338732 | A1 | 12/2013 | Foutz et al. |
| 2014/0039578 | A1 | 2/2014 | Whitehurst et al. |
| 2014/0046407 | A1 | 2/2014 | Ben-Ezra et al. |
| 2014/0046423 | A1 | 2/2014 | Rajguru et al. |
| 2014/0058189 | A1 | 2/2014 | Stubbeman |
| 2014/0058495 | A1 | 2/2014 | Sakai et al. |
| 2014/0073926 | A1 | 3/2014 | Rajendran et al. |
| 2014/0136585 | A1 | 5/2014 | Brockway |

FOREIGN PATENT DOCUMENTS

| | | |
|---|---|---|
| WO | WO 93/25271 | 12/1993 |
| WO | WO 02/09808 | 2/2002 |
| WO | WO 2013/165628 | 11/2013 |
| WO | WO 2014/036184 | 3/2014 |

OTHER PUBLICATIONS

Stephen A. Raymond, Ph.D. et al. "The NerveSeeker: A System for Automated Nerve Localization" Regional Anesthesia & Pain Medicine, May/Jun. 1992, 1 page Abstract.

* cited by examiner

| Fig. 8A | Fig. 8B | Fig. 8C | Fig. 8D | Fig. 8E | Fig. 8F |
|---|---|---|---|---|---|
| Fig. 8G | Fig. 8H | Fig. 8I | Fig. 8J | Fig. 8K | Fig. 8L |

Fig. 8

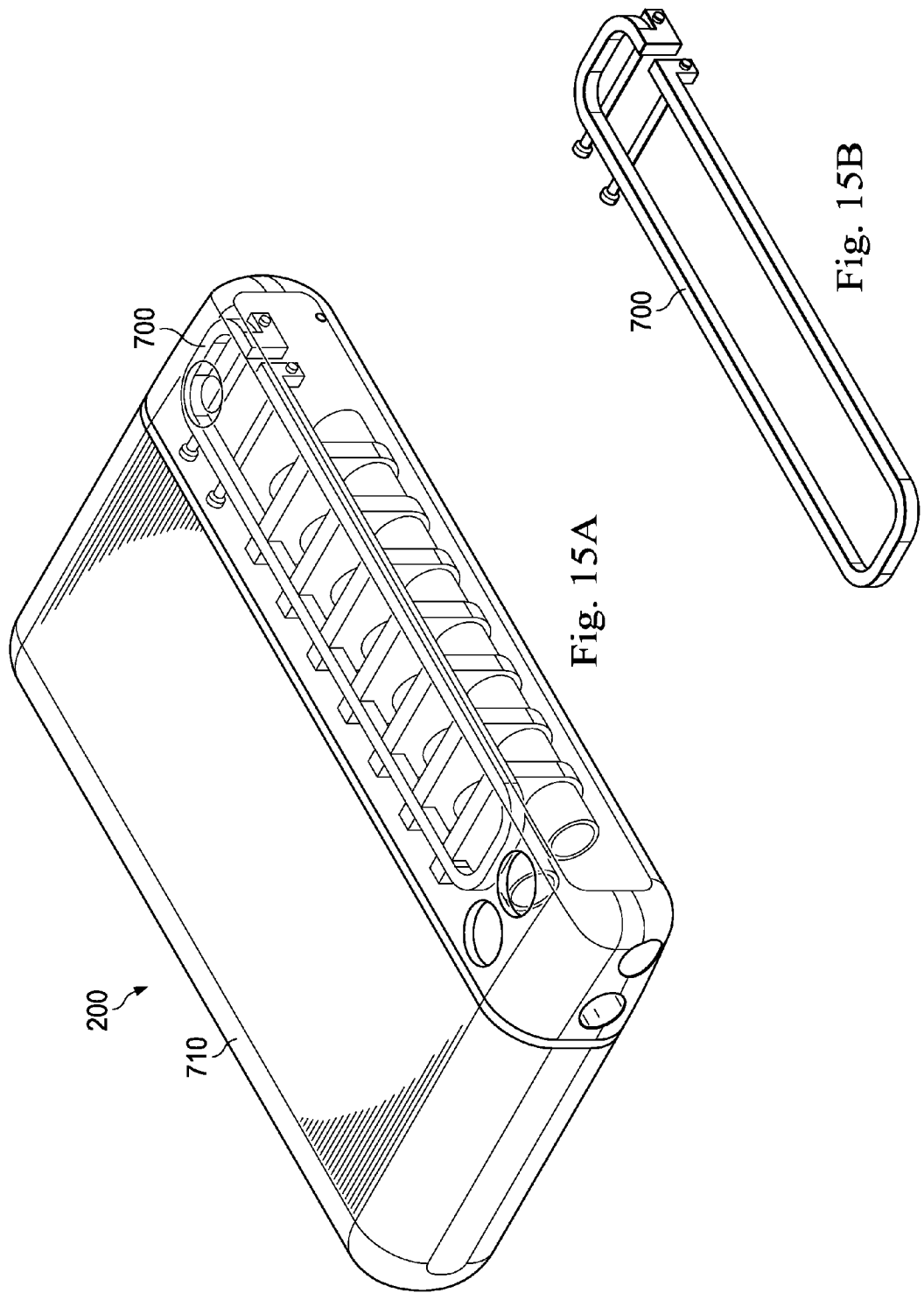

SYSTEMS AND METHODS FOR REDUCING POWER CONSUMPTION IN AN IMPLANTABLE MEDICAL DEVICE

PRIORITY DATA

The present application is a utility application of provisional U.S. Patent Application No. 61/841,965, filed on Jul. 2, 2013, entitled "Stimulation Apparatuses, Devices, Systems, and Methods," the disclosure of which is hereby incorporated by reference in its entirety.

FIELD

Various embodiments described herein relate to the field of implantable medical devices, and methods of communicating therewith.

BACKGROUND

As medical device technologies continue to evolve, neurostimulator devices have gained much popularity in the medical field. Neurostimulator devices are typically battery-powered devices that are designed to deliver electrical stimulation to a patient. Through proper electrical stimulation, the neurostimulator devices can provide pain relief for patients. In effect, the electrical signals sent by the neurostimulator devices "mask" or modify the pain signals before the pain signals reach the patient's brain. As a result, the patient may feel only a tingling sensation (known as "Paresthesia) in the area that is stimulated instead of pain. For example, peripheral nerve stimulation has been used to treat chronic pain emanating from a patient's extremity, such as in the patient's arm and/or leg. A typical peripheral neurostimulator (PNS) device may include one or more integrated circuit chips containing the control circuitry and neurostimulation circuitry. The PNS device may also include a plurality of electrodes that are in contact with different areas of a patient's body. The PNS device typically includes a battery, either permanent or rechargeable, that is utilized to power the stimulation circuitry and the external communications. Controlled by the control circuitry within the neurostimulator, the electrodes are each capable of delivering electrical stimulation to their respective target contact areas. Thus, the patient can use the PNS device to stimulate areas in a localized manner.

In spite of recent advances, conventional PNS devices still have various shortcomings. As an example, the nerves in a spinal cord are typically arranged more orderly and run along a linear path, whereas the nerves to be stimulated in peripheral nerve stimulation usually wind tortuously along a neurovascular bundle. Therefore, a typical paddle lead for a conventional PNS device or for spinal cord stimulation does not offer the flexibility and versatility needed to stimulate the target nerve fibers for peripheral nerve stimulation, as they are not configured to allow electrical stimulation energy to follow the tortuous peripheral nerve targets selectively. As another example, conventional PNS devices typically require an antenna to receive telemetry signals and a separate charging coil to receive charging signals. As a result, PNS design is more complex and more expensive. As yet another example, conventional PNS devices typically do not employ sophisticated power maximization techniques to reduce power consumption. Consequently, conventional PNS devices tend to have battery life that does not last as long as desired. The short battery life may lead to user dissatisfaction. As yet another example, it may be difficult to determine a target nerve site for applying stimulation.

As a result, although existing systems and methods of peripheral neurostimulation have been generally adequate for their intended purposes, they have not been entirely satisfactory in every aspect.

SUMMARY

One aspect of the present disclosure involves an implantable lead configured to deliver an electrical stimulation therapy for a patient. The lead includes an elongate lead body that is configured to be coupled to a pulse generator that generates electrical stimulations pulses as part of the electrical stimulation therapy. The lead also includes a paddle coupled to the lead body. The paddle contains a plurality of electrodes that are each configured to deliver the electrical stimulation pulses to the patient. The plurality of electrodes is arranged into at least three columns that each include a respective subset of the electrodes. The plurality of electrodes each includes a unique centerline, wherein the centerlines extend in directions transverse to the columns.

Another aspect of the present disclosure involves an implantable lead configured to deliver an electrical stimulation therapy for a patient. The lead includes an elongate lead body that is configured to be coupled to a pulse generator that generates electrical stimulations pulses as part of the electrical stimulation therapy. The lead also includes a paddle coupled to the lead body. The paddle contains a plurality of electrodes that are each configured to deliver the electrical stimulation pulses to the patient. The plurality of electrodes each have a respective first centerline extending along a first direction and a respective centerline extending along a second direction different from the first axis. A substantial majority of the first centerlines are not aligned in the first direction with any of the other first centerlines. A substantial majority of the second centerlines are not aligned in the second direction with any of the other second centerlines.

Yet another aspect of the present disclosure involves an implantable lead configured to deliver an electrical stimulation therapy for a patient. The lead includes an elongate lead body that is configured to be coupled to a pulse generator that generates electrical stimulations pulses as part of the electrical stimulation therapy. The lead also includes a paddle coupled to the lead body. The paddle contains a plurality of electrodes that are each configured to deliver the electrical stimulation pulses to the patient. The electrodes collective define a stimulation region on the paddle. A substantial majority of linear paths across the stimulation region intersect with at least one of the electrodes.

Another aspect of the present disclosure involves a medical device for providing an electrical stimulation therapy for a patient. The medical device includes a coil configured to receive both inductive charging signals and telemetry signals. The inductive charging signals are in a first frequency band. The telemetry signals are in a second frequency band that is substantially higher than the first frequency band. The medical device includes inductive charging circuitry configured to provide electrical power to the medical device via the inductive charging signals. The medical device includes telemetry circuitry configured to conduct telecommunications with external device via the telemetry signals. The medical device includes a first component that is electrically coupled between the coil and the inductive charging circuitry. The first component is configured to allow the inductive charging signals to pass through. The medical device includes a second component that is electrically coupled between the coil and the telemetry circuitry. The second component is configured to substantially block the inductive charging signals while allowing the telemetry signals to pass through.

Another aspect of the present disclosure involves a medical system for providing an electrical stimulation therapy for a patient. The medical system includes an electronic programmer configured to generate first telemetry signals that contain stimulation programming instructions for an implantable pulse generator (IPG) and second telemetry signals for waking up the IPG. The medical system includes the IPG configured to generate electrical pulses in response to the stimulation programming instructions. The IPG contains an antenna configured to receive the first telemetry signals, the second telemetry signals, and inductive charging signals. The inductive charging signals are in a first frequency band, the first telemetry signals are in a second frequency band that is substantially higher than the first frequency band, and the second telemetry signals are in a third frequency band that is substantially higher than the second frequency band. The IPG contains an inductive charging circuitry configured to provide electrical power to the medical device via the inductive charging signals. The IPG contains telemetry circuitry configured to conduct telecommunications with external device via the telemetry signals. The IPG contains a first circuit that is electrically coupled between the antenna and the inductive charging circuitry. The first circuit contains one or more electronic components that create a resonant frequency centered around the first frequency band. The IPG contains a second circuit that is electrically coupled between the antenna and the telemetry circuitry. The second circuit is configured to substantially reject the inductive charging signals and the second telemetry signals while allowing the first telemetry signals to pass through. The IPG contains a third circuit that is electrically coupled between the antenna and the telemetry circuitry and in parallel with the second circuit. The third circuit is configured to reject the inductive charging signals and the first telemetry signals while allowing the second telemetry signals to pass through.

Another aspect of the present disclosure involves a method of providing discrimination for a plurality of types of input signals received from a single antenna. The method includes receiving, via the single antenna, inductive charging signals and first telemetry signals. The inductive charging signals are in a first frequency band, the first telemetry signals are in a second frequency band that is substantially higher than the first frequency band. The method includes generating, via a first circuit coupled to the single antenna, a resonant frequency substantially near the first frequency band such that the first circuit allows the inductive charging signals to pass through while attenuating the first telemetry signals. The method includes rejecting, via a second circuit coupled to the single antenna, the inductive charging signals while allowing the first telemetry signals to pass through.

Another aspect of the present disclosure involves a medical device for providing an electrical stimulation therapy for a patient. The medical device includes telemetry circuitry configured to receive programming instructions via telecommunications conducted with an electronic programmer. The medical device includes stimulation circuitry configured to provide, in response to the received programming instructions, a plurality of electrical pulses to be delivered to the patient as a part of the electrical stimulation therapy. The stimulation circuitry contains a microcontroller configured to generate the electrical pulses. Each electrical pulse includes a primary phase, an interphase after the primary phase, and a recovery phase after the primary phase. Consecutive electrical pulses are separated by a standby period. The medical device includes power supply circuitry configured to provide electrical power to the telemetry circuitry and the stimulation circuitry. The microcontroller is configured to operate in an active mode during at least one of: the primary phase and the interphase, and the microcontroller is configured to operate in a power-conservation mode during a substantial majority of the standby period. The microcontroller consumes substantially less power when operating in the power-conservation mode than in the active mode.

Another aspect of the present disclosure involves a medical system for providing an electrical stimulation therapy for a patient. The medical system includes an electronic programmer configured to generate stimulation programming instructions for an implantable pulse generator (IPG). The medical system includes the IPG. The IPG comprises telemetry circuitry configured to receive the programming instructions via telecommunications conducted with the electronic programmer. The IPG comprises stimulation circuitry configured to provide, in response to the received programming instructions, a plurality of electrical pulses to be delivered to the patient as a part of the electrical stimulation therapy. The stimulation circuitry contains a microcontroller configured to generate the electrical pulse. Each electrical pulse includes a primary phase, an interphase after the primary phase, and a recovery phase after the primary phase. Consecutive electrical pulses are separated by a standby period. The IPG comprises power supply circuitry configured to provide electrical power to the telemetry circuitry and the stimulation circuitry. The microcontroller is configured to operate in an active mode during at least one of: the primary phase and the interphase, and the microcontroller is configured to operate in a power-conservation mode during a substantial majority of the standby period. The microcontroller consumes substantially less power when operating in the power-conservation mode than in the active mode.

Another aspect of the present disclosure involves a method of providing an electrical stimulation therapy for a patient. The method includes receiving programming instructions from an electronic programmer. The method includes generating, via a microcontroller and in response to the received programming instructions, a plurality of electrical pulses to be delivered to the patient as a part of the electrical stimulation therapy. Each electrical pulse includes a primary phase, an interphase after the primary phase, and a recovery phase after the primary phase. Consecutive electrical pulses are separated by a standby period. The generating of the electrical pulses comprises: operating the microcontroller in an active mode during at least one of: the primary phase and the interphase, and operating the microcontroller in a power-conservation mode during a substantial majority of the standby period. The microcontroller consumes substantially less power when operating in the power-conservation mode than in the active mode.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 8 is a legend showing how the FIGS. 8A-8L are arranged together.

FIGS. 15A-15C illustrate a conductive element used by a peripheral neurostimulator according to various embodiments of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn to different scales for simplicity and clarity.

Figure 1:
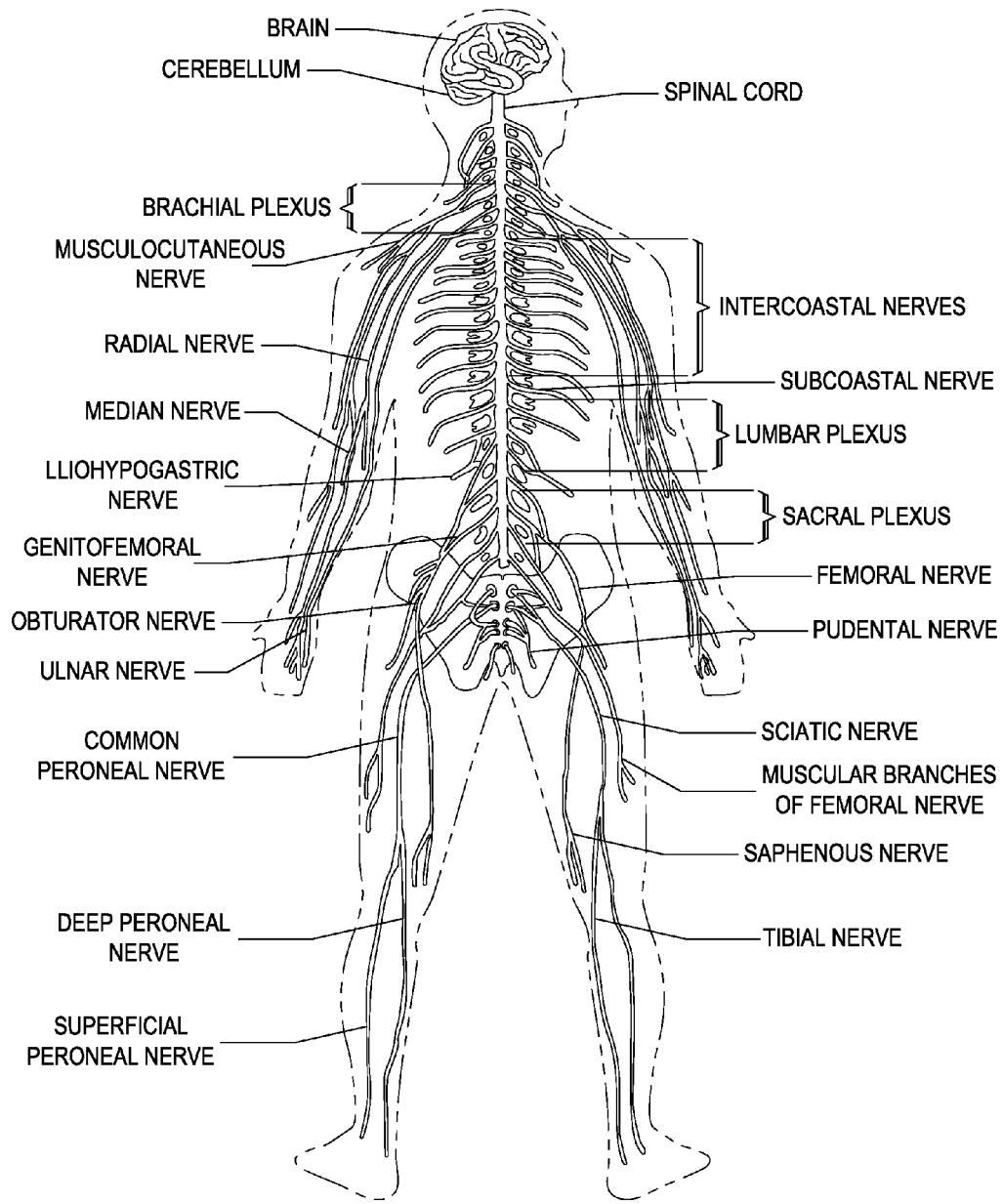
FIG. 1 is stylized overview of the human nervous system.

The human nervous system includes a complex network of neurological structures that extend throughout the body. As shown in FIG. 1, the brain interconnects with the spinal cord which branches into the brachial plexus near the shoulders and the lumbar plexus and sacral plexus in the lower back. The limb peripheral nerves of the arms extend distally from the brachial plexus down each arm. Similarly, the limb peripheral nerves of the legs extend distally from the lumbar plexus and sacral plexus. A number of the larger limb peripheral nerves are identified in FIG. 1. As discussed further below, certain aspects of the present invention are particularly well suited to stimulation of limb peripheral nerves, including those identified in FIG. 1.

Figure 2:
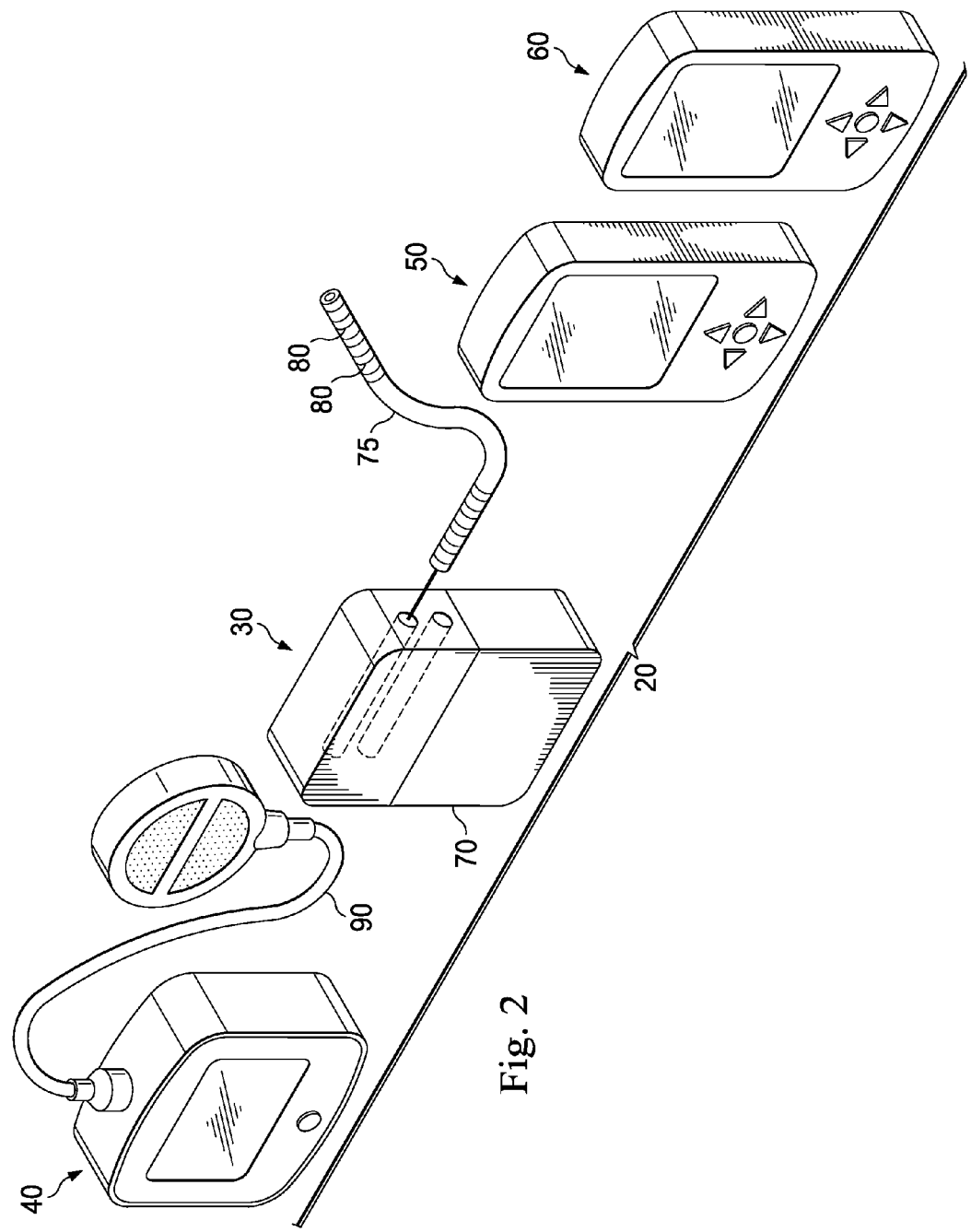
FIG. 2 is a simplified block diagram of an example medical system according to various embodiments of the present disclosure.

FIG. 2 illustrates a simplified block diagram of a medical system 20 to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. The implantable medical device 30 may include an implantable pulse generator (IPG) 70. In some embodiments, the IPG 70 is a peripheral neurostimulator (PNS) device. The IPG 70 is coupled to one end of an implantable lead 75. The other end of the implantable lead 75 includes multiple electrode surfaces 80 through which electrical current is applied to a desired part of a body tissue of a patient. The implantable lead 75 incorporates electrical conductors to provide a path for that current to travel to the body tissue from the IPG 70. Although only one implanted lead 75 is shown in FIG. 1, it is understood that a plurality of implanted leads may be attached to the IPG 70. Furthermore, the type of implanted lead that may be used in the medical system 20 is not limited to the embodiment shown in FIG. 1. For example, a paddle lead may be implemented in certain embodiments.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, or longer, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters. It is also understood that although FIG. 2 illustrates the patient programmer 50 and the clinician programmer 60 as two separate devices, they may be integrated into a single programmer in some embodiments.

Figure 3A:
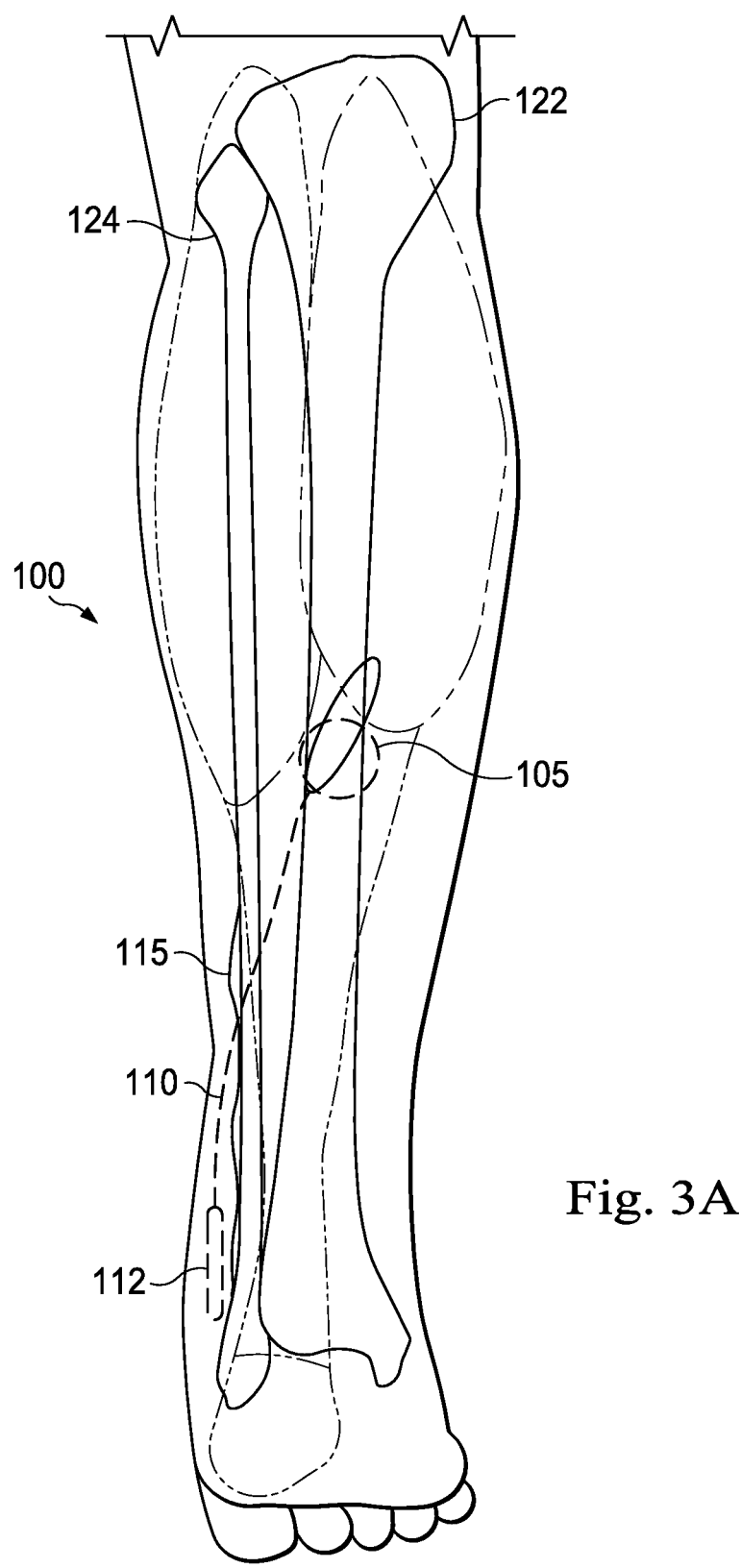
FIGS. 3A-3B illustrate stylized views of various portions of the human body with example peripheral neurostimulators implanted according to embodiments of the present disclosure.
Figure 3B:
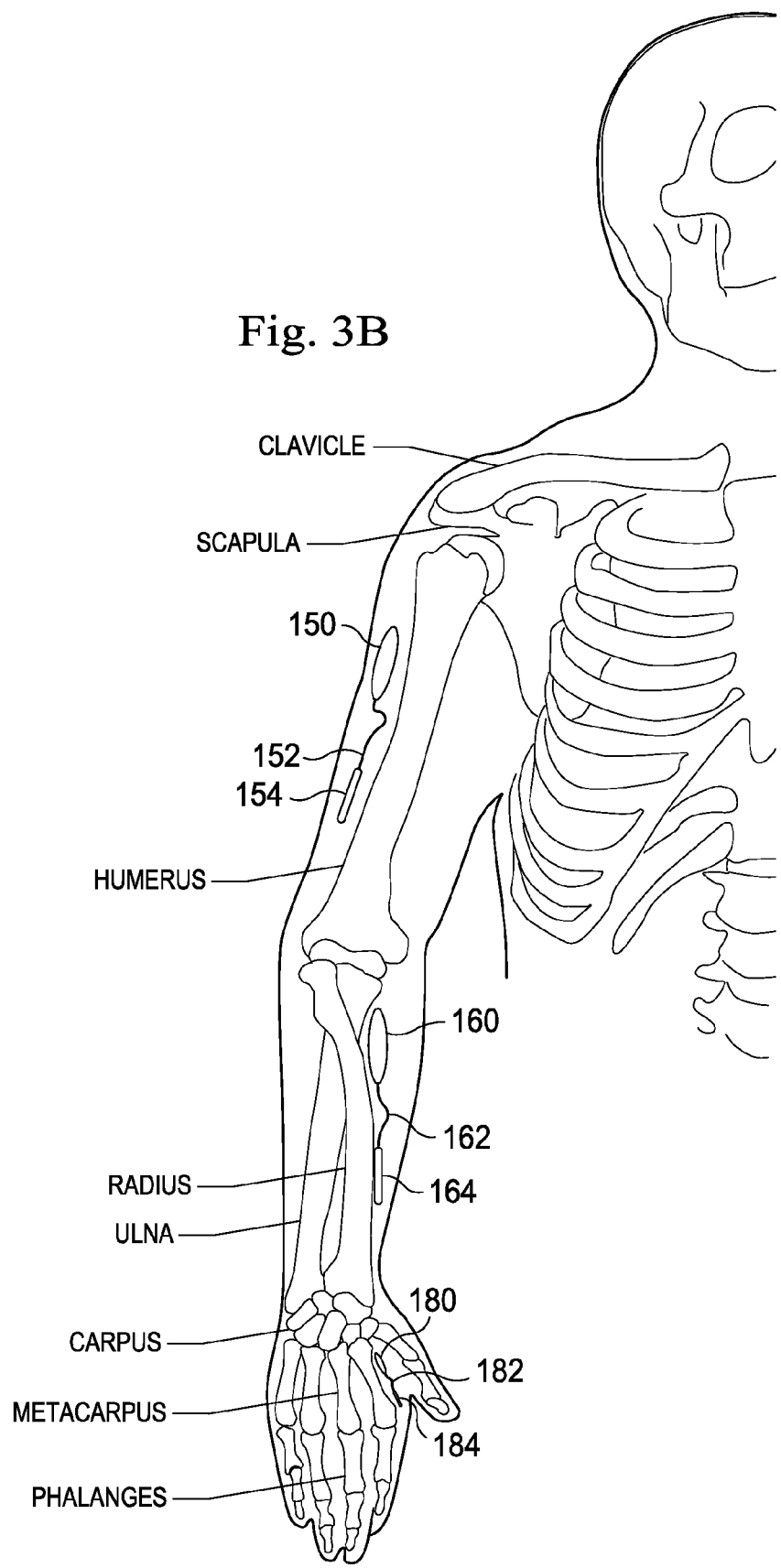

FIGS. 3A-3B illustrate various example regions of the human body within which a peripheral PNS device may be implanted. For example, referring to FIG. 3A, a lower leg 100 of a patient is illustrated. As an embodiment of the implantable medical device 30 discussed above with reference to FIG. 2, a PNS device 105 is implanted in the lower leg 100, for example, near the calf muscles. Through an elongate lead body 110, the PNS device 105 is electrically coupled to implanted electrodes 112. The electrodes are positioned for stimulation of the posterior tibial nerve 115. In the illustrated embodiment, the PNS device 105, the lead body 110, and the implanted electrodes 112 all reside below the knee and are contained within the length of the tibia 122 and the fibula 124. In other words, the lead body 110 does not traverse a joint as it extends between the PNS device 105 and the implanted electrode 112. In the illustrated embodiment, the PNS device 105, the lead body 110, and the implanted electrodes 112 are positioned between a knee joint and an ankle joint.

Referring now to FIG. 3B, another example PNS device 150 is implanted along the humerous bone. The PNS device 150 is coupled to implanted electrodes 154 through a lead body 152. The PNS device, the lead body 152, and the implanted electrodes 154 are positioned along the humerous bone without extending into or across the adjacent joints in the shoulder or elbow. Similarly, another example PNS device 160 may be implanted along and within the length of the radius and ulna bones. The PNS device 160 is coupled to implanted electrodes 164 through a lead body 162. The PNS device 160, the lead body 162, and the implanted electrodes 164 are implanted under the skin of the forearm but without any of the components extending into the adjacent joints of the elbow and the wrist. As yet another example, a PNS device 180 may be implanted along a metacarpus bone in the hand. The PNS device 180 is coupled to implanted electrodes 184 through a lead body 182. The implantation of the PNS device 180, the lead body 182, and the implanted electrodes 184 is configured such that none of them extends across an adjacent joint in the wrist or the fingers.

It is understood that FIGS. 3A-3B merely illustrate several example sites of the body in which a PNS device may be implanted to stimulate one or more target nerves (such as the posterior tibial nerve in FIG. 3A). A PNS device may also be implanted in a number of other different peripheral nerves locations shown in FIG. 1. For instance, a PNS device may be implanted in a patient's arms to stimulate one or more of the median, ulnar, radial, and brachial plexus nerves, as well as in a patient's legs to stimulate one or more of the tibial, saphenous, sciatic, and femoral nerves. For reasons of simplicity, these configurations are not specifically illustrated herein.

Figure 4:
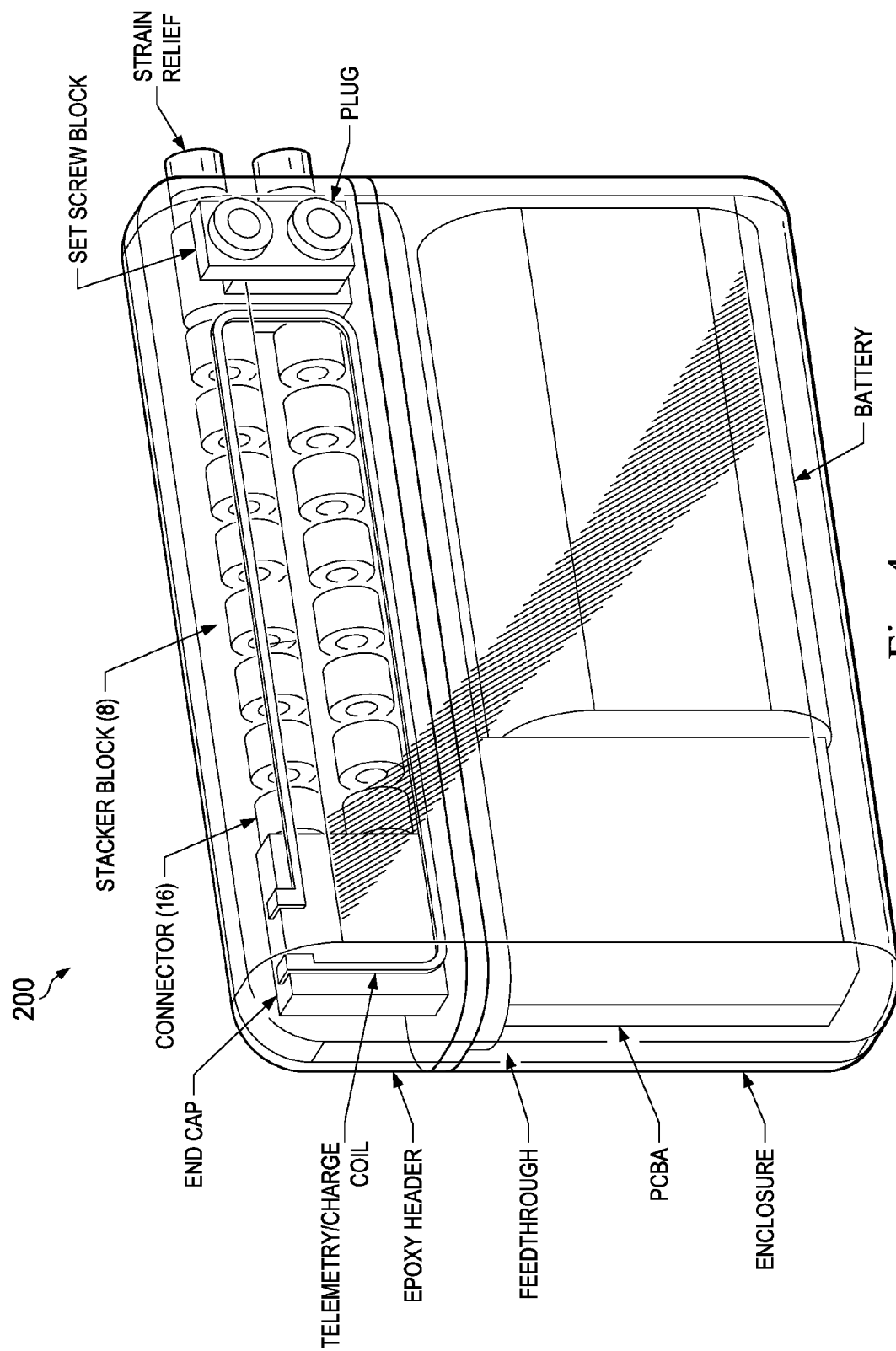
FIGS. 4-5 illustrate an example peripheral neurostimulator according to an embodiment of the present disclosure.
Figure 5:
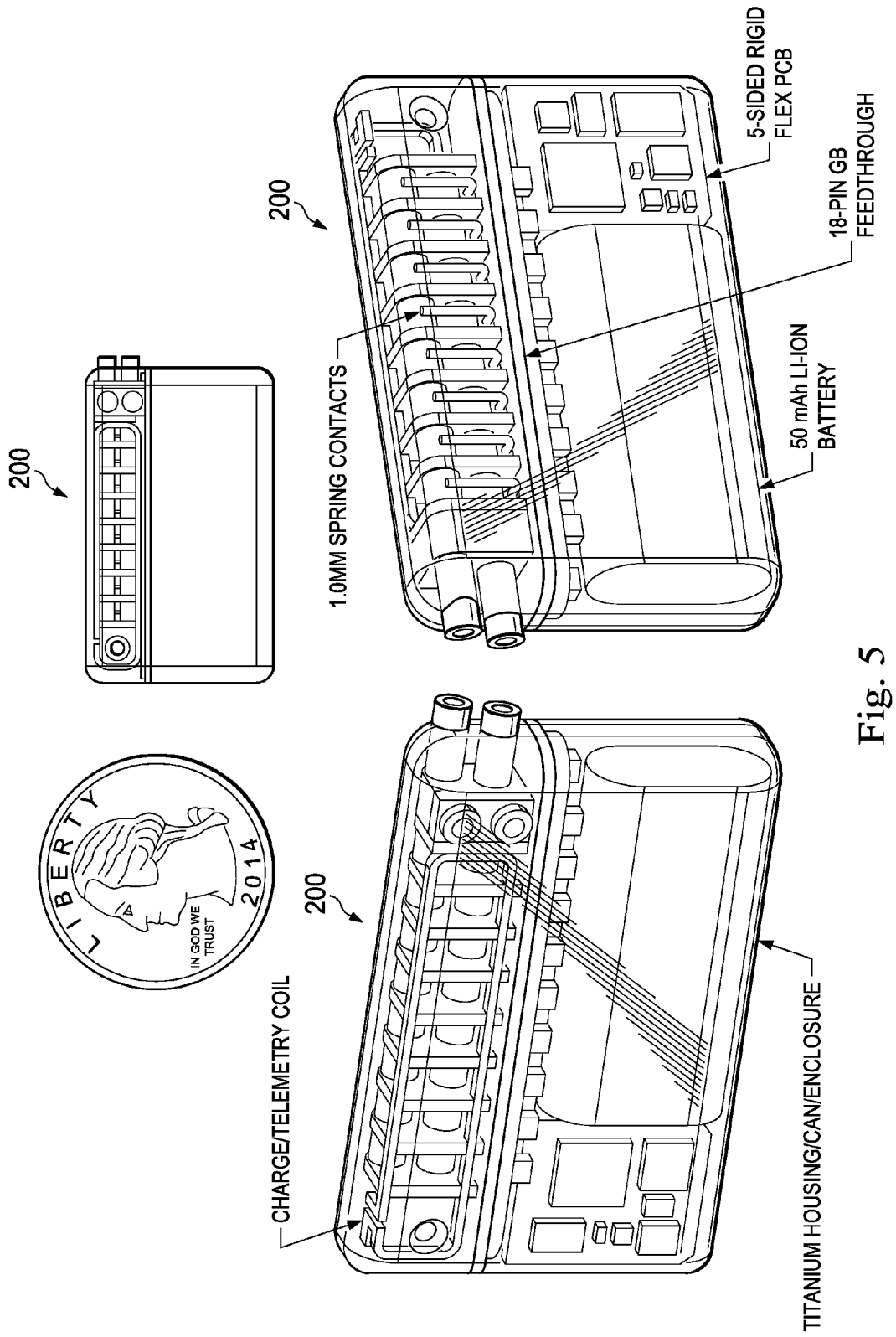

Referring now to FIGS. 4-5, a PNS device 200 is illustrated according to an embodiment of the present disclosure. In general, peripheral nerve stimulation is a technique configured to provide medical therapy for different diseases and/or to treat different types of pain. Depending upon the therapeutic application, peripheral nerve stimulation systems generally seek to activate only motor nerves (e.g., for functional purposes, such as dorsiflexion for a dropped foot, or a grasp for upper extremity hemiplegia) or only sensory nerves (e.g., for neuropathic pain management).

In treating pain, stimulation of innocuous sensory fibers in the periphery ostensibly affects pain transmission to the brain via the Gate Control Theory. Clinically, stimulation of these fibers usually results in a comfortable, moderate 'buzzing' sensation in the area of pain, termed paresthesia.

In general, peripheral nerve stimulation can utilize relatively simple stimulation techniques to provide excellent therapy. However, PNS therapy today is generally delivered by equipment designed for spinal cord stimulation (SCS). Spinal cord stimulation equipment utilizes large and over-powered implantable pulse generators (IPGs) designed not for stimulating peripheral nerves, but is designed to deliver electrical pulses to the spinal column. IPGs designed for SCS is also placed in large pockets in the lower back/upper buttock, rather than being implanted near the targeted peripheral nerve for electrical stimulation. These poorly adapted technologies for peripheral nerve therapy can cause significant tissue morbidity in the need to route the wires between the targeted peripheral nerve and the distantly located IPG unit. This, in turn, can result in frequent device failure (and thus therapy failure) due largely to lead migration and breakage. In many cases where SCS equipment was used for PNS, a large percentage of patients needed revision surgeries to address issues with the SCS IPG and leads. Additionally, while some peripheral nerve pain can be addressed by stimulating the nerve root through SCS of the spinal column, it can be difficult to achieve effective pain relief with respect to a targeted nerve and anatomy without affecting nearby, undesired areas.

To overcome the limitations associated with using SCS equipment to perform PNS, the present disclosure provides a small, flexible PNS system—an example embodiment of which includes the PNS device 200 shown in FIGS. 4-5—that can be made simple and small enough to be deployed in a minimally invasive surgical procedure, locally to the region of the targeted nerves, thereby avoiding tunneling through tissue to remote regions of the anatomy.

In some embodiments, the PNS system is characterized by a low parts count, low cost-of-goods, ease of manufacturability, a high energy density long lasting rechargeable battery, use of known biocompatible materials, compatibility with industry preferred electrode/lead systems, and a hermetic implantable device geometry that is well suited for most preferred anatomical locations. In some embodiments, the system, although simplified, is still flexible enough to handle a wide range of unilateral and bilateral applications, has high stimulation power output capability, covers accepted ranges of therapeutic waveform frequency and duration, can drive multiple leads of eight or more contacts each, and utilizes custom software applications reconfigurable for the different clinical applications (e.g., pain, incontinence, depression, epilepsy, etc.).

In some embodiments, the PNS system of the present disclosure includes the PNS device 200 in the form of a hermetically-sealed implantable pulse generator. The PNS device 200 has a miniature form factor. For example, the PNS device 200 may have a total volume of less than 5 cubic centimeters and a thickness less than 5 millimeters. To illustrate the small dimensions of the PNS device 200, FIG. 5 shows the PNS device 200 next to a quarter. As can be seen in FIG. 5, the PNS device 200 is shorter than the quarter and not much longer either. Such small package size of the PNS device 200 enables comfortable and cosmetically attractive placement of the PNS device 200 on the limbs of the patient.

Furthermore, the PNS device 200 offers one or more of the following features:

Active can/enclosure technology that allows for broader stimulation fields;

Deep drawn small but shallow rectangular form factor for the can that allows for ease of manufacture and low cost;

Connects to proximal ends of "industry standard" electrodes, which have become preferred for ease of handling characteristics;

Single piece high reliability connector stack;

High density pin-less hermetic feedthrough connection system;

Two reversibly connectable header ports enable connection of two leads for multi-region stimulation targeting, nominally distal from implanted package;

High number of contacts per lead to allow for a wide range of lead designs (for instance, 8 tightly spaced contacts per lead) and different therapeutic applications (for instance, chronic intractable pain).

In addition to the PNS device 200, the PNS system of the present disclosure may also include an external stimulator used for trial therapy periods, one or more leads with corresponding electrodes, an extension for a lead/electrode, accessories such as lead anchors and surgical procedure tools, a remote control and pulse generator charger that may be combined into one device, and/or a remote controller for physician or patient programming use.

Figure 6A:
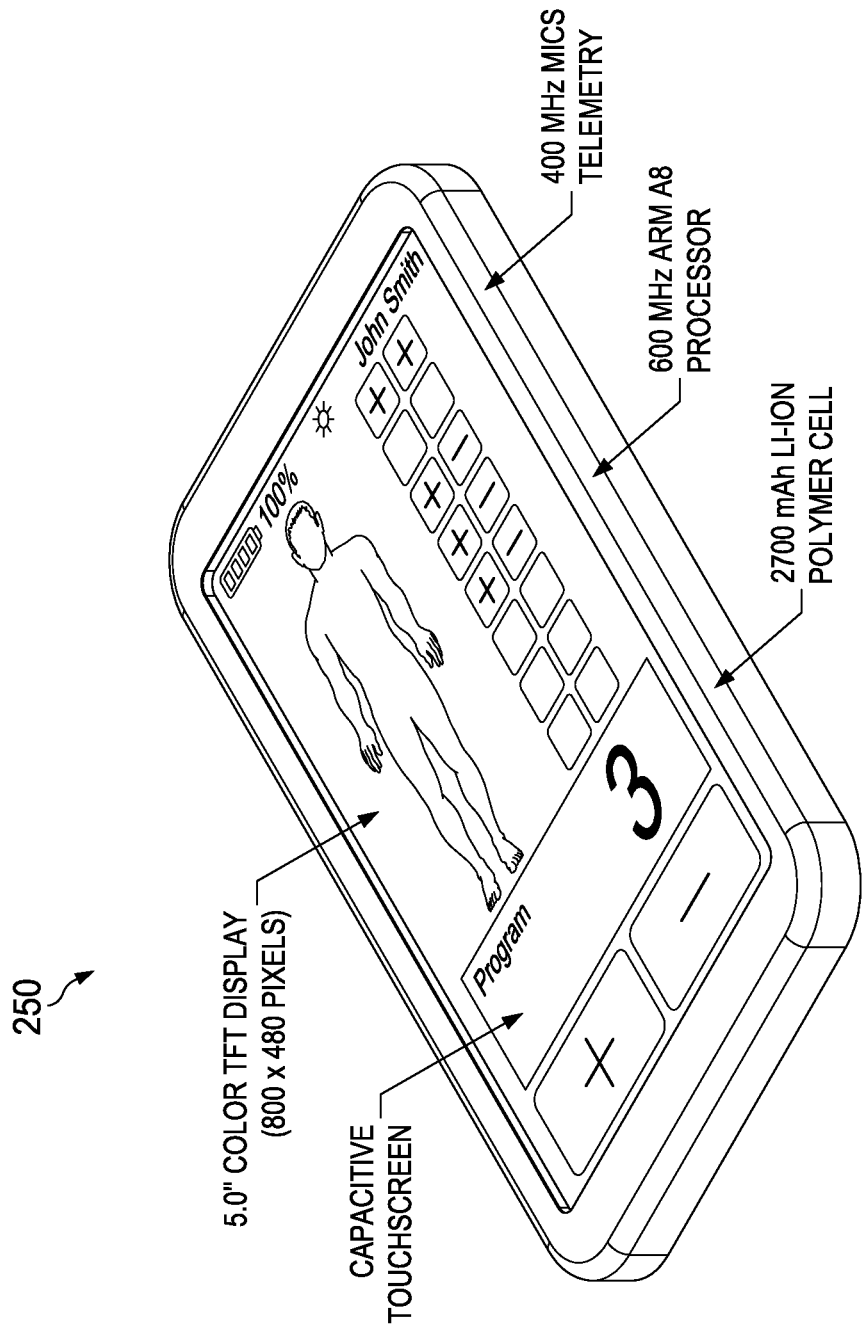
FIGS. 6A-6C illustrate an example programmer for a neurostimulator according to an embodiment of the present disclosure.
Figure 6B:
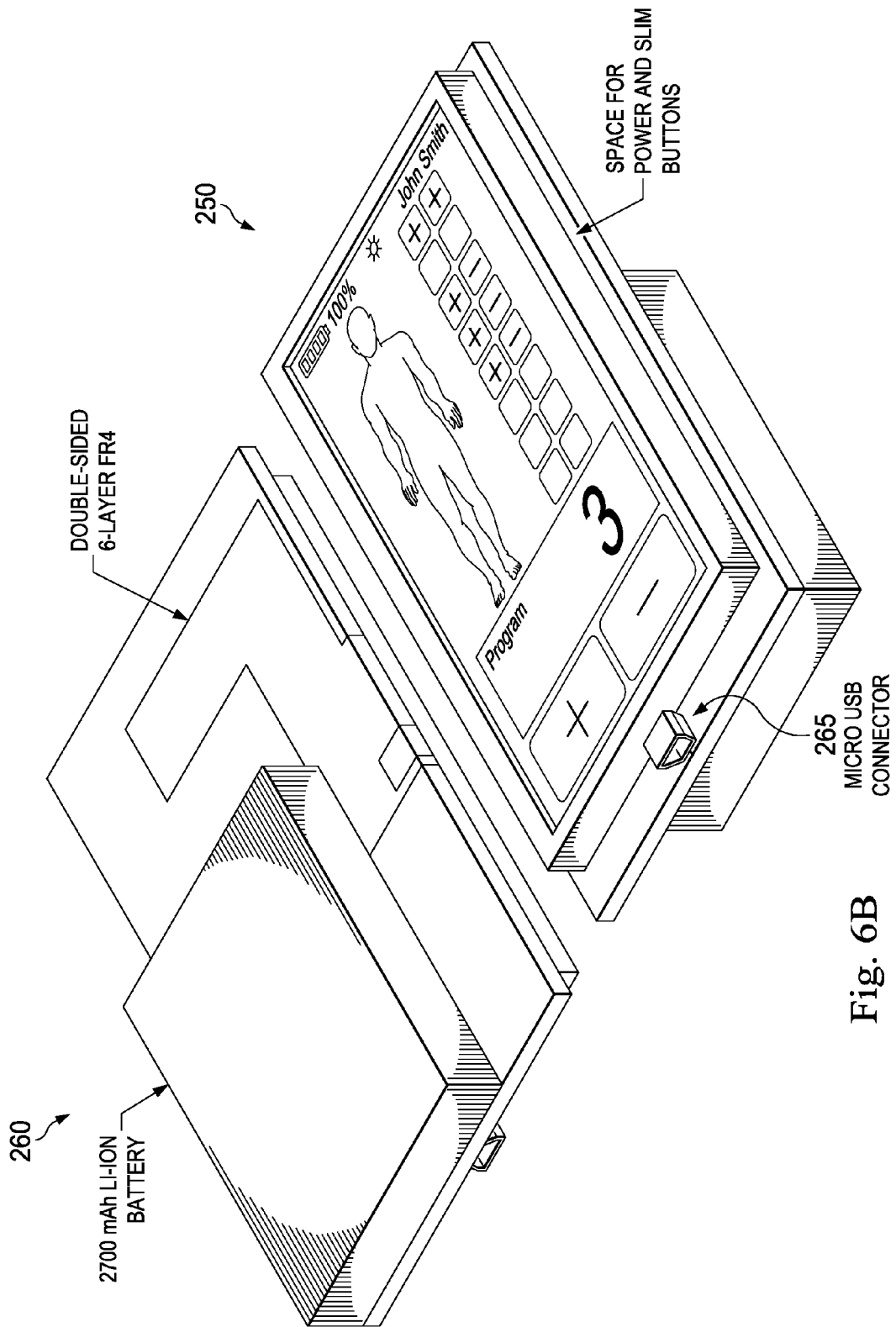
Figure 6C:
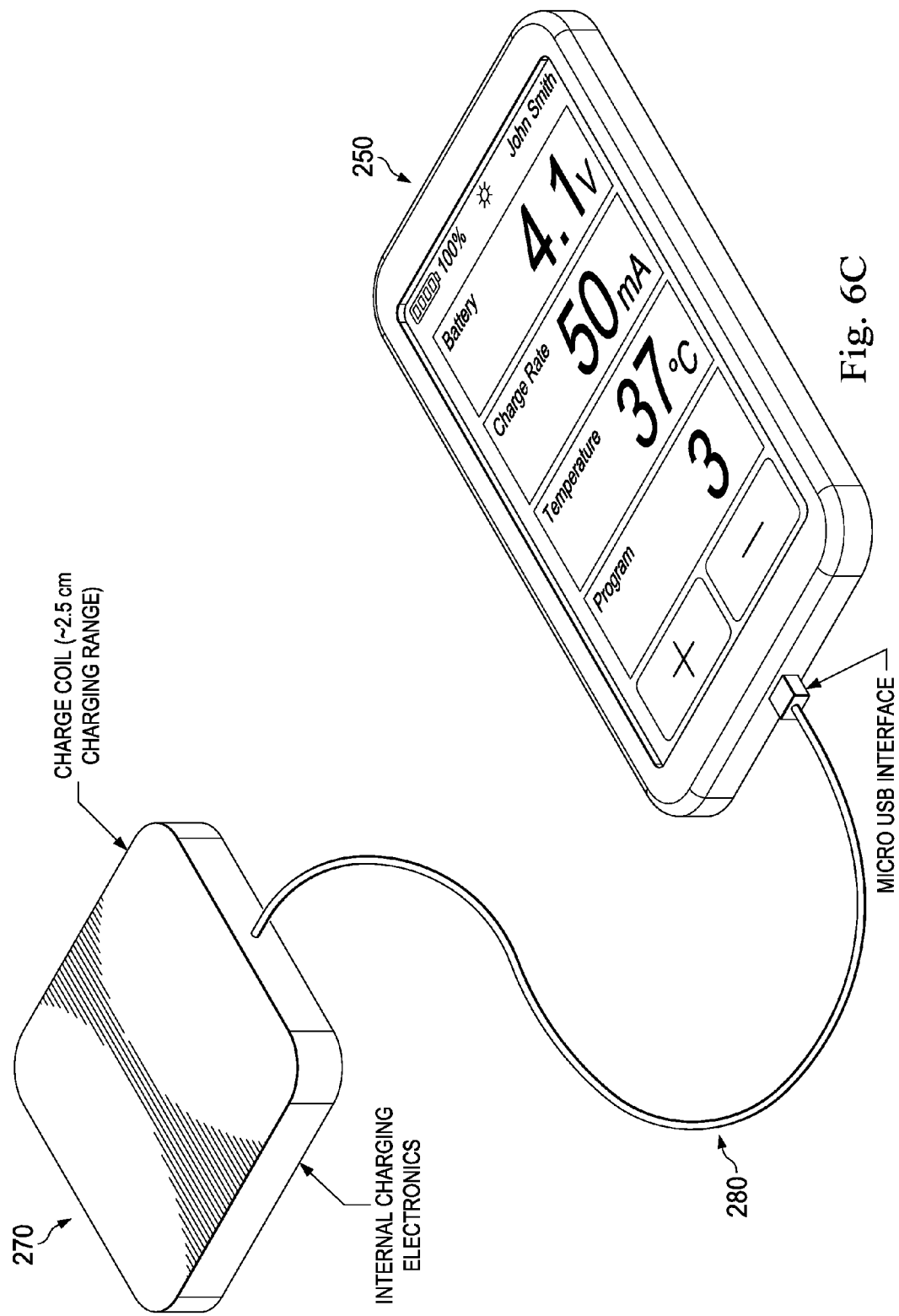

For example, FIGS. 6A-6C illustrate an example electronic programmer 250 configured to send programming instructions to the PNS device 200. The PNS device 200 generates a corresponding electrical stimulation therapy (e.g., a series of electrical stimulation pulses) in response to the received programming instructions. In certain embodiment, the electronic programmer 250 is configured to be used by either the patient or a healthcare professional. As such, the electronic programmer 250 may be viewed as an embodiment of the patient programmer 50 and the clinician programmer 60 integrated together as a single device.

As is shown in FIG. 6A, the electronic programmer 250 has a "smartphone-like" industrial design. For example, the electronic programmer 250 has a touchscreen (e.g., a capacitive touchscreen) graphical user interface with virtual buttons and input/output fields. The electronic programmer 250 may also have tactile buttons that provide an immediate control input to the programmer 250 for quick and simple core system functions. Such "smartphone-like" design reduces the stigma of using a medical device. The "smartphone-like" design of the electronic programmer also makes it easier for the user of the electronic programmer to learn how to use it quickly, since smartphones have become very popular, and most people are comfortable interacting with a smartphone-like user interface.

Aside from its elegant and intuitive industrial design, the electronic programmer 250 also offers flexible functionalities. For example, the electronic programmer 250 may be configurable from patient to patient, according to the patient's level of technical competence and/or comfort. The electronic programmer 250 may also be reconfigurable via firmware for different therapeutic applications (for instance, chronic intractable pain). Furthermore, the electronic programmer 250 may have multiple user modes: e.g., patient programming and patient charging mode (both configurable by a clinician), clinician mode, engineering mode, diagnostic mode, etc.

Referring to FIG. 6B, the electronic programmer 250 also includes an onboard battery 260. In the illustrated embodiment, the battery 260 is sealed within the housing of the electronic programmer 250 and is non-removable. In alternative embodiments, however, the battery 260 may be user-removable. The battery 260 is a rechargeable battery. In various embodiments, the battery 260 has a capacity ranging from about 400 milli-amp hours (mAh) to about 4000 mAh, for example with a capacity around 2700 mAh. The rechargeable nature of the battery 260 allows it to have a reduced size and mass.

The electronic programmer 250 also has a USB port 265, which allows the electronic interchange (e.g., telemetry or power) between the electronic programmer 250 and external devices. For example, referring to FIG. 6C, a charger 270 is coupled to the USB port 265 of the electronic programmer 250 through a USB cable 280. The battery 260 may provide power to the charger 270, which contains internal charging electronics and a charge coil for inductively charging the PNS device 200 discussed above. This type of power/charging configuration shown in FIGS. 6B-6C greatly simplifies patient tasks with respect to charging the PNS device 200, as patients only has a few things to manage. In addition, charging can be done at any time as needed and while the patient is ambulatory/mobile.

The electronic programmer 250 and the charger 270 are also both implemented in small and lightweight packages. For example, they may each have a thickness less than about 10 millimeters (mm). The small size of the electronic programmer 250 and the charger 270 enables comfortable, convenient, and cosmetically attractive wearing of the electronic programmer 250 and/or the charger 270 on a patient's limb, for example with a detachable belt or band. In some embodiments, the relative simplicity and versatility of the electronic programmer 250 discussed above reduce or eliminate the need for a cumbersome separate clinician programmer.

The various sections and components of the PNS device 200 will now be discussed in more detail below.

Figure 7:
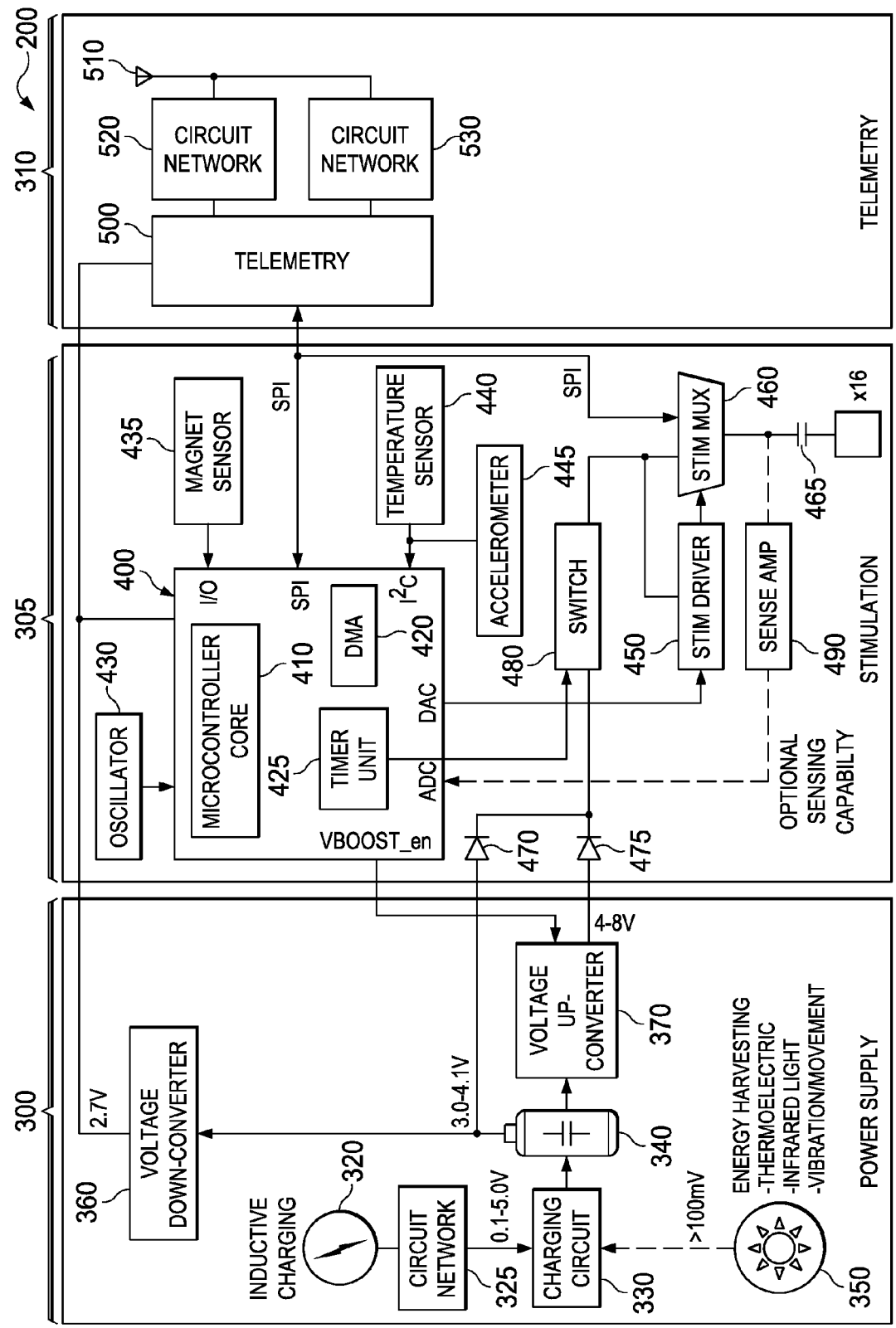
FIG. 7 illustrates a simplified block diagram of an example peripheral neurostimulator according to an embodiment of the present disclosure.
Figure 8A:
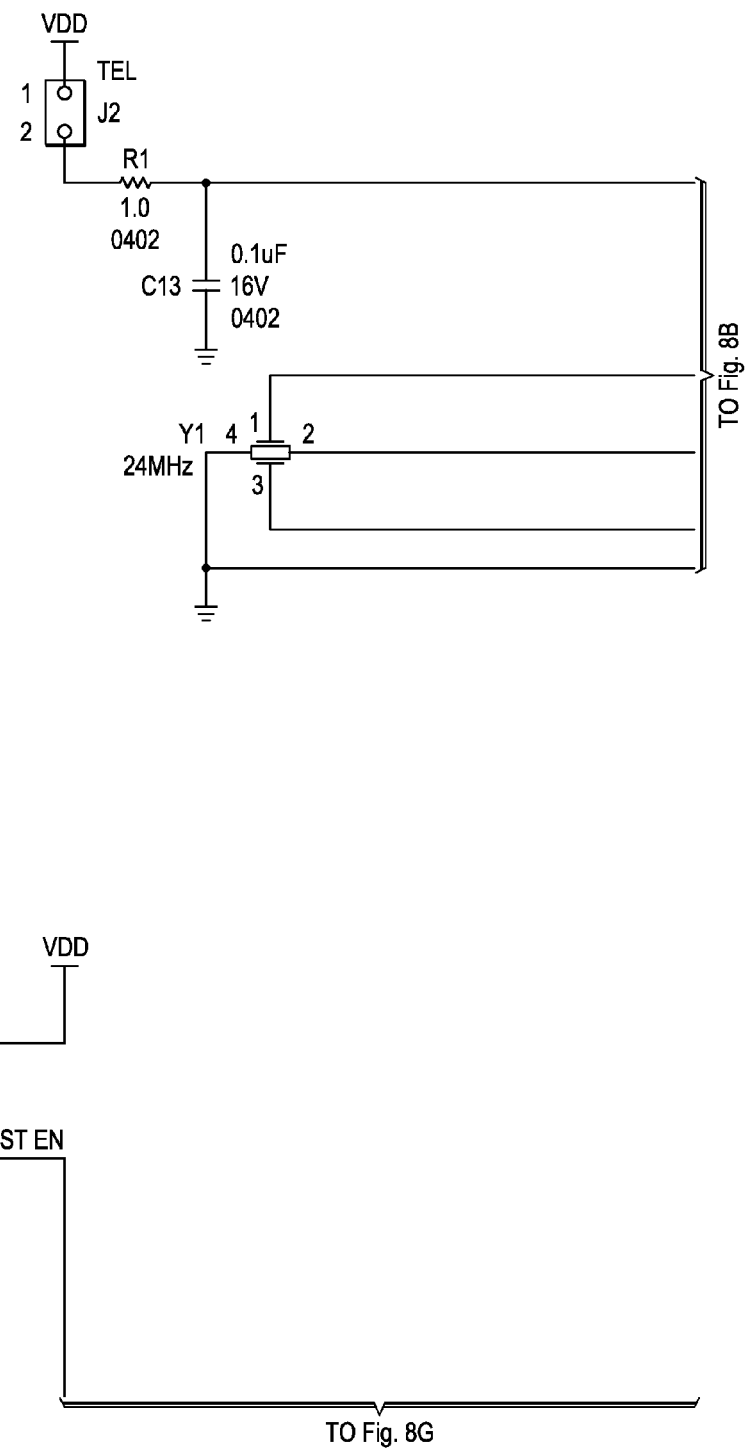
FIGS. 8A-8L illustrates a circuit schematic of the peripheral neurostimulator of FIG. 7 according to an embodiment of the present disclosure.
Figure 8B:
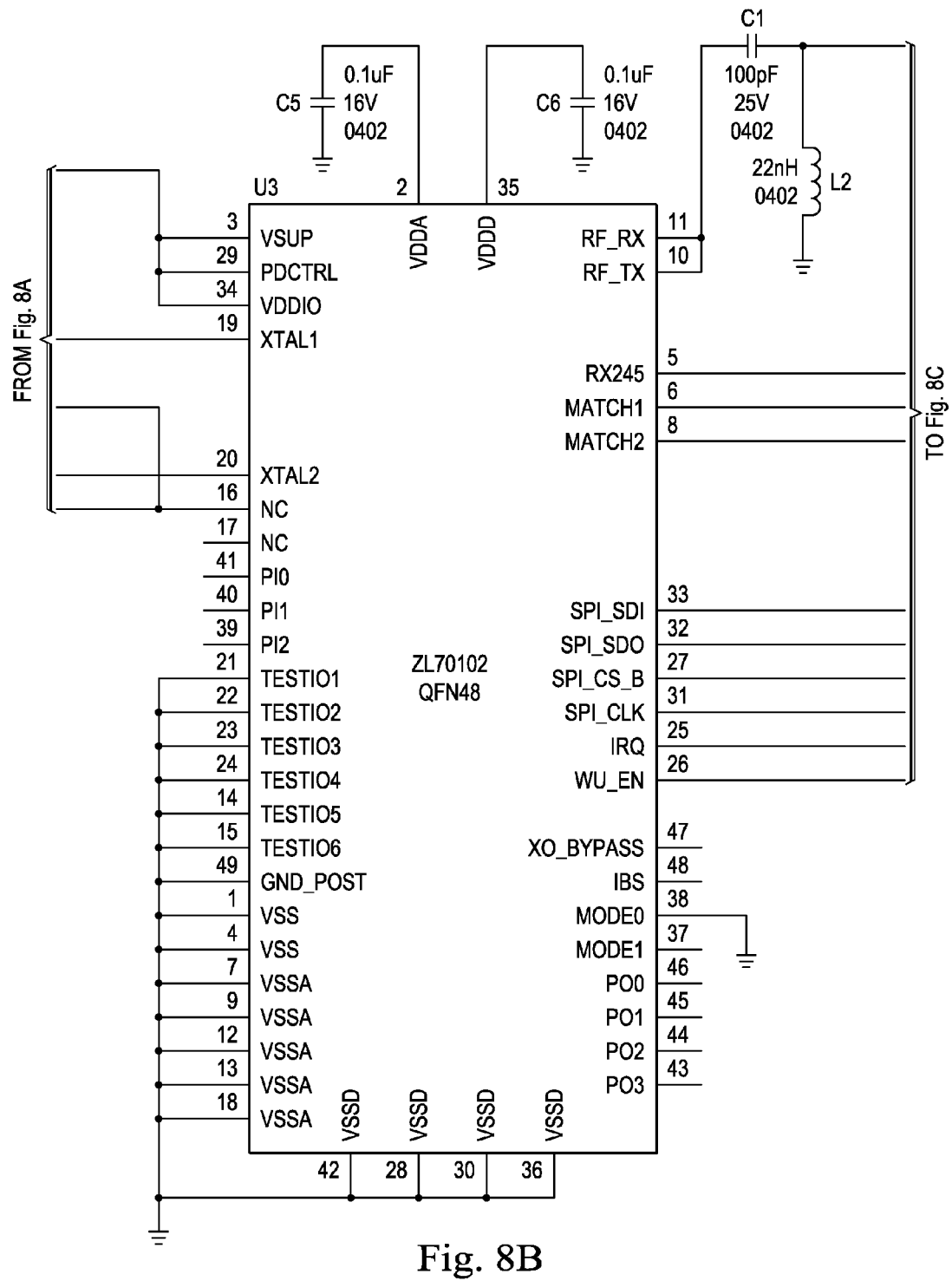
Figure 8C:
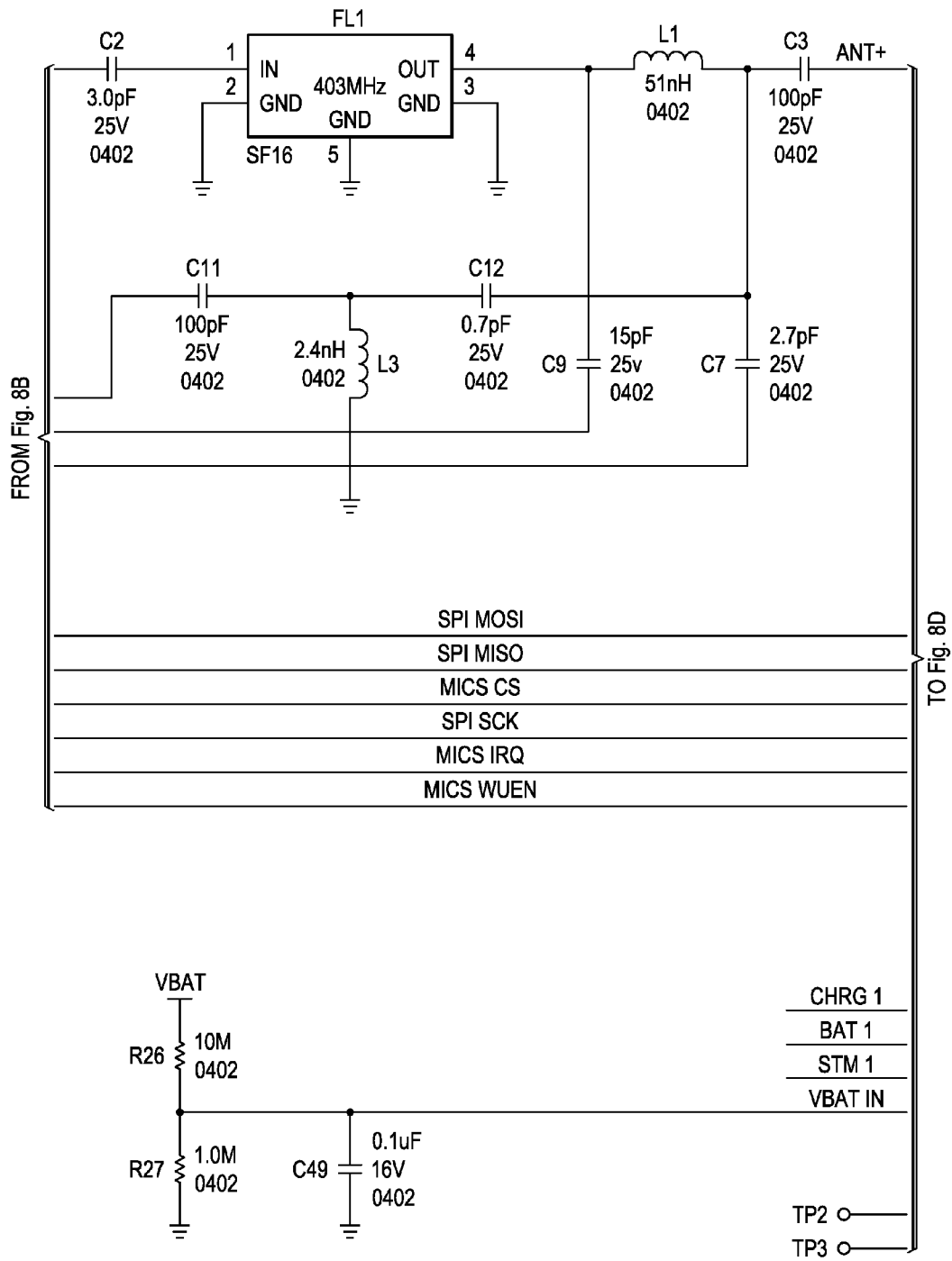
Figure 8D:
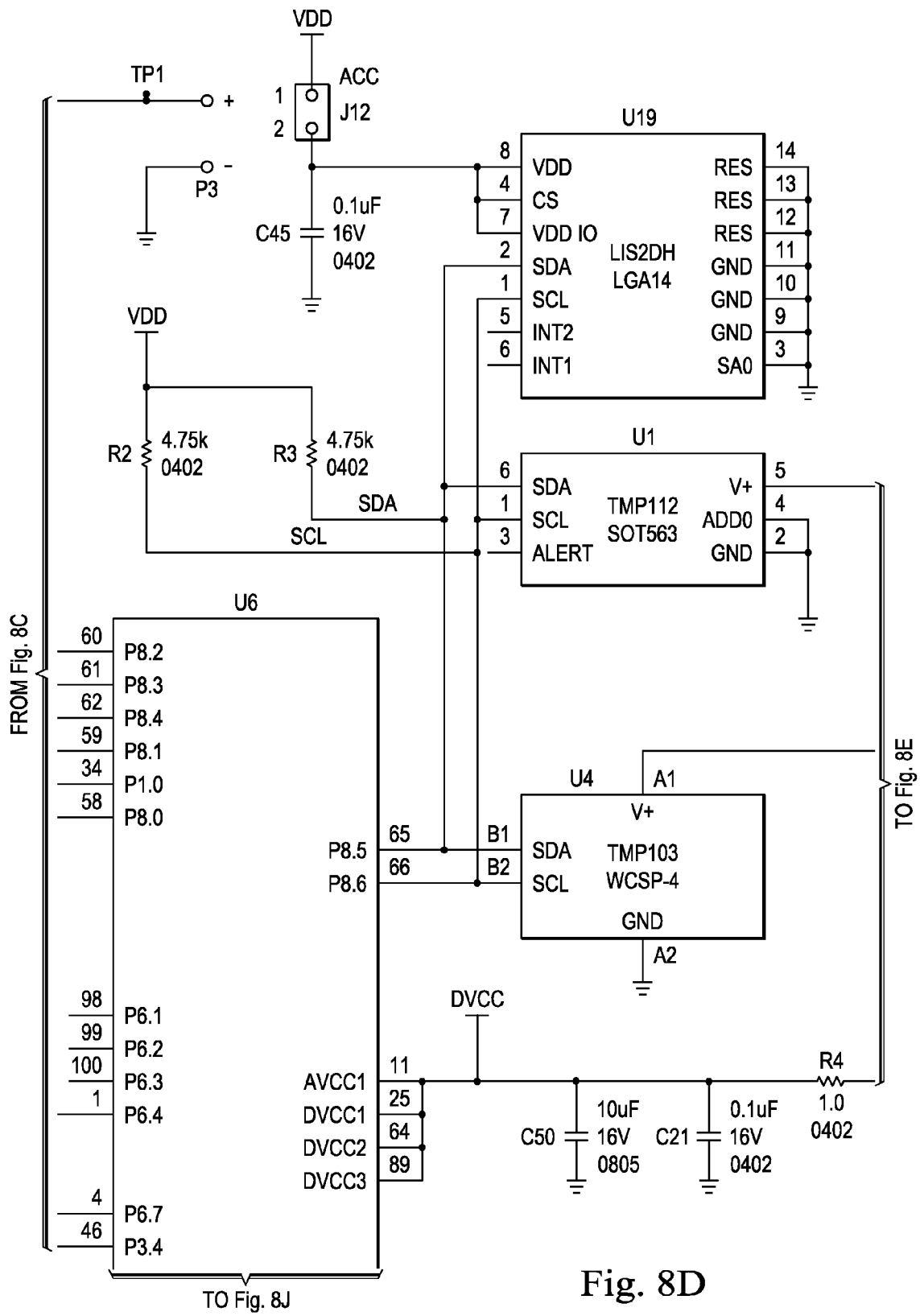
Figure 8E:
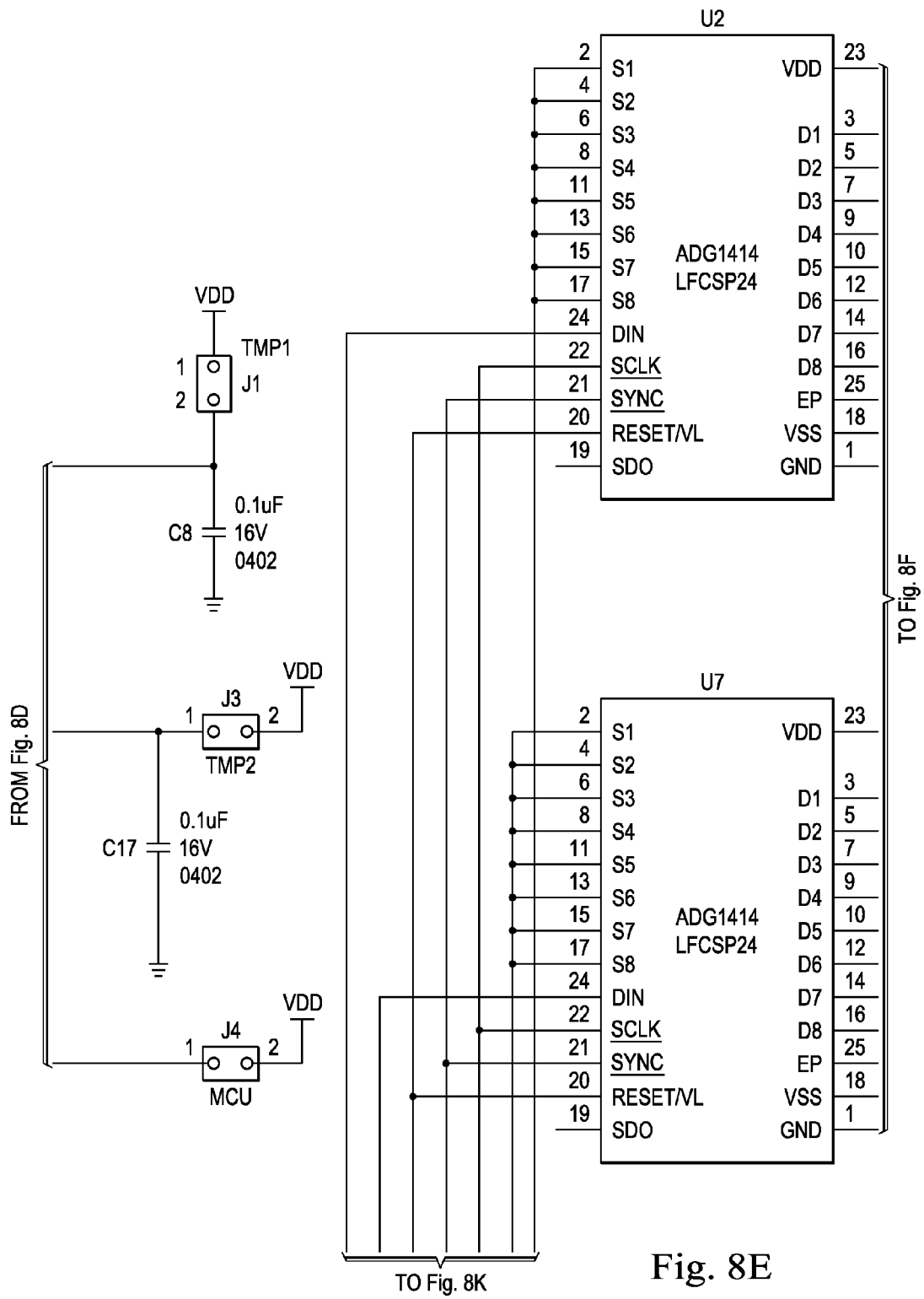
Figure 8F:
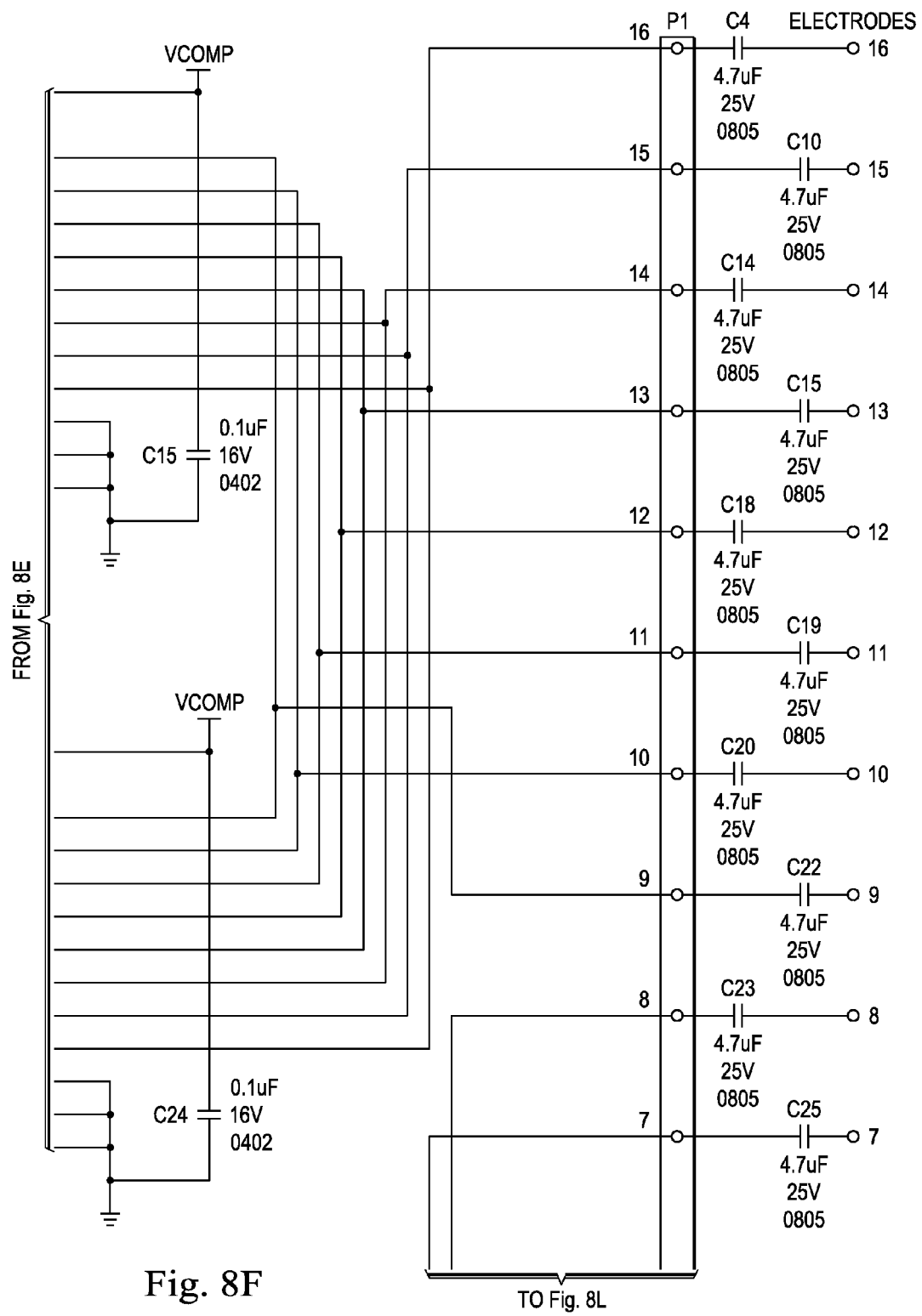
Figure 8G:
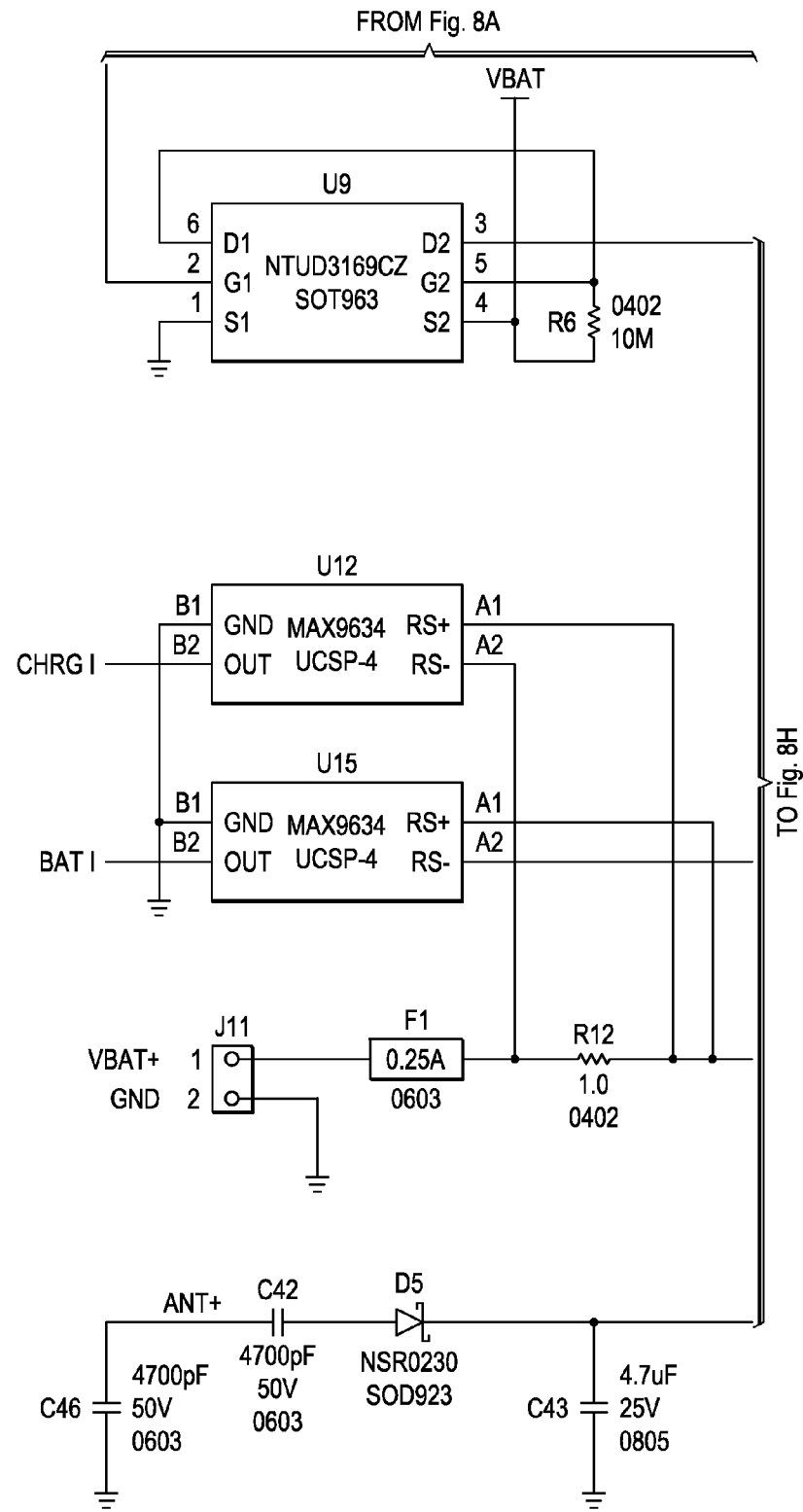
Figure 8H:
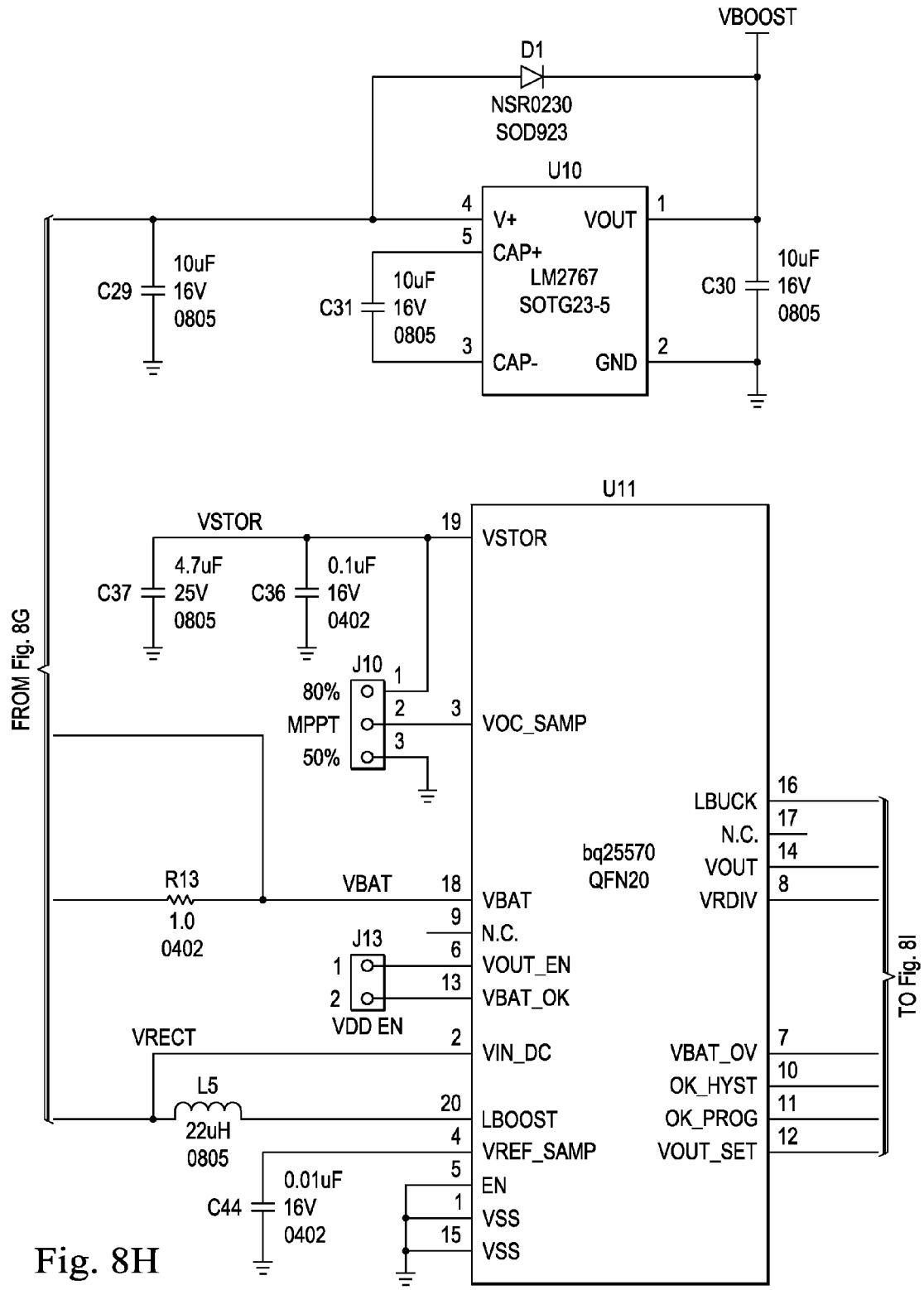
Figure 8I:
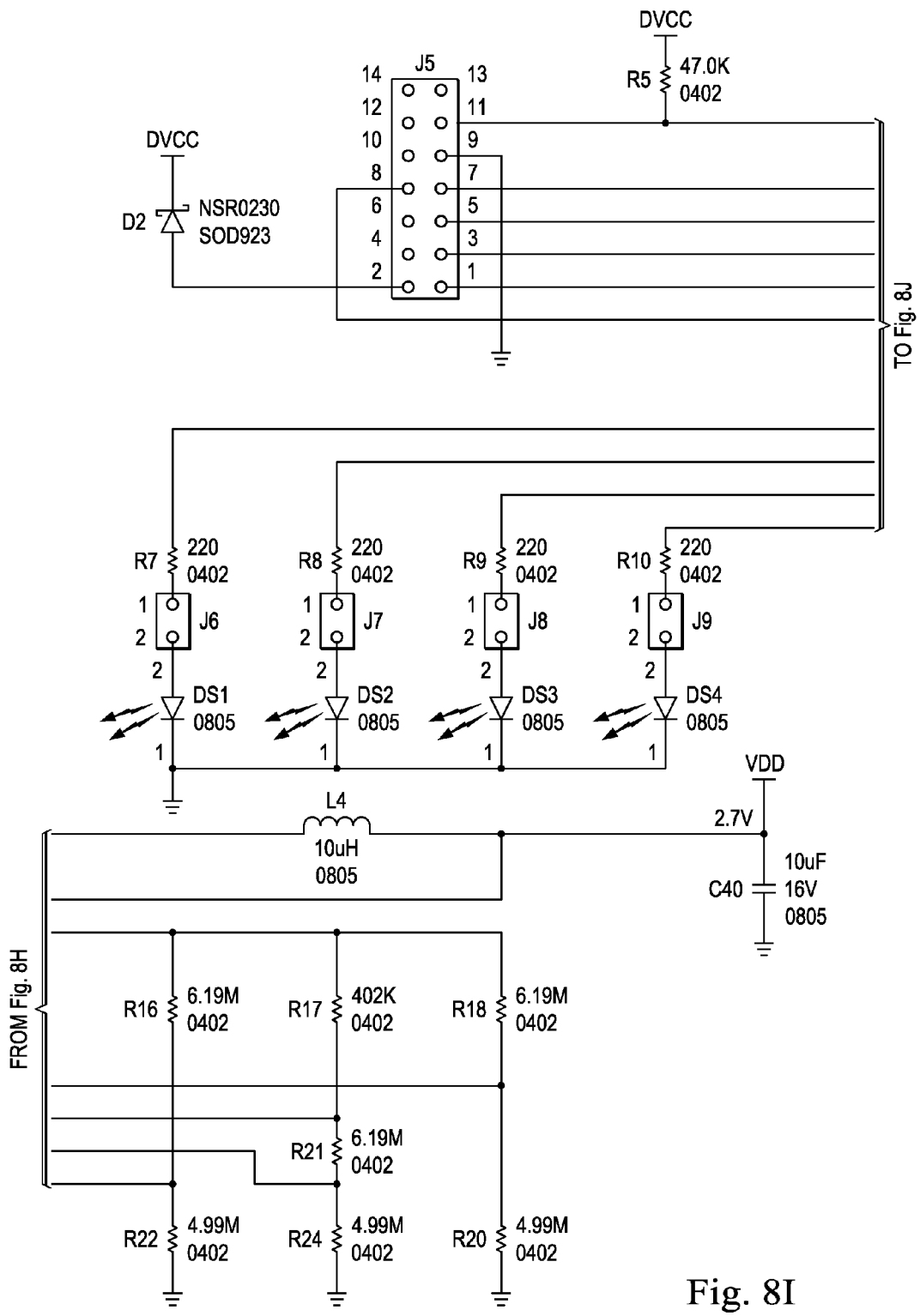
Figure 8J:
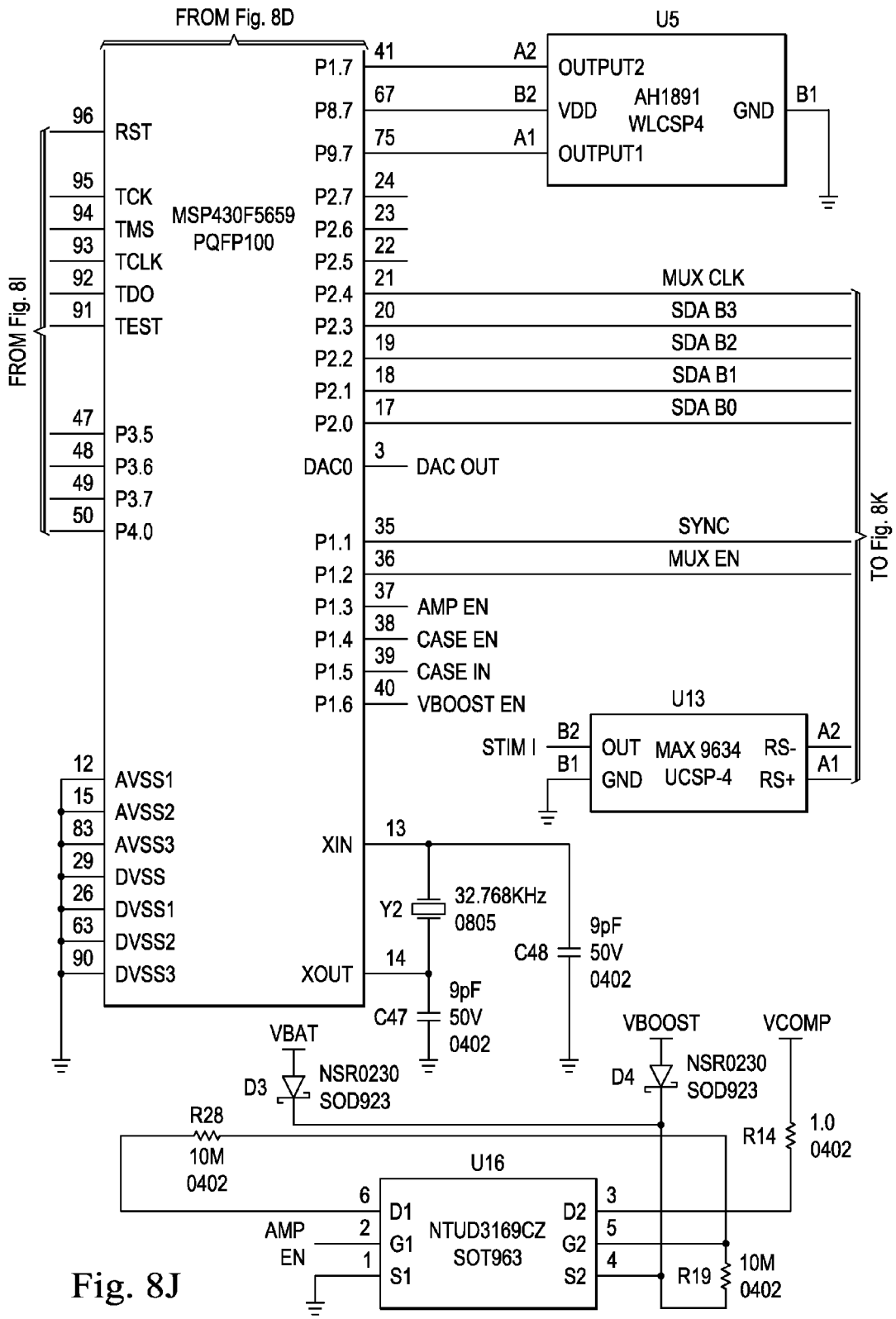
Figure 8K:
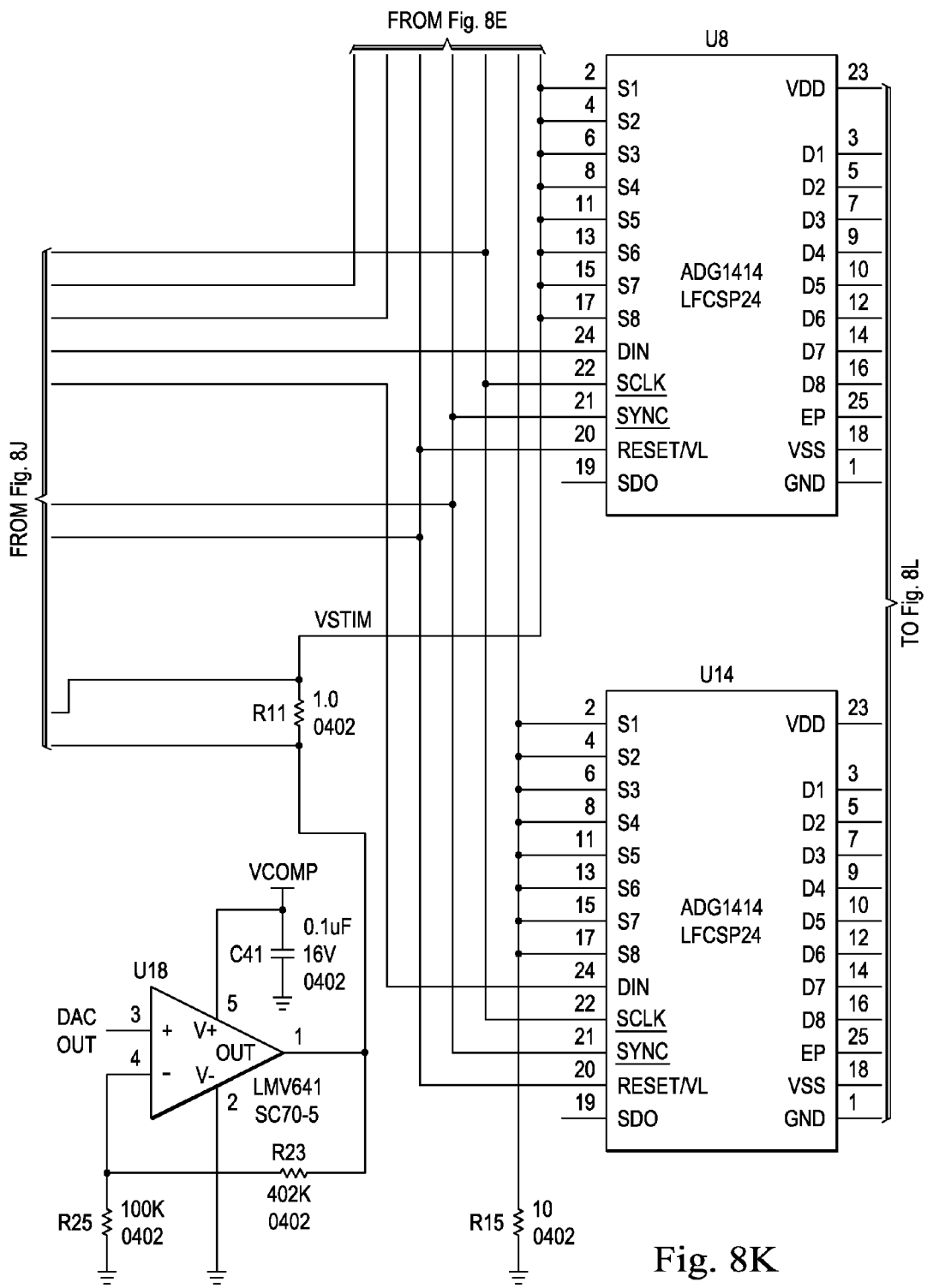
Figure 8L:
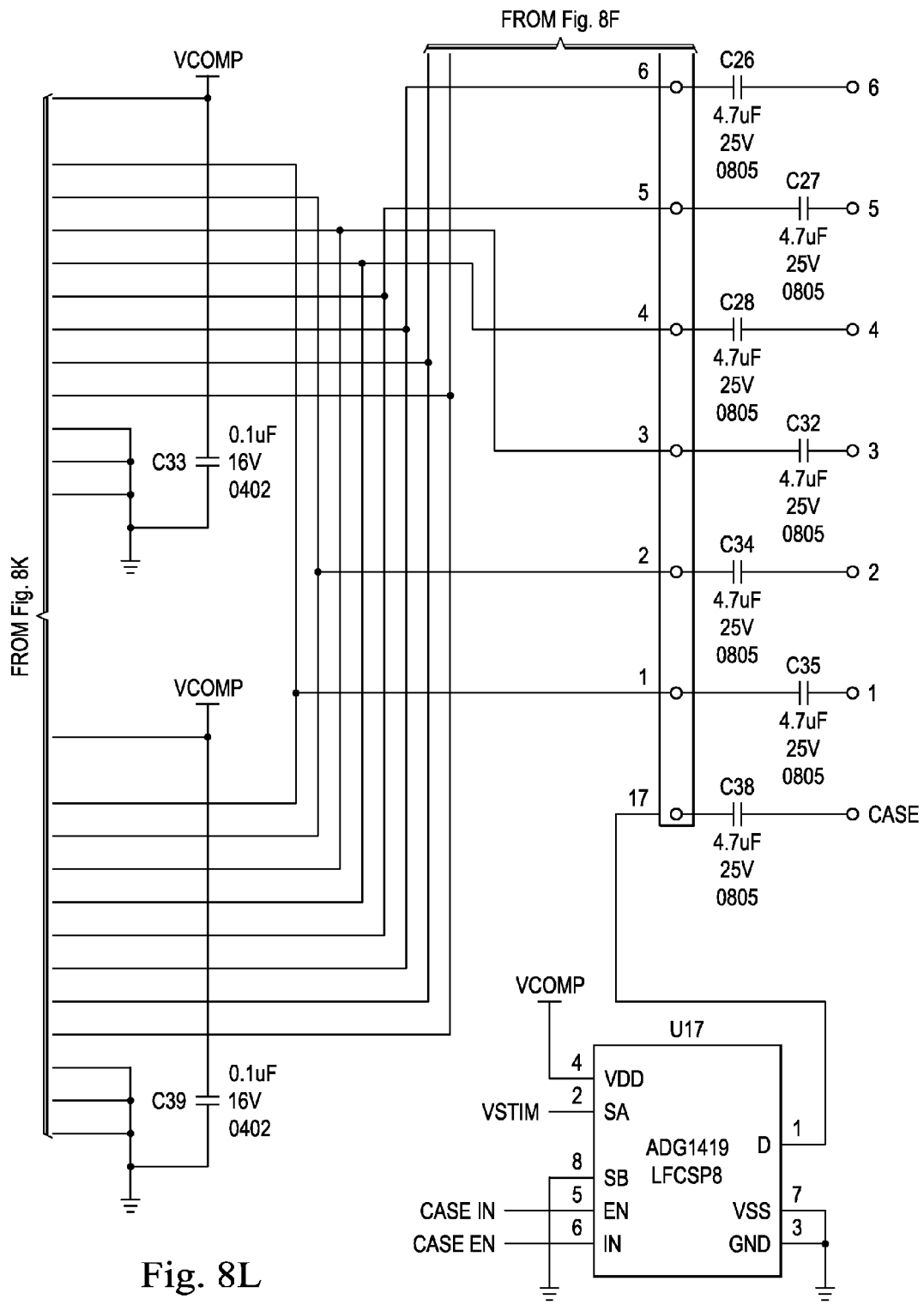

Referring to FIG. 7, a simplified block diagram of the PNS device 200 is illustrated. The PNS device 200 includes a power supply circuitry section 300, a stimulation circuitry section 305, and a telemetry circuitry section 310. The power supply circuitry section 300 includes an inductive charging component 320. In some embodiments, the charging component 320 includes a coil for receiving power/energy inductively from an external charger, for example from the charger 270 discussed above with reference to FIG. 6C. In some embodiments, the inductive energy (i.e., the charging signal) received from the inductive charging component 320 ranges from about 0.1 volts to about 5 volts in amplitude, and it has a frequency range that is within one of the Industrial, Scientific, and Medical (ISM) radio bands. For example, in some embodiments, the inductive energy is in a 13.56 Mhz band, that is, it ranges from 13.553 Mhz to 13.567 Mhz with a center frequency at 13.56 Mhz. In other embodiments, the inductive energy may be in alternative ISM radio bands.

The power supply circuitry section 300 further includes a circuit network 325. The circuit network includes microelectronic components that provide a resonant frequency at or near the center frequency of the ISM radio band associated with the inductive energy received by the charging component 320. Thus, in the embodiments where the inductive energy is in the 13.56 Mhz ISM radio band, the microelectronic components of the circuit network 325 provide a resonant frequency at or near 13.56 Mhz. This resonant frequency allows the inductive energy to pass through, but effectively rejects signals from outside the selected ISM radio band. For example, telemetry signals that have much higher (or lower) frequencies than the selected ISM radio band will be blocked by the circuit network 325. In this manner, the circuit network 325 may function similar to a filter. The various aspects of the circuit network 325 will be discussed in greater detail below.

The power supply circuitry section 300 also includes a charging circuit 330 that is electrically coupled to the inductive charging component 320. The charging circuit 330 includes various electronic components that convert the inductive energy received from the inductive charging component 320 into a direct current (DC) voltage. In some embodiments, the charging circuit 330 may include a voltage booster that can convert a lower input voltage to a higher output voltage, so as to adequately charge a battery 340 coupled thereto. In some embodiments, the battery 340 is configured to output a DC output voltage ranging from about 3.5 volts to about 4 volts. Thus, the charging circuit 330 can boost an input voltage (e.g., received from the inductive charging component 320) to meet or exceed the requisite DC output voltage of the battery 340.

The power supply circuitry section 300 further includes an energy harvesting component 350 that is configured to supply power to the battery 340. As is illustrated, the output of the energy harvesting component 350 is electrically coupled to the charging circuit 330, which boosts the energy harvested by the energy harvesting component to a level that can be used to charge the battery 340. In some embodiments, the energy harvesting component 350 includes a thermoelectric generator (TEG) that converts the body heat of the patient (inside whom the PNS device 200 is implanted) to electrical energy. The converted electrical energy may then be used to charge the battery 340 (after being boosted up by the charging circuit 330). In some other embodiments, the energy harvesting component 350 may also include circuitry to convert infrared light and/or vibration and movement of the patient into electrical energy. In various embodiments, the electrical energy harvested by the energy harvesting component 350 may exceed about 100 millivolts (mV).

The power supply circuitry section 300 also includes a voltage down-converter 360 coupled to the battery 340. The voltage down-converter 360 converts the nominal DC output voltage of the battery 340 to a lower level suitable for powering some of the electronic circuitry of the PNS device 200, such as a microcontroller, amplifiers, and telemetry circuitry (discussed below in more detail). For example, in embodiments where the DC voltage output of the battery 340 is about 4 volts, the down-converter 360 reduces it to about 2.7 volts. In the illustrated embodiment, 2.7 volts is a sufficient voltage to power electronic components such as the microcontroller, amplifiers, or the telemetry circuitry, and thus there is no need to waste the higher voltage output (e.g., 4 V) produced by the battery 340. In other words, the voltage down-converter 360 saves energy by down-converting the DC voltage output of the battery 340. In some embodiments, the voltage down-converter 360 includes a buck regulator or a low-dropout (LDO) linear regulator.

The power supply circuitry section 300 further includes a voltage up-converter 370 coupled to the battery 340. The voltage down-converter 370, when turned on, converts the nominal DC output voltage of the battery 340 to a higher level to enable high output voltage compliance for electrical stimulation. In more detail, the electrical stimulation pulses for the stimulation therapy may require higher voltages (e.g., as high as 12 volts) than the nominal DC voltage output of the battery 340. In these cases, the voltage up-converter 370 may be activated to boost the DC output voltage of the battery 340, for example from 4 volts to 8 volts or 12 volts, or at a fractional value in between. In the illustrated embodiment, the voltage up-converter 370 supplies power to stimulation circuitry (e.g., stimulation driver) that will be discussed below in more detail. To accomplish the voltage boost, the voltage up-converter 370 includes a charge pump in the present embodiment, but it is understood that it may include alternative types of voltage up-converters in alternative embodiments.

It is understood that the specific voltage values here are provided merely as an example and are not intended to be limiting. For example, the voltage down-converter 360 may down-convert a 4 volt DC output of the battery 340 to a 2.3 volt DC voltage that will then be supplied to certain electronic circuitry of the PNS device 200. As another example, the voltage up-converter 370 may up-convert a 4 volt DC output of the battery 340 to a number that is a fraction (greater than 1) of the 4 volt DC voltage.

The stimulation circuitry section 305 includes a microprocessor or microcontroller 400 (referred to as a microcontroller hereinafter) that is powered by the output of the voltage down-converter 360. The microcontroller 400 controls various operations of the PNS device 200. For example, the microcontroller 400 is configured to generate electrical stimulation pulses in response to programming instructions received from a programmer, such as from the electronic programmer 250 discussed above with reference to FIGS. 6A-6C. In various embodiments, the microcontroller 400 may include a microcontroller chip (e.g., an applications processor) with internal instruction and data caches, multimedia capabilities, external memory interfacing, and interfacing flexibility.

The microcontroller 400 may also include memory such as FLASH memory, a read-only memory ("ROM"), a random access memory ("RAM"), an electrically erasable programmable read-only memory ("EEPROM"), a hard disk, an optical disk, or another suitable magnetic, optical, physical, or electronic memory device. In some embodiments, the microcontroller 400 includes a double data rate (DDR2) synchronous dynamic random access memory (SDRAM) for storing data relating to and captured during the operation of the portable electronic device 90. Of course, other types of data storage devices may be used in place of the data storage devices discussed herein. It is understood that the different types of memory discussed above may be integrated into the microcontroller chip discussed above or may be separately implemented from the microcontroller chip. Software code, firmware code, or other types of program modules and applications may be stored on the memory and may be executed to perform certain tasks, such as generating the stimulation pulses.

According to some embodiments, the microcontroller 400 is configured to perform one or more of the following tasks:
  Generate stimulation waveforms with internal 12-bit DAC, contact combinations, and manages compliance voltage
  Manage bidirectional telemetry & external communications
  Manage sensing for impedance, battery voltage, and physiological signals
  Store data for diagnostics and device use tracking
  Store Code, bootloader, and other suitable data in onboard FLASH and RAM
  Enter various power-conservation consumptions modes to reduce power consumption
  Manages emergency ON/OFF states from a magnetic switch
  Reconfigure system with a new firmware download As is shown in FIG. 7, the microcontroller 400 includes a microcontroller core 410. Most of the functions of the microcontroller 400 discussed above may be performed by, or at least in part by, the microcontroller core 410. As such, the microcontroller core 410 is a power-hungry device and consumes significantly more power than the rest of the components of the microcontroller 400. In order to save power, the microcontroller 400 also includes a direct memory access (DMA) unit 420. In some embodiments, the DMA unit 420 is a task handler that can operate independently from the microcontroller core 410. For example, the DMA unit 420 may be capable of sending instructions to peripherals (discussed in more detail below) within the microcontroller 400, without having to go through the microcontroller core 410. One benefit of using the DMA unit 420 is that it consumes substantially less power than the microcontroller core 410. For example, in some embodiments, the DMA unit 420 consumes less than 10% of the power of the microcontroller core 410. Therefore, according to various aspects of the present disclosure, the DMA unit 420 may be utilized to execute certain simple tasks while the microcontroller core 410 is turned off in order to reduce power consumption.

The microcontroller 400 further includes a plurality of peripherals, channels, or buses. For example, the microcontroller 400 may include a digital-to-analog converter (DAC) to generate the waveforms for the electrical stimulation pulses. The microcontroller 400 may also include an analog-to-digital converter (ADC) to convert an analog feedback signal to digital numbers. The microcontroller 400 may also include a VBOOST_EN line that is electrically coupled to the voltage up-converter 370. When the VBOOST_EN line is enabled, the voltage up-converter 370 is activated and doubles or triples the DC output voltage from the battery 340, or scales up the DC output voltage from the battery 340 by a fractional number greater than 1. In some embodiments, the VBOOST_EN line is only enabled to turn on the voltage up-converter 370 during the stimulation pulse. Between consecutive stimulation pulses, the VBOOST_EN line is disabled to turn off the voltage up-converter 370. In this manner, power consumption is reduced, since the voltage up-converter is not running all the time. The microcontroller 400 further includes an Input/Output (I/O) bus, a Serial-Peripheral-Interface (SPI) communication bus, and an Inter-Integrated-Circuit (I²C) communication bus, which allow the microcontroller 400 to communicate with peripherals or external devices.

Another peripheral-like device of the microcontroller 400 is a timer unit 425. The timer unit 425 includes hardware and firmware/software that control the timing for turning on and off the microcontroller core 410 and/or enabling/disabling the peripherals or other components of the PNS device 200. Although not illustrated herein for reasons of simplicity, the microcontroller 400 may also include one or more internal clocks. These internal clocks serve as timing sources for the timer unit 425.

In addition, a crystal oscillator 430 is external to the microcontroller 400 and is coupled to the microcontroller 400. In some embodiments, the crystal oscillator 430 generates a 32.678 Khz clock that may be used when the microcontroller 400 enters a power-conservation operating mode (also referred to as a low-power mode or a sleep mode) to reduce power consumption. The crystal oscillator 430 may also serve as a timing source for the timer unit 425.

In addition to the microcontroller 400, the stimulation circuitry 305 further includes a plurality of sensors that are electrically or communicatively coupled to the microcontroller 400. In the illustrated embodiment shown in FIG. 7, a magnetic sensor 435 is coupled to the microcontroller 400 through the I/O bus, and a temperature sensor 440 and an accelerometer 445 are each coupled to the microcontroller 400 through the I²C communication bus. In some embodiments, the magnetic sensor 435 may be used to turn on or off the PNS device 200, the temperature sensor 440 may be used to facilitate the energy harvested by the energy harvesting component 350, and the accelerometer 445 may be used to detect a posture of the patient, which may then be used to perform posture-dependent calibration. It is understood that these sensors 435-445 are merely examples, and that additional sensors such as pressure sensors, humidity sensors, vibration sensors, proximity sensors, light sensors, strain/stress sensors, transducers, gyroscopes, or compasses may be implemented in the PNS device 200 in various embodiments.

The stimulation circuitry section 305 further includes a stimulation driver 450 coupled to the DAC output of the microcontroller 400. The stimulation driver 450 includes amplification circuitry (e.g., op-amps) that is capable of amplifying an amplitude of the stimulation pulses generated by the DAC of the microcontroller 400. For example, in some embodiments, the stimulation driver 450 can amplify the amplitude of the stimulation pulses by a factor of 5. The amplification (or scaling up) of the variation stimulation waveforms (i.e., the stimulation pulses outputted by the DAC) obviates the need for a custom DAC.

The stimulation circuitry section 305 also includes stimulation multiplexers 460 that are coupled to the stimulation driver 450. The multiplexed stimulation outputs allow for configured stimulation contact combinations. In more detail, the stimulation multiplexers 460 serve as an array (e.g., 16 for anodes and 16 for cathodes) of switches that coupled to a plurality of stimulation channels through DC-blocking capacitors 465, respectively. The switches are coupled in parallel to one another. Through the turning on and off of these switches, electrical stimulation pulses can be delivered to the desired stimulation channel(s).

To help conserve energy, the stimulation driver 450 and the stimulation multiplexers are powered by either the battery 340 directly, or by the voltage output produced by the voltage up-converter 370, but not both. For example, when the stimulation pulse amplitude is less than what the battery 340 is capable of providing (e.g., stimulation voltage is at 3 volts, and the battery 340 outputs 4 volts), the voltage up-converter 370 need not be turned on, because the voltage up-converter 370 would consume power when it is turned on. The voltage up-converter 370 is turned on when the stimulation pulse demands a greater amplitude than the battery 340 is capable of providing. In this manner, the voltage up-converter 370 is selectively turned on or off to minimize power consumption. Thus, the output of the voltage up-converter 370 serves as the power supply for the stimulation driver 450 and the stimulation multiplexers 460 when needed, and the battery 340 serves as the power supply the rest of the time.

To ensure such operation, the present disclosure implements a diode 470 coupled between the output of the battery 340 and the inputs of the stimulation driver 450 and the stimulation multiplexers 460. Another diode 475 is also implemented between the output of the voltage up-converter 370 and the inputs of the stimulation driver 450 and the stimulation multiplexer 460. These two diodes 470 and 475 are coupled in parallel with each other and serve as switches such that only one path is created between the power source (either the battery 340 or the voltage up-converter 370) and the stimulation driver 450 and the stimulation multiplexer 460. When the voltage up-converter 370 is turned on, the diode 475 is forward-biased to create a charging path from the voltage up-converter 370 and the stimulation driver 450 and the stimulation multiplexers 460, while the diode 470 is reverse-biased to block the path from the battery 340 to the stimulation driver 450 and the stimulation multiplexers 460. This also ensures that the voltage up-converter 370 will not inadvertently charge the battery 340. When the voltage up-converter 370 is turned off, the diode 470 is forward-biased to create a charging path from the battery 340 and the stimulation driver 450 and the stimulation multiplexers 460, while the diode 475 is reverse-biased to block the path from the voltage up-converter 370 to the stimulation driver 450 and the stimulation multiplexers 460.

The stimulation circuitry section 305 further includes a switch 480 that is coupled between the output of the voltage up-converter 370 and the inputs of the stimulation driver 450 and the stimulation multiplexers 460. The switch 480 is also coupled to the microcontroller 400. In response to instructions from the microcontroller 400, this switch 480 may disconnect any load (e.g., the stimulation driver 450 and the stimulation multiplexers 460) from the voltage up-converter 370 between consecutive stimulation pulses, thereby preserving energy stored in the voltage up-converter 370 for the next stimulation pulse.

The stimulation circuitry section 305 may also include a sense amplifier 490 coupled between the output of the stimulation multiplexers and the microcontroller 400. In certain embodiments, the sense amplifier 490 is configured to sense action potentials of a target nerve. The sensed action potentials are fed back to the microcontroller for further processing and analysis. In some embodiments, the sense amplifier 490 can also measure impedance values.

The telemetry circuitry section 310 includes a telemetry block 500. The telemetry block 500 is powered by the voltage down-converter 360. The telemetry block 500 is also electrically and communicatively coupled to the microcontroller 400. The telemetry block 500 includes one or more transmitters, receivers, and/or transceiver. For example, the telemetry block 500 may include one or more of the following: a Medical Implant Communication Services (MICS) transceiver, an Industrial, Scientific and Medical (ISM) transceiver, a Wi-Fi transceiver, a Bluetooth transceiver, DLNA, or any of the 3G or 4G cellular networking transceivers. Through the telemetry block 500, the PNS device 200 may conduct bi-directional telecommunications with external devices, for example turning on/off the PNS device 200, receiving commands or programming instructions from the electronic programmer 250 discussed above, or transfer diagnostic data or unique patient information to the electronic programmer 250 or to a remote server.

The telemetry circuitry section 310 further includes an antenna 510 for transmitting and receiving telemetry signals. In some embodiments, the antenna 510 and the inductive charging component 320 may be the same component. In other words, a single conductive component such as a loop coil or wire may be used to charge the PNS device 200 and to conduct telecommunications with the PNS device 200.

For example, the antenna 510 may receive telemetry signals that are in different radio bands, such as signals in a MICS band (between 402 Mhz and 405 Mhz, which may hereinafter be referred to as a 400 Mhz MICS band) and signals in a 2.45 Ghz ISM band (between 2.4 Ghz and 2.5 Ghz). The telemetry signals in the 2.45 Ghz band may be used to "wake up" the PNS device 200, which is normally in a deep "sleep" mode, where little power is being consumed. After the PNS device 200 is "woken up," the telemetry signals in the MICS band are used to conduct telecommunications between the PNS device 200 and external devices such as the electronic programmer 250. Since the PNS device 200 employs a single antenna 510 to receive multiple types of telemetry signals, these different types of telemetry signals need to be properly discriminated, otherwise one type of telemetry signals may cause interference or create noise for the other type of telemetry signals.

According to the various aspects of the present disclosure, the telemetry circuitry section 310 includes a plurality of circuits or circuit networks to discriminate different types of input signals received from the antenna 510. In the illustrated embodiment, circuit networks 520 and 530 are implemented in the telemetry circuitry section 310. The circuit network 520 includes microelectronic components that will allow the telemetry signals in the MICS radio band to pass through but will reject signals outside the MICS radio band, including the telemetry signals in other bands (e.g., telemetry signals in the 2.45 Ghz band) and charging signals (e.g., charging signals in the 13.56 Mhz ISM band). The circuit network 530 includes microelectronic components that will allow the telemetry signals in the 2.45 Ghz radio band to pass through but will reject signals outside the 2.45 Ghz radio band, including the telemetry signals in other bands (e.g., telemetry signals in the 400 Mhz MICS band) and charging signals (e.g., charging signals in the 13.56 Mhz ISM band). In this manner, the circuit networks 520 and 530 provide discrimination for the input signals.

It is understood that although the circuit network 325 is not a part of the telemetry circuitry section 310, it also helps provide discrimination of the input signals. As discussed above, the antenna 510 and the inductive charging component 320 may be the same conductive component, for example, a single turn wire or coil. In other words, the same wire or coil may be used to receive both charging signals (e.g., inductive energy in the 13.56 Mhz ISM band) and telemetry signals in the 400 Mhz MICS band and telemetry signals in the 2.45 Ghz band. Thus, the circuit network 530 includes microelectronic components that will allow the charging signals in the 13.56 Mhz ISM band to pass through but will reject signals outside the 13.56 Mhz ISM band, including the telemetry signals in the 400 Mhz MICS band and in the 2.45 Ghz ISM band.

The circuit networks 520 and 530 may also each include passive components such as inductors and capacitors for impedance matching. Impedance matching may maximize power transfer or may reduce signal reflection (for example, reflection from a load). In the illustrated embodiment, the circuit networks 520 may include passive circuit elements collectively arranged to match the impedances of the telemetry block 500 and the antenna 510 in the 400 Mhz MICS band. In some embodiments, the circuit network 530 may also include passive circuit elements collectively arranged to match the impedances of the telemetry block 500 and the antenna 510 in the 2.45 Ghz frequency band.

FIGS. 8A-8L are detailed circuit schematics of the PNS device 200 according to an embodiment of the present disclosure. However, it is understood that the PNS device 200 may be implemented differently in alternative embodiments and is not limited to the specific implementation shown in FIGS. 8A-8L.

Paddle Lead Maximizing Lateral Target Points Across a Peripheral Nerve

Figure 9:
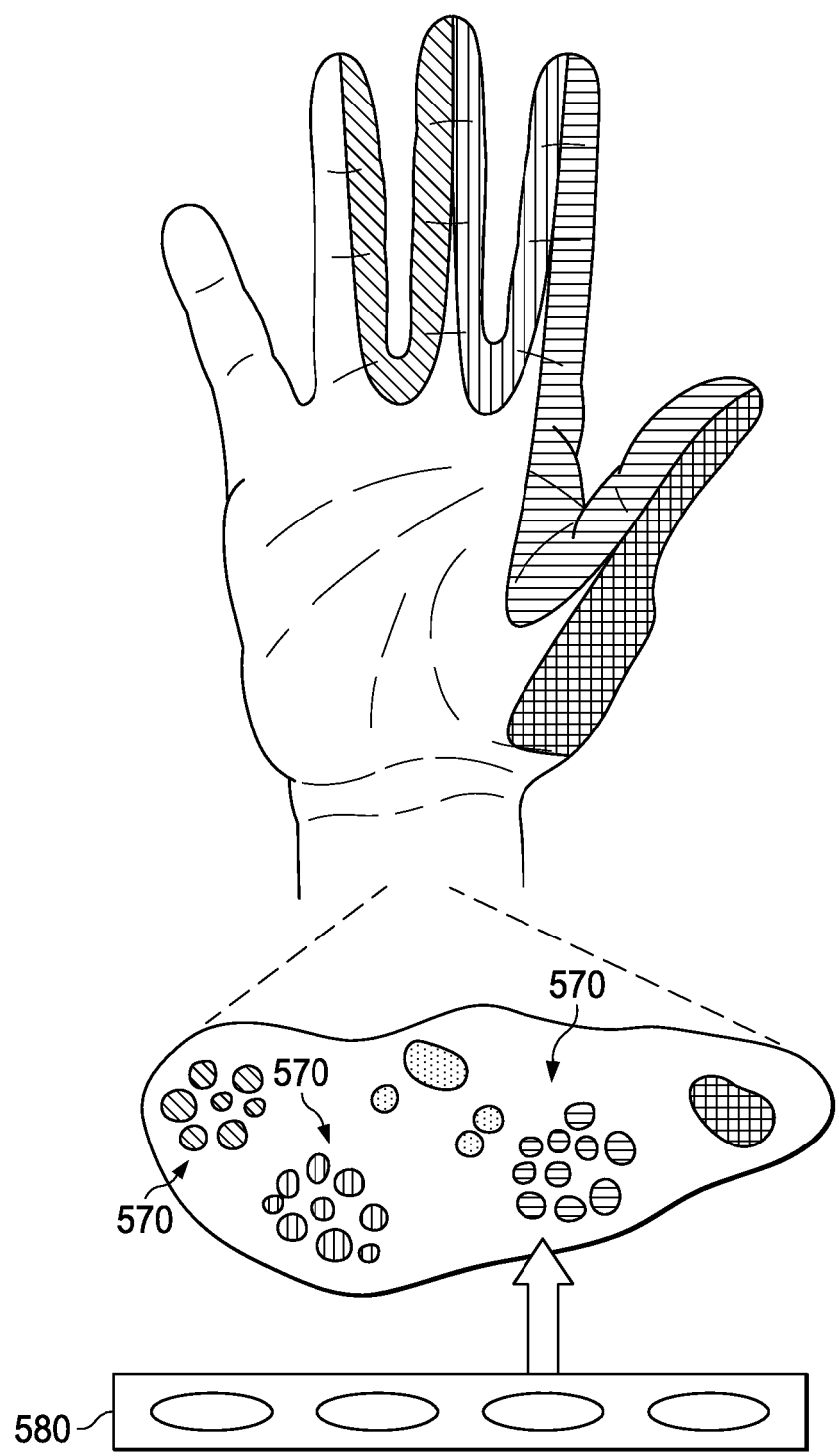
FIG. 9 illustrates example peripheral nerve bundles being stimulated by a paddle lead according to an embodiment of the present disclosure.

As discussed above, unlike spinal cord stimulation devices, the PNS device 200 is specifically configured to deliver electrical stimulation for peripheral nerves. Referring to FIG. 9, peripheral nerves comprise 'bundles' (e.g., bundles 570) of groupings of axons called fascicles. Typically, a fascicle innervates a particular area or region of the body. Additionally, some fascicles carry a predominance of efferent motor fibers while others carry mostly afferent sensory fibers.

Depending upon the therapeutic application at hand, peripheral nerve stimulation systems typically seek to activate only motor nerves (e.g., for functional purposes, such as dorsiflexion for a dropped foot, or a grasp for upper extremity hemiplegia), or only sensory nerves (e.g., for neuropathic pain management). In any particular application, neural selectivity is usually achieved by maximally activating the targeted fascicles while avoiding activation of those fascicles that may lead to side effects (e.g., in pain management, stimulation of motor nerves can limit the efficacy of the therapy that is to be provided).

One method of peripheral nerve stimulation uses paddle leads, a simplified example of which is shown as a lead 580 in FIG. 9. Concerted effort is required to place paddles at least near or over the targeted fascicles, but this can usually be achieved intraoperatively in a nominal amount of time.

One challenge with paddle leads in peripheral nerve stimulation is the need to provide contacts or electrodes in the paddle lead that are of a certain size or surface area so that charge density concerns can be managed, which include avoiding the creation of toxic electrochemical products generated by stimulation currents at the contact or electrode location, or associated with contact corrosion. Typical paddle electrodes or contacts are rectangular with a nominal surface area. The contact width necessary to maintain current flow below charge density limits is such that the ability to provide fine fascicular targeting becomes limited, in part because contacts can only be placed on a paddle lead such that they do not electrically short together during manufacture or implantation. What is needed includes a paddle lead configured to maximize transverse fascicular targeting or selectivity in a peripheral nerve, or a paddle lead that permits fine separation of fascicles in a targeted nerve.

Figure 10:
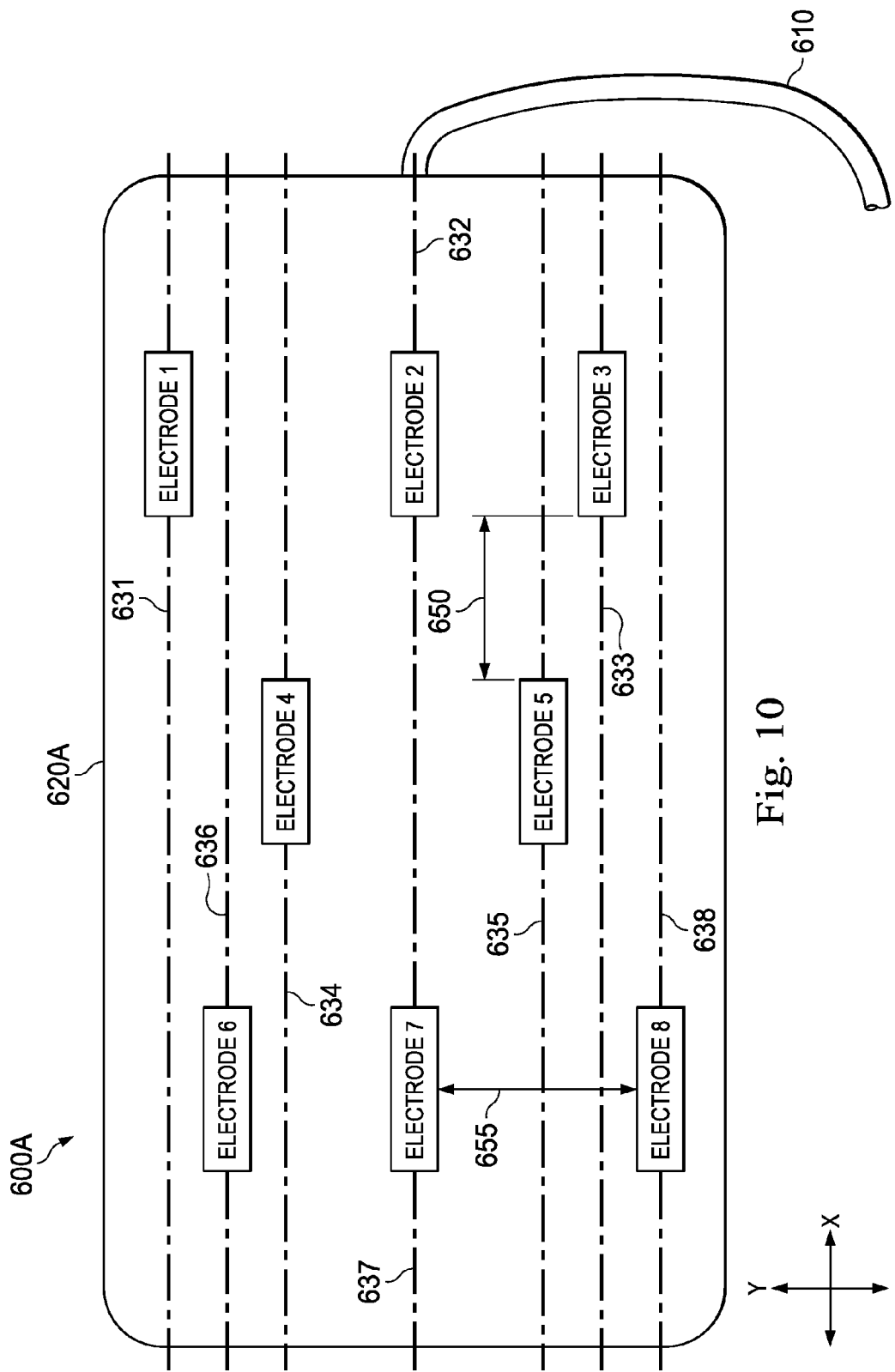
FIGS. 10-14 illustrate example paddle leads for delivering electrical stimulation to peripheral nerve according to various embodiments of the present disclosure.

Referring now to FIG. 10, a simplified diagrammatic view of an example implantable lead 600A of the present disclosure is illustrated according to an embodiment. The implantable lead is configured to be coupled or attached to the PNS device 200 discussed above. The implantable lead 600A delivers electrical stimulation pulses generated by the stimulation circuitry 305 of the PNS device 200 to target peripheral nerves. The implantable lead 600A includes an elongate flexible/bendable lead body 610 that includes a coupling assembly (not specifically illustrated herein), which is configured to be coupled to the PNS device 200. The implantable lead 600A also includes a paddle 620A that includes a plurality of electrodes (also referred to as contacts), for example electrodes 1-8 as shown in FIG. 10. Electrical stimulation pulses are delivered to the target peripheral nerve through these electrodes.

According to various aspects of the present disclosure, the electrodes 1-8 are collectively arranged in a manner such that they provide a plurality of unique centerlines 631-638. For example, the paddle lead 600A includes a plurality of rows of electrodes oriented along its length such that the respective centerline of the electrode(s) on each row is mostly or completely different from those on other rows. In the illustrated embodiment, the centerlines 631-638 extend in an X-direction or along an X-axis, whereas the fascicles of the target peripheral nerve typically extend in a Y-direction or along a Y-axis (perpendicular to the X-axis). In general, it is desired to try to keep the centerlines of the electrodes in the middle of the targeted nerves, as it offers redundancy and flexibility to recover/restore stimulation in spite of slight movements of the nerve or electrode.

Most conventional paddle leads typically employ a grid approach for its electrodes, where the electrodes are neatly arranged into rows and columns, and where all the electrodes in the same row are aligned with one another (e.g., aligned along the X-axis), and all the electrodes in the same column are aligned with one another (e.g., aligned along the Y-axis). Consequently, conventional paddle leads can only offer a very limited number of unique centerlines. For example, a conventional paddle lead with 9 electrodes with a 3×3 configuration can only offer 3 unique centerlines. As discussed above, the centerlines are correlated with the associated electrode's ability to provide target stimulation. Thus, having a limited number of centerlines may prevent the PNS device from providing flexible stimulation therapies.

In comparison, the paddle 620A has a 3-2-3, 8-contact or electrode configuration in the embodiment illustrated in FIG. 10. As is shown in FIG. 10, the 8 electrodes are arranged to achieve 7 unique centerlines (electrodes 2 and 7 have substantially the same centerline) transversely disposed across the nerve over which it is placed. In other words, a substantial majority (7 out of 8) of the electrodes on the paddle 620A have their own respective unique centerlines. Alternatively stated, the electrodes 1-8 on the paddle 620 are "staggered." Such staggered 3-2-3 electrode arrangement of the paddle lead 600A permits fine separations of fascicles (or allows for greater fascicular selectivity) in a nerve to be targeted, because individual electrodes can be activated as cathodes on different rows to 'sweep' the stimulation field across the nerve to find the location that maximizes the desired therapeutic effect while minimizing side effects. In some embodiments, the electrodes 631-638 of the paddle lead 600A are configured to take into account the tendency of fascicles in peripheral nerves to run in a relatively fixed longitudinal course along the length of the nerve that is to be stimulated.

In addition, since the paddle lead 600A is configured for peripheral neural stimulation, the spacing between adjacent electrodes may be small too. In some embodiments, a distance 650 separating adjacent electrodes in the X-direction is in a range from about 1 millimeters (mm) to about 5 mm, and a distance 655 separating adjacent electrodes in the Y-direction is in a range from about 2 millimeters (mm) to about 5 mm. The distance 650 may also be referred to as a horizontal spacing, and the distance 655 may also be referred to as a vertical spacing.

These distances 650-655 are significantly smaller than the distances separating adjacent electrodes on a paddle lead configured to deliver spinal cord stimulation. This is because in the context of spinal cord stimulation, the paddle would be implanted near the spinal cord, which may span a great distance. Thus, the paddle lead for spinal cord stimulation is typically configured to have electrodes that are spaced farther apart, so that they can span a relatively long distance that may be required to reach the target stimulation site. It is not as important to achieve such fine resolution in the spinal cord stimulation context.

In comparison, peripheral nerve stimulation is typically focused in a relatively small area. In addition, as discussed above, peripheral nerve stimulators need to achieve high neural selectivity in the target nerve such that only the desired nerve fibers (for example, only the efferent fibers or only the afferent fibers) are activated but not the other. As such, peripheral nerve stimulators need to have smaller distances separating adjacent electrodes to allow for the high neural selectivity.

It is understood that the electrodes 631-638 may be substantially evenly or uniformly spaced apart in either the X-direction or the Y-direction (or both) in some embodiments, or they may be unevenly spaced apart in the X or Y-directions in other embodiments.

Figure 11:
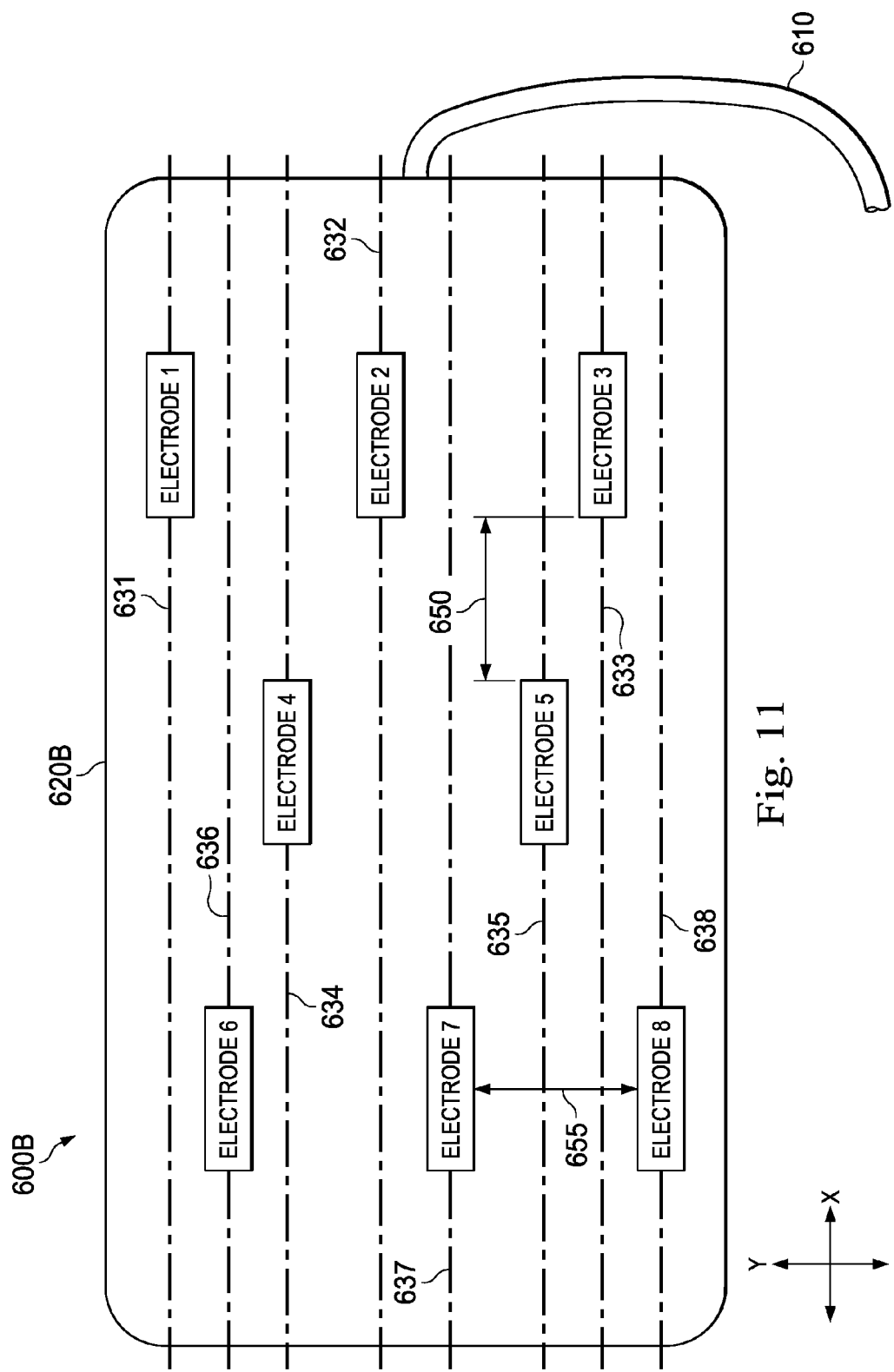

FIG. 11 illustrates a simplified diagrammatic view of an implantable lead 600B according to another embodiment of the present disclosure. The implantable 600B has a paddle 620B that is similar to the paddle 620A shown in FIG. 10. However, the electrodes 1-8 of the paddle 620B are arranged such that every electrode has a unique respective centerline that extends in the X-direction. In other words, the paddle 620B achieves a total of 8 unique centerlines with 8 electrodes, compared to the 7 centerlines achieved by the paddle 620A in FIG. 10.

In some embodiments, electrodes are not arranged in a grid per se, but are offset from one row to the next. In some embodiments, none of the electrodes in a single row on the paddle are arranged in a single column. For example, referring now to FIG. 12, a simplified diagrammatic view of an implantable lead 600C is illustrated according to another embodiment of the present disclosure. The implantable 600C has a paddle 620C that contains electrodes 1-9. The electrodes 1-9 are arranged in a staggered manner in both the X-direction and the Y-direction. In more detail, the electrodes 1-9 are roughly arranged into 3 "columns" 660, 661, and 662, and 3 "rows" 665, 666, and 667. The column 660 includes electrodes 1-3, the column 661 includes electrodes 4-6, and the column 662 includes electrodes 7-9. The row 665 includes electrodes 1, 4, and 7, the row 666 includes electrodes 2, 5, and 8, and the row 667 includes electrodes 3, 6, and 9.

However, the electrodes in each column are not aligned in the Y-direction, and the electrodes in each row are not aligned in the X-direction. Rather, the electrodes in each column are still offset from one another, as are the electrodes in each row. For example, the columns 660-662 may each extend in a direction 668 that is somewhat "vertical" but is not parallel to the X-axis or the Y-axis. In other words, the direction 668 has a greater Y-component than an X-component. The rows 665-667 may each extend in a direction 669 that is somewhat "horizontal" but is also not parallel to the X-axis or the Y-axis. In other words, the direction 669 has a greater X-component than a Y-component.

Since the directions in which the columns and rows extend are not parallel with the X or Y axes, the electrodes 1-9 offer unique vertical and horizontal centerlines. According to the embodiment of the paddle 620C shown in FIG. 12, the electrodes 1-9 have horizontal centerlines (i.e., centerlines spanning in the X-direction) 631-639, and the electrodes 1-9 have vertical centerlines (i.e., centerlines spanning in the Y-direction) 671-679. The electrodes 1-9 are staggered horizontally and vertically such that they collectively offer 9 unique horizontal centerlines 631-639, as well as 9 unique vertical centerlines 671-679.

As discussed above, having the plurality of unique horizontal and vertical centerlines 631-639 and 671-679 affords the paddle 620C the flexibility and versatility to selectively stimulate one or more target nerve fibers but not the undesired nerve fibers, even if the desired and undesired nerve fibers are closely located to one another. In other words, the staggered electrode arrangement discussed herein can achieve high neural selectivity, and the PNS system with the implantable lead 600C permits very precise spatial targeting of different portions of a nerve.

Figure 12:
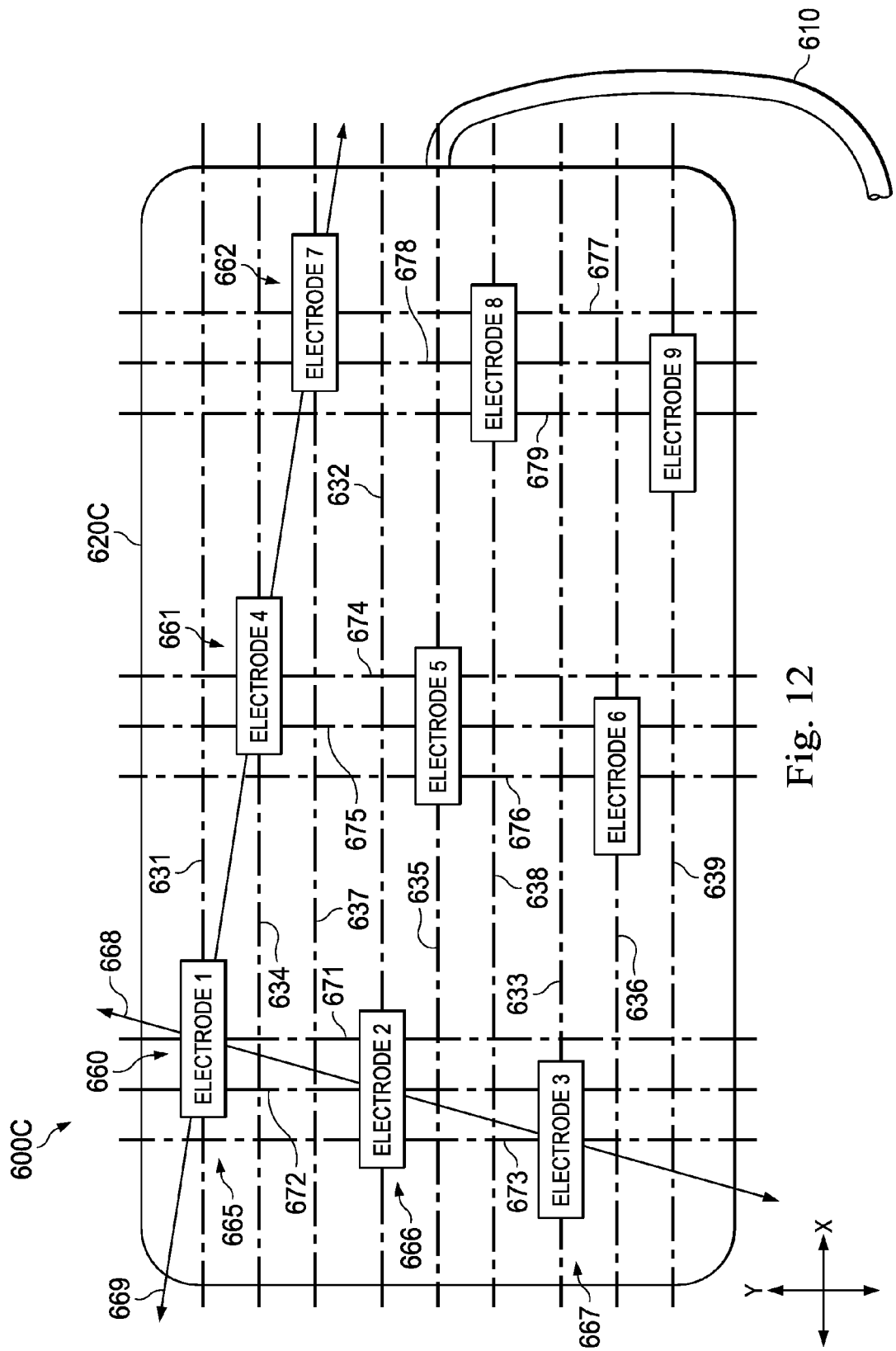
Figure 13:
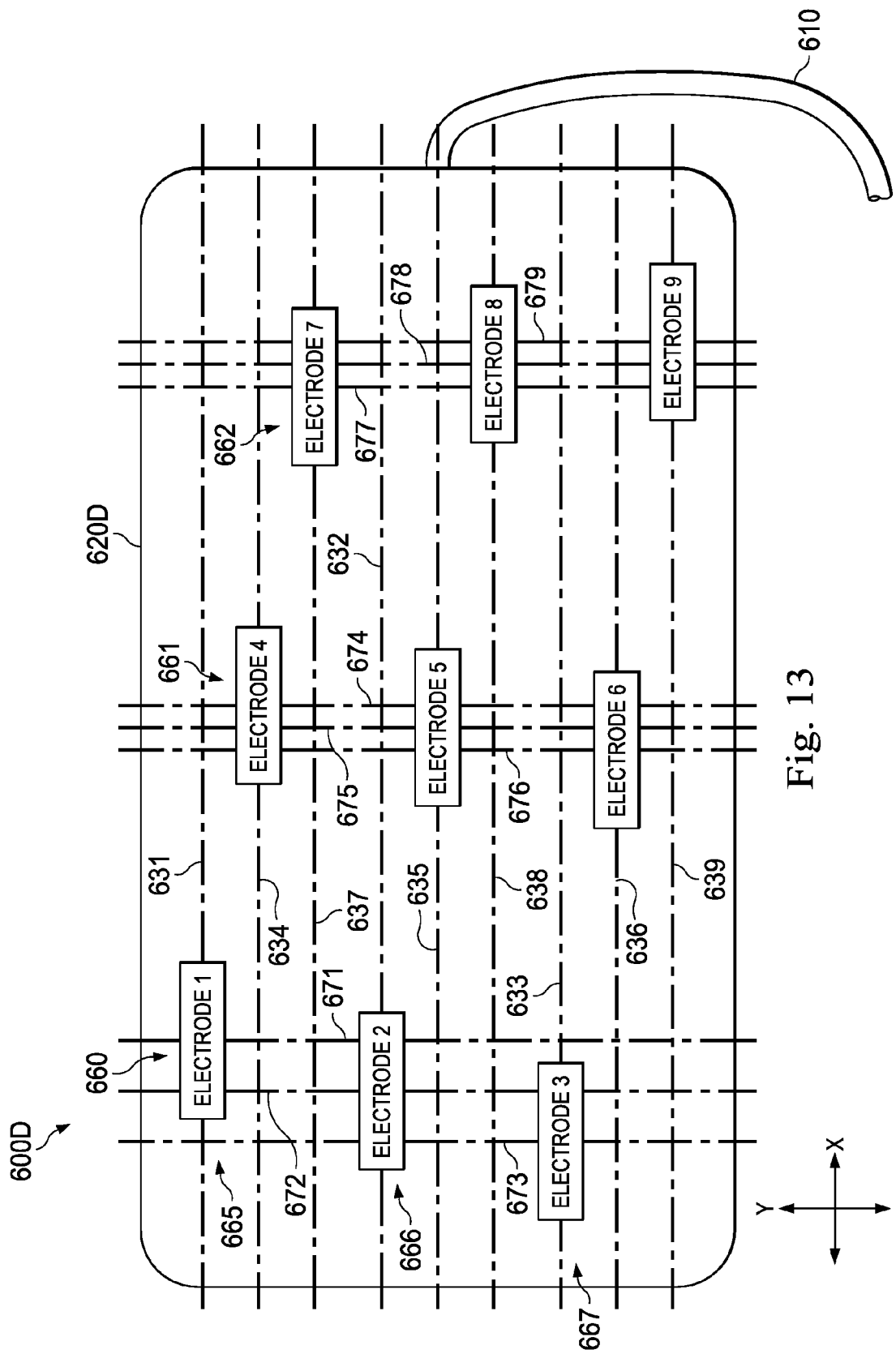

FIG. 13 illustrates a simplified diagrammatic view of an implantable lead 600D according to yet another embodiment of the present disclosure. The implantable lead 600D is similar to the implantable lead 600C shown in FIG. 12 in that it also offers an electrode arrangement that is both horizontally staggered and vertically staggered. However, the electrodes 1-9 on the paddle 620D are even more staggered. For example, the horizontal and vertical distances separating adjacent electrodes may be uneven or non-uniform. As another example, there may not be any linear direction in which any of the "columns" 660-662 or the "rows" 665-667 extend, let alone a direction that is parallel to either the X-axis or the Y-axis. In some embodiments, even if some of the "columns" or "rows" extend along a particular linear direction, such linear direction would not be parallel with any linear direction of any other "column" or "row." Stated differently, none of the "columns" 660-662 is parallel with any other of the columns on the paddle 620D, and none of the "rows" 665-667 is parallel with any other of the rows on the paddle 620D. The horizontal centerlines 631-639 are still each unique, as are the vertical centerlines 670-679. Again, such staggered electrode arrangement may permit good neural selectivity.

Figure 14:
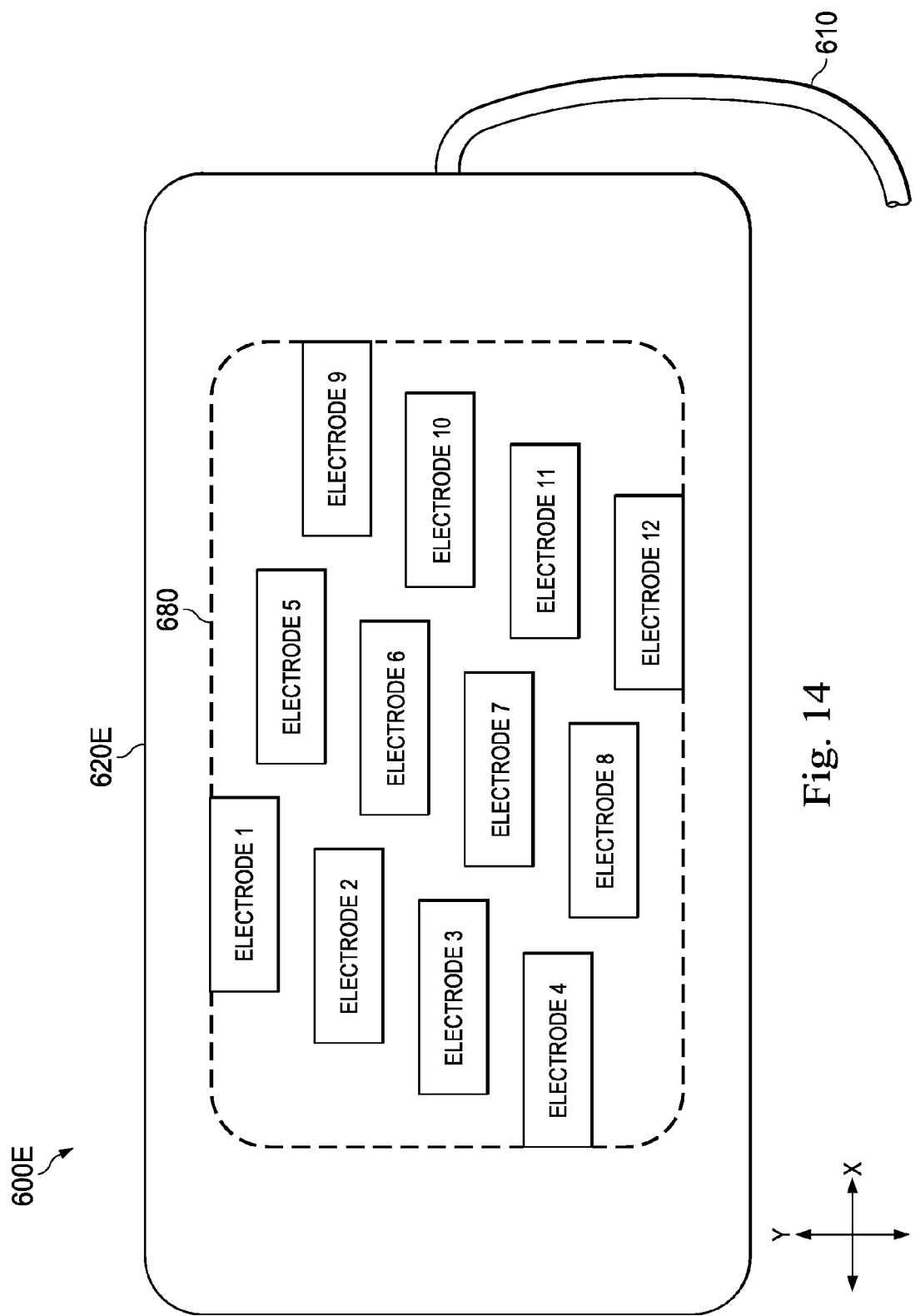

FIG. 14 illustrates a simplified diagrammatic view of an implantable lead 600E according to yet another embodiment of the present disclosure. Here, the implantable lead 600E includes a paddle 620E that has 12 electrodes implemented thereon. The 12 electrodes are collectively arranged in roughly 3 "columns" and 4 "rows" and collectively define a stimulation region 680 on the paddle 620E. The boundaries or outlines of stimulation region 680 may be defined by a topmost edge of a topmost electrode (electrode 1 in this case), a bottommost edge of a bottommost electrode (electrode 12 in this case), a leftmost edge of a leftmost electrode (electrode 4 in this case), and a rightmost edge of a rightmost electrode (electrode 9 in this case). As such, the stimulation region 680 has approximately a rectangular shape. However, it is understood that the outlines or boundaries of the stimulation region 680 may not be actually visible on the paddle 620E.

The electrodes 1-12 are staggered to the extent such that no horizontal linear paths (or a straight line parallel to the X-axis) or vertical linear paths (or a straight line parallel to the Y-axis) across the stimulation region 680 may exist without intersecting at least one of the electrodes 1-12. Stated differently, within the stimulation region 680, every horizontal linear path and every vertical linear path will intersect at least one of the electrodes 1-12. This is due to the partial overlap in both the X-and-Y-directions among the electrodes 1-12. For example, electrodes 1 and 5 are overlapped in the Y-direction, as are electrodes 5 and 9, as are electrodes 9 and 2, as are electrodes 2 and 6, so on and so forth. Similarly, electrodes 4 and 3 are overlapped in the X-direction, as are electrodes 3 and 2, as are electrodes 2 and 1, as are electrodes 1 and 8, so on and so forth. Therefore, if a horizontal or vertical linear path is to extend across the entire stimulation region 680, one or more of the electrodes 1-12 will necessarily be in its path. It may be said that the staggered electrode arrangement of the paddle 620E completely blocks all horizontal and linear paths across the stimulation region 680. As such, the staggered electrode arrangement of the paddle 680 may theoretically permit electrical stimulation in almost every target nerve site covered by the stimulation region 680, thereby imparting a high degree of adjustability and targetability of delivered electrical stimulus.

It is understood that in some embodiments, such as the embodiment of the paddle 620C shown in FIG. 12, there may be some horizontal or vertical linear paths that may extend across the entire stimulation region 680 without intersecting at least one of the electrodes. However, even in such embodiments, a substantial majority (e.g., greater than 70%, 80%, or 90% in various implementations) of the available horizontal and vertical linear paths may still intersect with at least one electrode, because there is still some amount of horizontal or vertical overlap among the electrodes 1-9 on the paddle 620C. Therefore, it may be said that in these embodiments (e.g., embodiment shown in FIG. 12), the staggered electrode arrangement blocks a substantial majority of the horizontal and linear paths across the stimulation region. Even in these embodiments, however, the amount of overlap (in the X or Y directions) among the electrodes may still offer a high degree of adjustability and targetability of delivered electrical stimulus.

In each of the embodiments of the paddle lead 600 shown in FIGS. 10-14 and discussed above, there are at least 3 "rows" and/or 3 "columns" of electrodes. In other embodiments, any other number of columns or rows greater than 3 may be implemented for the paddle with staggered electrodes. The greater number of rows or columns allows the paddle to be better suited for peripheral nerve stimulation, as the peripheral nerves may have irregular shapes and may span in various directions. In comparison, many conventional paddle leads only have 1 or 2 columns of electrodes. This is adequate for spinal cord stimulation, since the target nerves in the SCS context extend along the spine, which is mostly straight and narrow. However, these SCS paddle leads with 1 or 2 columns of electrodes will not work very well in the peripheral nerve stimulation context, since the 1 or 2 columns of electrodes may not be able to reach all the target stimulation areas, and maintain targeted stimulation over desired regions, due to the geometric differences between the spinal cord and the peripheral nerves, primarily the tortuous winding nature of peripheral nerves within their neurovascular bundles. For these reasons, the various embodiments of the implantable lead 600 discussed herein are specifically configured to have 3 or more columns or rows of electrodes, which are also arranged in a staggered formation, in order to provide better a peripheral stimulation therapy. Further, the staggered electrode arrangements shown in FIGS. 10-14 allow for formations of a plurality of different "stimulation paths" between the various electrodes on the lead. These "stimulation paths" between the electrodes extend in a variety of directions due to the electrodes being staggered, whereas the conventional neatly-arranged rows and columns of electrodes may allow for much fewer "stimulation paths" that extend in different direction. Also due to the staggered electrodes herein, various "stimulation paths" may be created to generate electric fields that can be flexibly shaped. Therefore, the ability of the paddle lead herein to establish these "stimulation paths" allows for more versatile and flexible stimulation zones and steering of stimulation over small and larger target regions, which as discussed above is a unique concern of peripheral stimulation that does not exist in the spinal cord stimulation context.

Circuit for Discriminating Between Battery
Charging Signals and RF Telemetry Signals
Received by a Single Coil in an Implantable
Medical Device As discussed above, another one of the unique aspects of the present disclosure is that it utilizes a single conductive element (e.g., coil) to receive different types of charging and telemetry signals and utilizes various circuit elements to provide discrimination for these different types of signals. This aspect of the present disclosure is now discussed in greater detail below.

Figure 15C:
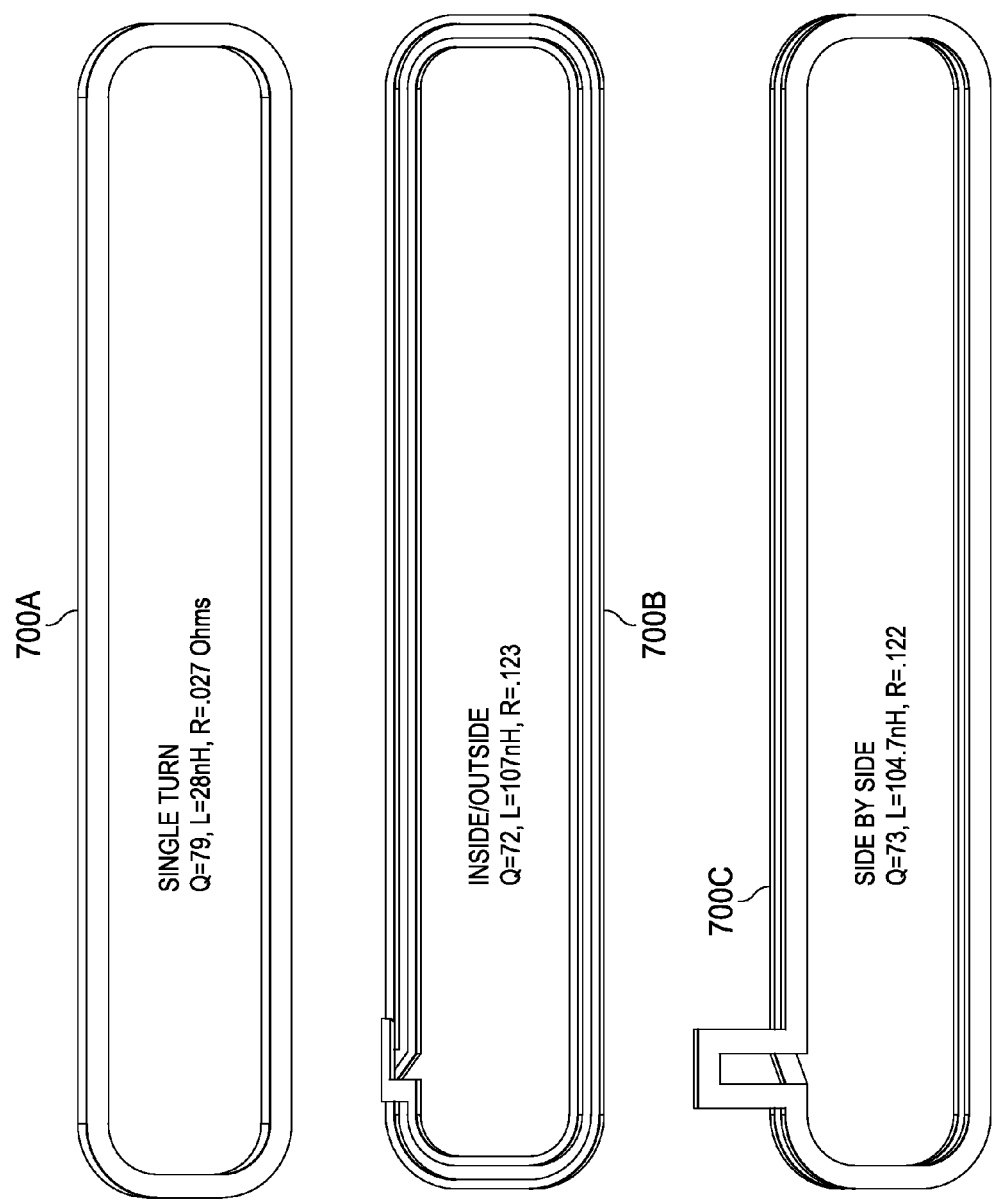

FIGS. 15A-15C provide various illustrations of a coil 700 that is an embodiment of the inductive charging component 320 and the antenna 510 shown in the block diagram of FIG. 7. In other words, the coil 700 can be used to receive both inductive charging signals (e.g., at the 13.56 Mhz ISM band) and telemetry signals (e.g., at the 400 Mhz MICS band and at the 2.45 Ghz ISM band). In more detail, FIG. 15A illustrates the disposition of the coil 700 in an embodiment of the PNS device 200, FIG. 15B illustrates the coil 700 by itself, and FIG. 15C shows top views of a few different embodiments of the coil as coil 700A, 700B, and 700C.

The coil 700 shown in FIGS. 15A and 15B in FIG. 15C are each a single turn piece of wire having an approximately rectangular shape with rounded corners. The embodiment of the coil 700B shown in FIG. 15C includes an inside turn and an outside turn and thus has a slightly different Q factor, inductance, and resistance compared to the single turn embodiment of the coil 700A. The embodiment of the coil 700C shown in FIG. 15C includes two side-by-side turns and thus also has a slightly different Q factor, inductance, and resistance compared to the single turn embodiment of the coil 700A or compared to the inside/outside turn embodiment of the coil 700B. As shown in FIG. 15A, the coil 700 is implemented outside of a hermetically-sealed housing or enclosure (also referred to as a can) 710 of the PNS device 200. Most of the circuitry discussed above with reference to FIG. 7 are implemented within the hermetically-sealed housing 710, including but not limited to, the battery 340, the voltage down-converter 360 and the voltage up-converter 370, the microcontroller 400, the sensors 435-445, the stimulation driver 450, the stimulation multiplexers 460, the telemetry chip 500, the circuit networks 325, 520, 530, etc.

It is understood that in these embodiments, the coil 700 is optimized to receive signals at the 13.56 Mhz band, the 400 Mhz band, and the 2.45 Ghz band, since these bands are employed to carry out the inductive charging and telecommunications of the present embodiment of the PNS device 200. However, in alternative embodiments where the PNS device may utilize different frequency bands to conduct charging and telecommunications, the coil may be optimized differently for those bands as well.

Conventionally, neurostimulators use an antenna to receive telemetry signals and a separate charging coil to receive inductive charging signals. The antenna is typically located outside a hermetically-sealed housing (e.g., made of metal or a metal alloy) for the pulse generator, which contains most of the circuitry such as charging circuitry, stimulation circuitry, and telemetry circuitry. The placement of the antenna outside the housing is for better signal reception. The charging coil is typically located inside the hermetically-sealed housing because traditional charging signals are limited at very low frequencies (e.g., 40 Khz-80 Khz), which can penetrate through metal relatively easily. However, the low charging frequencies are associated with a lower quality factor (Q), which leads to charging inefficiencies. The low charging frequencies also require the charging coil to have many turns (e.g., 50 turns or more), which consumes a lot of space. In other words, the implementation of a signal antenna outside the housing and a separate charging coil inside the housing results in bigger, more cumbersome neurostimulation device that may have inadequate charging performance.

In comparison, a single conductive element such as the coil 700 is used to receive both telemetry signals and charging signals. The coil 700 and the corresponding circuitry inside the PNS device 200 are configured to receive charging signals at a much higher frequency (e.g., 13.56 Mhz) than the low charging frequencies for conventional neurostimulators. As such, the coil 700 can have a much higher Q than the charging coils for conventional neurostimulators. The higher Q results in better charging efficiency and quicker charging time. In addition, since the charging frequency is higher, a single turn is sufficient for the coil 700, and it can be implemented outside the hermetically-sealed housing. Furthermore, the implementation of the coil 700 outside the housing reduces heating effects, and it may allow less expensive materials to be used for the housing. In some embodiments, MRI compatibility can also be enhanced, for instance, by providing no ferrite core. The material used for the single-turn coil 700 may also result in low resistance. The size of the coil 700 (e.g., due to using only a single turn wire) can also be much smaller than the charging coil for conventional neurostimulators.

For these reasons discussed above, the design of using a single coil for both telemetry and charging allows the PNS device 200 to be made small, cheap, and have improved performance over conventional neurostimulators. However, since a single coil 700 is used for both telemetry and charging, the PNS device 200 needs to be able to discriminate the telemetry and charging signals, so that they do not cause interference for one another, as discussed below.

Figure 16:
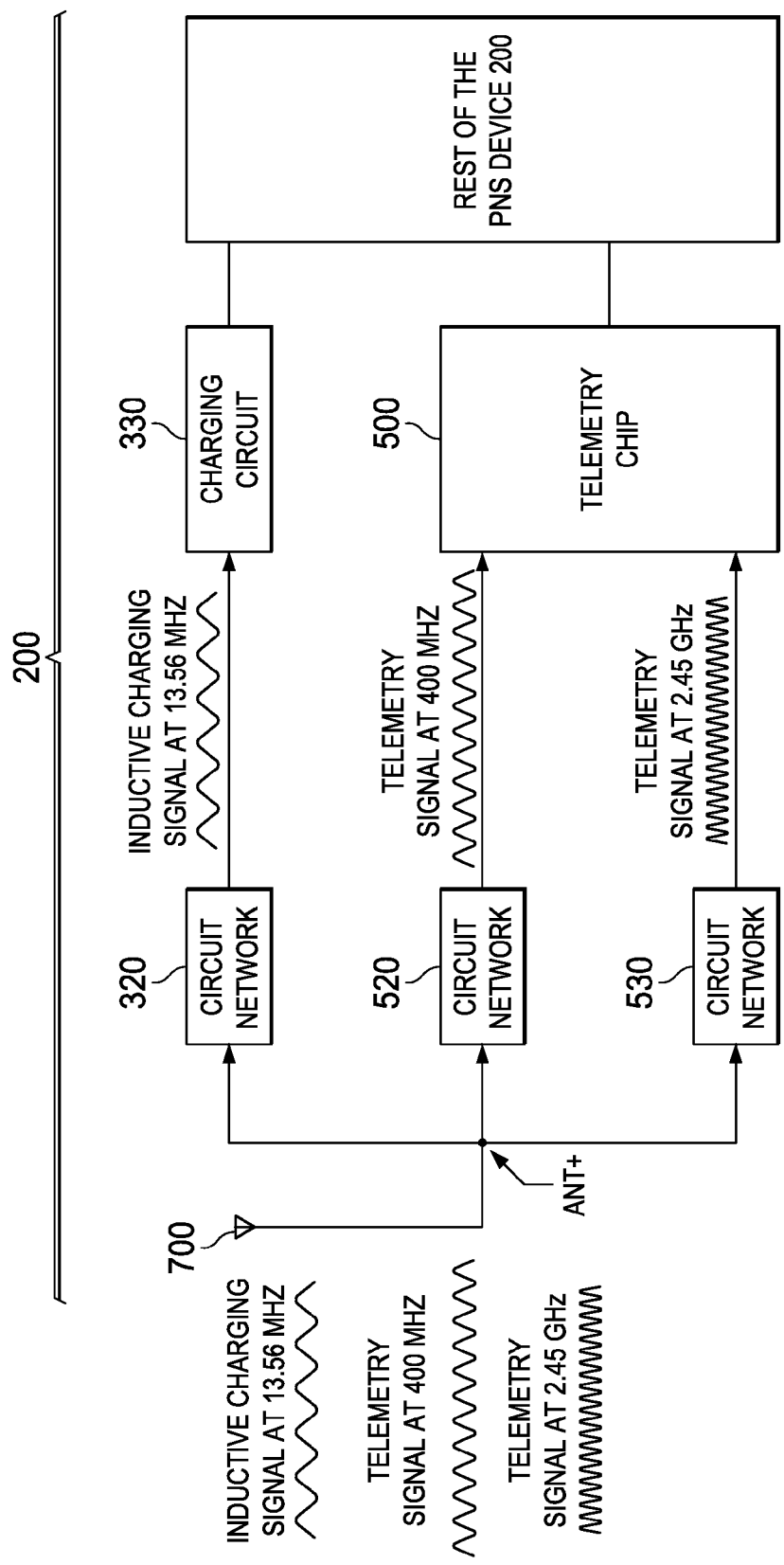
FIG. 16 illustrates a simplified block diagram of components of the peripheral neurostimulator used to provide signal discrimination according to various embodiments of the present disclosure.

FIG. 16 is a simplified block diagram of the various components and devices of the PNS device 200 that provide signal discrimination for the different types of signals received by a single antenna. Again, it is understood that in the illustrated embodiment, the inductive charging component 320 and the antenna 510 shown in the block diagram of FIG. 7 are integrated together as a single coil 700. The coil 700 is electrically coupled to the circuit networks 320, 520, and 530, each of which is discussed above with reference to FIG. 7. It can be seen that the circuit networks 320, 520, and 530 are electrically coupled in parallel. As such, the networks 320, 520, and 530 provide parallel signal paths for different types of signals.

The circuit network 320 is coupled to the charging circuit 330 (also discussed above with reference to FIG. 7) and allows inductive charging signals at the 13.56 Mhz band to pass through to the charging circuit 330 by way of resonant network elements. In some embodiments, the circuit network 320 includes a resonant network that generates a high Q at the resonant frequency, where the resonant frequency is tuned to be substantially equal to the frequency of the charging signal (e.g., at 13.56 Mhz). As such, the reception of signals is maximized at the charging frequency, thereby allowing the charging signal to pass through with minimal attenuation. Meanwhile, although the resonant network is not specifically configured to filter out signals from the 400 Mhz or the 2.45 Ghz bands, the reception of the signals outside the resonant frequency is not maximized due to the resonant frequency being at or substantially near the 13.56 Mhz. Thus, the resonant network of the circuit network 320 may effectively function as a very narrow band-pass filter to "block" signals that are outside of the 13.56 Mhz band. As such, to the extent that the 400 Mhz and the 2.45 Ghz telemetry signals are received by the network 320, they will be substantially attenuated by the time they reach the charging circuit 330.

Meanwhile, the circuit networks 520 and 530 are each coupled to a telemetry chip 500 that is an embodiment of the telemetry block 500 (also discussed above with reference to FIG. 7). Using filters such as a band-pass filter and a high-pass filter, the circuit network 520 allows telemetry signals at the 400 Mhz MICS band to pass through to the telemetry chip 500, but blocks out telemetry signals at other frequency bands (e.g., signals at the 2.45 Ghz ISM band) and inductive charging signals (e.g., signals at the 13.56 Mhz band). Similarly, using filters such as a high-pass filter, the circuit network 530 allows telemetry signals at the 2.45 Ghz ISM band to pass through to the telemetry chip 500, but blocks out telemetry signals at other frequency bands (e.g., signals at the 400 Mhz MICS band) and inductive charging signals (e.g., signals at the 13.56 Mhz band). Additionally, the circuit network 520 and/or the circuit network 530 may include additional passive circuit elements such as inductors and/or capacitors for impedance matching, so as to maximize power transfer or to reduce signal reflection, etc. The filtering out of the undesired signals will minimize the interference that these undesired signals may cause to the desired signals.

Again, it is understood that the frequency bands used herein are merely examples. In other embodiments, the same approach shown in FIG. 16 may be used to provide discrimination of other types of inductive charging signals and telemetry signals that may be collectively received by the same antenna or coil. It is also understood that in a real world implementation, it may not be possible to completely block or filter out signals from an undesired frequency band. Thus, in the context of the present disclosure, "signal blocking", "signal filtering", or other similar phrases may mean that the undesired signals are substantially attenuated to the point where they no longer cause any meaningful interference. In other words, even if some portions of the undesired signals may get through one of the circuit networks 320, 520, and 530 discussed above, they may be negligible because their amplitudes are sufficiently small. In various embodiments, the circuit networks 320, 520, and 530 may provide signal attenuations anywhere from about 10 dB to about 100 dB, for example from about 20 dB to about 60 dB.

Figure 17:
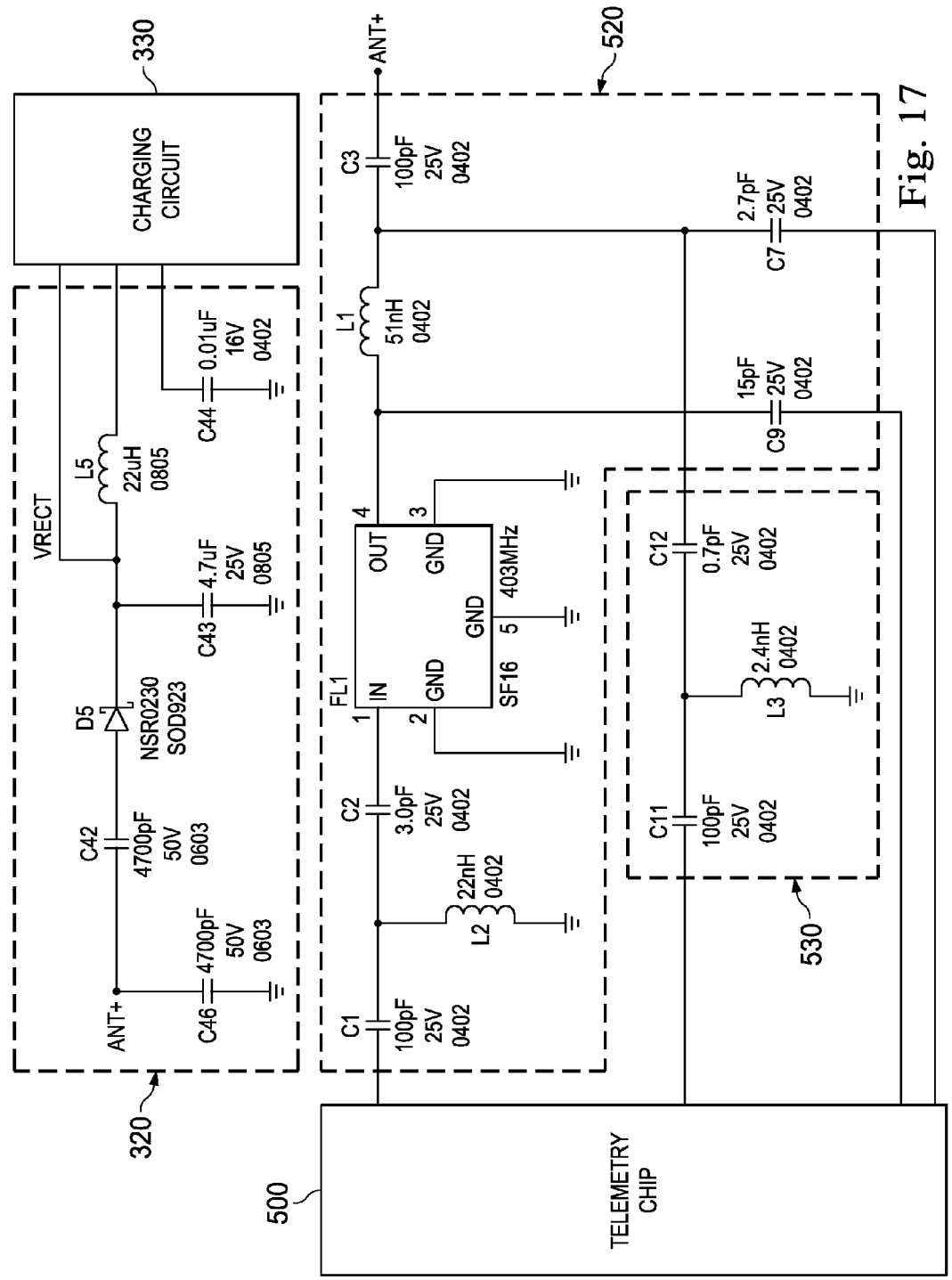
FIG. 17 illustrates circuit schematics of the various components of the peripheral neurostimulator used to provide signal discrimination according to an embodiment.

FIG. 17 includes detailed circuit schematics of an embodiment for each of the circuit networks 320, 520, and 530 discussed above. These circuit schematics are extracted from the circuit schematic of the PNS device 200 shown in FIG. 8. In addition, to provide more clarity, simplified block diagrams of the charging circuit 330 and the telemetry chip 500 are appended next to the circuit schematics of the corresponding circuit networks 320, 520, and 530. It is also understood that a circuit node "ANT+" represents the signal line to the single antenna (or the coil 700 shown in FIG. 16)

According to the embodiment shown in FIG. 17, the circuit network 320 includes a series-resonant capacitor C42 and/or a parallel-resonant capacitor 46. These resonant capacitors C42 and C46 are tuned such that they have a narrow resonant frequency at around 13.56 Mhz (since 13.56 Mhz is the band of the inductive charging signals in this case). As discussed above, the resonant capacitors C42 and C46 in effect serve as a narrow band-pass-like filter, where the pass-band is centered around 13.56 Mhz. As such, the inductive charging signals of the 13.56 Mhz ISM band are able to pass through, whereas signals from other frequency bands end up being "rejected" because they are outside the resonant frequency. In some embodiments, the series capacitor C42 may be removed, and only the parallel-resonant capacitor C46 is used to provide a resonant frequency.

The circuit network 320 further includes a diode D5 that is electrically coupled to the capacitor C42. The diode D5 serves as a rectifying element. In other words, the diode D5 converts the AC inductive signal that passes through (13.56 Mhz) into a DC signal. In other embodiments, alternative types of DC rectifiers may be used instead. The circuit network 320 also includes a capacitor C43, which serves as an energy storage element herein. The inductor L5 may serve as an inductor for the booster circuit, and the capacitor C44 may serve as a reference capacitor for the booster circuit.

The circuit network 520 includes a band-pass filter FL1, whose pass-band in this embodiment is centered around the 400 Mhz MICS band. For example, the pass-band of the band-pass filter FL1 may be from approximately 402 Mhz to about 405 Mhz. As such, the desired telemetry signals in the MICS band will pass through the circuit network 520, whereas inductive charging signals and telemetry signals from other bands will be substantially rejected. In order to provide further attenuation for undesired signals, the circuit network 520 also includes a high-pass filter that is formed by an inductor L2 and capacitors C1 and C2. This high-pass filter is specifically targeted at the inductive charging signals, for example signals at the 13.56 Mhz band, since these inductive charging signals may be high in amplitude and thus warrants further attenuation.

In addition, the circuit network 520 also includes passive circuit elements L1, C9, C3, and C7 that are collectively configured to optimize impedance matching between the antenna (coil 700) and the telemetry chip 500. Again, the impedance matching provided by the passive circuit Elements L1, C9, C3, and C7 may maximize power transfer (e.g., from the antenna to the telemetry chip 500 or vice versa) and/or reduce signal reflection.

The circuit network 530 includes a high-pass filter formed by an inductor L3 and capacitors C11 and C12. This high-pass filter is configured such that the inductive charging signals in the 13.56 Mhz band and the telemetry signals in the 400 Mhz MICS band will be substantially rejected, but the telemetry signals in the 2.45 Ghz band (e.g., used to wake up the PNS device 200) will be allowed to pass through.

Again, it is understood that the specific implementation of the circuit networks 320, 520, and 530 shown in FIG. 17 is merely an example implementation. In alternative embodiments, the specific values may be changed for the resistors, the inductors, and the capacitors shown in FIG. 17. The circuit networks 320, 520, and 530 may also include additional circuit elements, or some of the circuit elements may be eliminated without departing from the spirit and scope of the present disclosure. Furthermore, in some embodiments, digital-signal-processor (DSP) chips or other chips with advanced firmware/software may be used to replace one or more of the circuit networks 320, 520, and 530 discussed above.

Figure 18:
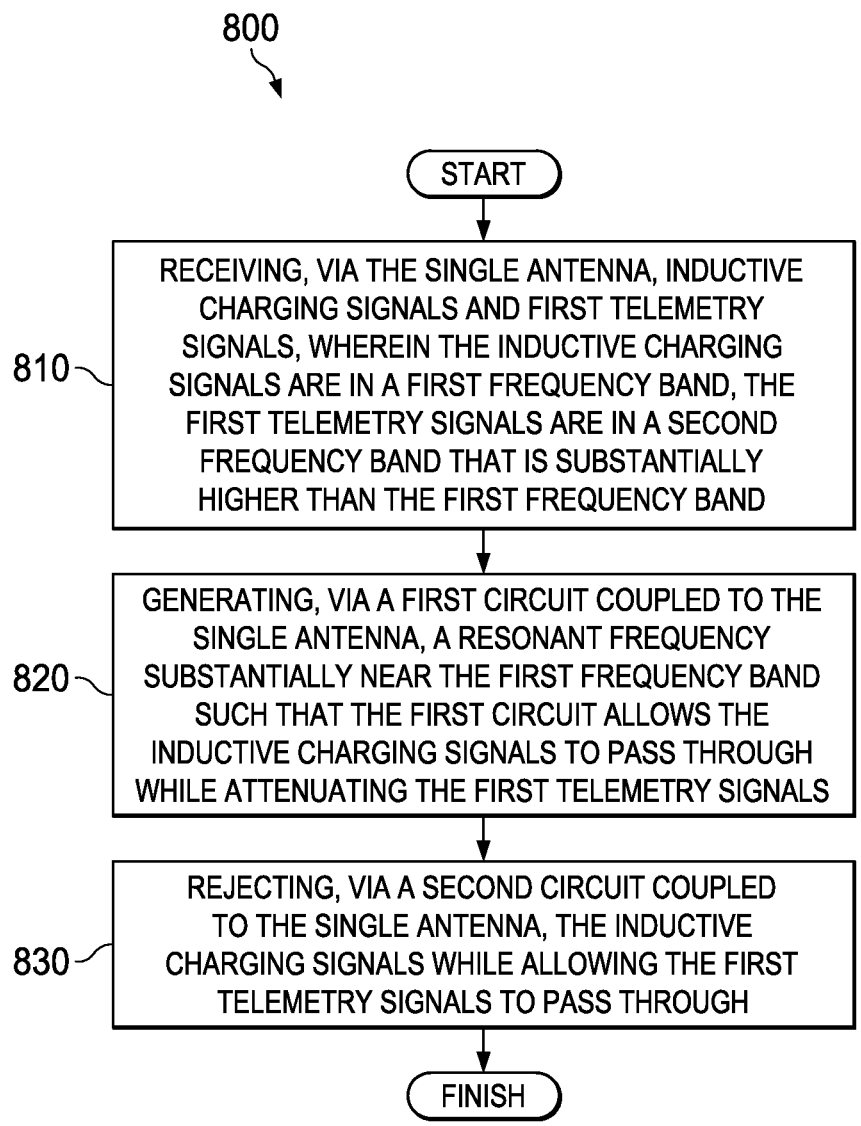
FIG. 18 is a simplified flowchart illustrating a method of providing discrimination for a plurality of types of signals received from a single conductive element according to an embodiment of the present disclosure.

FIG. 18 is a simplified flowchart of a method 800 of providing discrimination for a plurality of types of input signals received from a single antenna according to an embodiment of the present disclosure. The method 800 includes a step 810 of receiving, via the single antenna, inductive charging signals and first telemetry signals. The inductive charging signals are in a first frequency band, the first telemetry signals are in a second frequency band that is substantially higher than the first frequency band.

The method 800 includes a step 820 of generating, via a first circuit coupled to the single antenna, a resonant frequency substantially near the first frequency band such that the first circuit allows the inductive charging signals to pass through while attenuating the first telemetry signals.

The method 800 includes a step 830 of rejecting, via a second circuit coupled to the single antenna, the inductive charging signals while allowing the first telemetry signals to pass through.

In some embodiments, the first and second circuits are integrated within a hermetically-sealed housing of a peripheral nerve stimulation (PNS) device. The single antenna is located outside the hermetically-sealed housing. The method 800 may further include the following steps: receiving, via the single antenna, second telemetry signals in a third frequency band that is substantially higher than the second frequency band; charging a battery of the PNS device in response to the receiving of the inductive charging signals; waking up stimulation circuitry of the PNS device in response to the receiving of the second telemetry signals; and generating, via the stimulation circuitry, a plurality of electrical pulses to be delivered to a patient for an electrical stimulation therapy.

It is understood that additional process steps may be performed before, during, or after the steps 810-830. For example, the method 800 may include a step of rejecting, via a third circuit coupled to the single antenna, the inductive charging signals and the first telemetry signals while allowing the second telemetry signals to pass through. As another example, the method 800 may include a step of matching an impedance of the single antenna with an impedance of a telemetry chip via a plurality of passive circuit elements in the second circuit, wherein the second circuit is coupled between the single antenna and the telemetry chip. For reasons of simplicity, other additional steps are not discussed herein. In addition, the steps 810-830 need not necessarily be performed according to the sequence shown in FIG. 18.

Method and Apparatus of Conserving Power for an Implantable Peripheral Neurostimulator For implantable medical devices such as peripheral neurostimulators, battery life is one of the important considerations. An implantable medical device with poor battery life may require frequent charging, which may diminish the user's satisfaction with the implantable medical device. Many conventional neurostimulators, such as spinal cord stimulators, lack optimized power management. Therefore, in spite of the relatively large size and the accompanying onboard battery with a relatively big capacity, many conventional neurostimulators have poor battery life performance.

In comparison, the PNS device 200 of the present disclosure has a miniature size (especially compared to conventional spinal cord stimulators) and therefore a smaller battery with limited capacity. Therefore, the present disclosure employs various advanced power conservation strategies to maximize the battery life of the PNS device 200, as discussed in more detail below. The advanced power conservation strategies lead to excellent battery performance of the PNS device 200 (e.g., lasting for weeks or months without needing a charge), in spite of its miniature size.

One of the power conservation strategies of the PNS device 200 involves operating the microcontroller 400 (discussed above with reference to FIG. 7) in different power modes depending on the stage of the stimulation pulse. In more detail, the microcontroller 400 offers a plurality of different operating modes, where each operating mode may be used to performance a suitable task(s) and therefore has a different power consumption level. Table 1. below includes a brief listing of the different operating modes:

| | AM | | | | | | | | LPM4.5 | |
|---|---|---|---|---|---|---|---|---|---|---|
| | Active | Active, FRAM off | LPM0 CPU Off | LPM1 CPU Off | LPM2 Standby | LPM3 Standby | LPM4 Off | LPM3.5 RTC only | Shutdown with SVS | Shutdown without SVS |
| Maximum System Clock | 16 MHz | | 16 MHz | 16 MHz | 50 kHz | 50 kHz | 0 | 50 kHz | 0 | |
| Typical Current Consumption, $T_A$ = 25° C. | 103 µA/MHz | 65 µA/MHz | 70 µA at 1 MHz | 35 µA at 1 MHz | 0.7 µA | 0.4 µA | 0.3 µA | 0.25 µA | 0.2 µA | 0.02 µA |
| Typical Wake-Up Time | | N/A | Instant | 6 µs | 6 µs | 7 µs | 7 µs | 250 µs | 250 µs | 1000 µs |
| Wake-Up Events | | N/A | All | All | LF I/O | LF I/O comp | I/O Comp comp | RTC I/O | | I/O |
| CPU | | On | Off | Off | Off | Off | Off | Reset | | Reset |
| FRAM | On | Off | Standby (or off) | Off | Off | Off | Off | Off | | Off |
| High-Frequency Peripherals | | Available | Available | Available | Off | Off | Off | Reset | | Reset |
| Low-Frequency Peripherals | | Available | Available | Available | Available | Available | Off | RTC | | Reset |
| Unclocked Pheripherals | | Available | Available | Available | Available | Available | Available | Reset | | Reset |
| MCLK | | On | Off | Off | Off | Off | Off | Off | | Off |
| SMCLK | | Optional | Optional | Optional | Off | Off | Off | Off | | Off |
| ACLK | | On | On | On | On | On | Off | Off | | Off |
| Full Retention | | Yes | Yes | Yes | Yes | Yes | Yes | No | | No |
| SVS | | Always | Always | Always | Optional | Optional | Optional | Optional | On | Off |
| Brownout | | Always | Always | Always | Always | Always | Always | Always | | Always |

In more detail, AM refers to an active mode of operation, where no power conservation approaches are used. LPM0, LMP1, LPM2, LPM3, LPM4, LPM3.5, and LPM4.5 are the various power-conservation modes in which the microcontroller 400 can operate. CPU refers to the microcontroller core 410 (discussed above with reference to FIG. 7). MCLK is the main clock (clocked at 10 Mhz in this embodiment but may have a different clock rate in other embodiments, for example 20 Mhz) of the microcontroller 400, ACLK is an auxiliary clock (clocked at 32.768 Khz in this embodiment but may have a different clock rate in other embodiments) of the microcontroller 400, SMCLK is a sub-main clock of the microcontroller 400, DCOCLK is a digitally-generated clock that is feeding the main clock. In addition, DCO is a digitally-controller oscillator, and FLL is a frequency-locked loop.

As is shown in Table 1, the microcontroller 400 turns on and off the various clocks and/or the peripherals of the microcontroller differently for each of the operating modes. This is summarized briefly as follows:

Active mode (AM)
  All clocks are active
Low-power mode 0 (LPM0)
  CPU is disabled
  ACLK and SMCLK remain active, MCLK is disabled
  FLL loop control remains active
Low-power mode 1 (LPM1)
  CPU is disabled
  FLL loop control is disabled
  ACLK and SMCLK remain active, MCLK is disabled
Low-power mode 2 (LPM2)
  CPU is disabled
  MCLK, FLL loop control, and DCOCLK are disabled
  DCO's DC generator remains enabled
  ACLK remains active
Low-power mode 3 (LPM3)
  CPU is disabled
  MCLK, FLL loop control, and DCOCLK are disabled
  DCO's DC generator is disabled
  ACLK remains active
Low-power mode 4 (LPM4)
  CPU is disabled
  ACLK is disabled
  MCLK, FLL loop control, and DCOCLK are disabled
  DCO's DC generator is disabled
  Crystal oscillator is stopped
  Complete data retention As one example, the microcontroller 400 may operate in the LPM4 power-conservation when the PNS device 200 is not in use. The LPM4 mode is also referred to as a "deep sleep" mode, where the microcontroller 400 draws almost no current (i.e., consumes virtually no power). The microcontroller 400 has to be "woken up" from this deep sleep LPM4 mode by an external signal. By doing so, the deep sleep LPM4 mode allows the microcontroller 400 to not waste power in standby.

As another example, the waveforms for the electrical stimulation pulses are generated by the microcontroller 400's internal DAC (digital-to-analog converter) in real-time for each pulse. In between stimulation pulses—referred to as a standby period herein—the microcontroller 400 enters one of the power-conservation modes (also referred to as a low-power mode or sleep mode), for example the LPM3 mode. This reduces power consumption, since many parts of the microcontroller does not need to be turned on during the standby period. It is understood that the microcontroller 400 does not necessarily need to operate in the LPM3 throughout the entirety of the standby period in order to realize the power savings. According to various embodiments of the present disclosure, the microcontroller 400 may operate in the LMP3 power conservation mode in a substantial majority of the standby period, for example >75% of the standby period in some embodiments, or >90% of the standby period in some other embodiments, or >99% of the standby period in yet some other embodiments.

When the microcontroller 400 enters the LPM3 power-conservation mode, the system clock switches from the main system clock (MCLK, which is 10 MHz in this embodiment) to the crystal oscillator 430 (shown in FIG. 7) that is external to the microcontroller 400. The crystal oscillator 430 has a clock frequency that is much lower than the main system clock, for example with a clock frequency of 32.678 kHz in this case, compared to the 10 Mhz clock frequency of the main system clock. Typically, a high clock frequency corresponds with more power consumption. Therefore, switching from a 10 Mhz clock to a 32.678 Khz clock also reduces power consumption.

Figure 19:
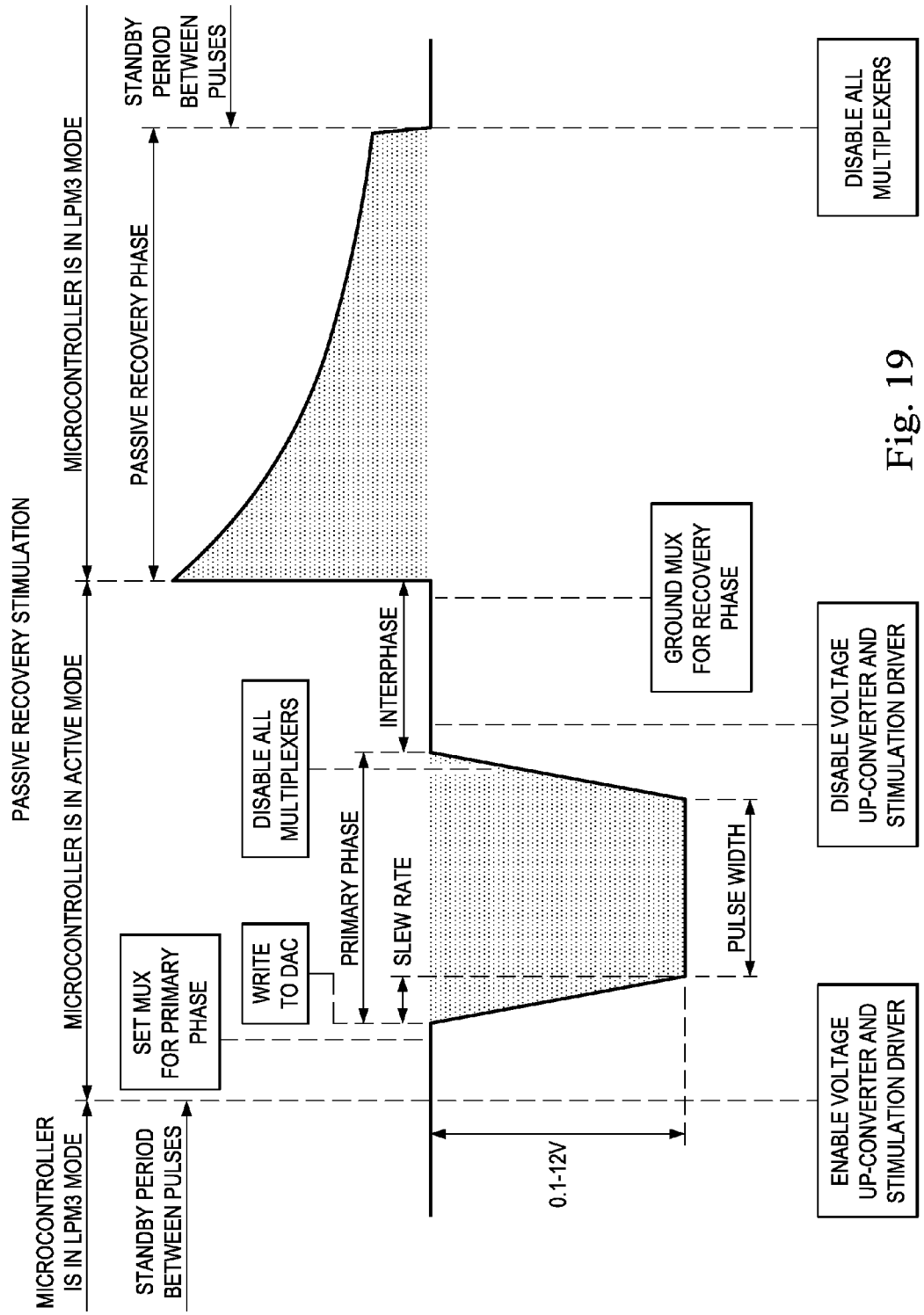
FIG. 19 illustrates the power-reduction approaches employed by a peripheral neurostimulator during a passive recovery stimulation pulse according to an embodiment of the present disclosure.
Figure 20:
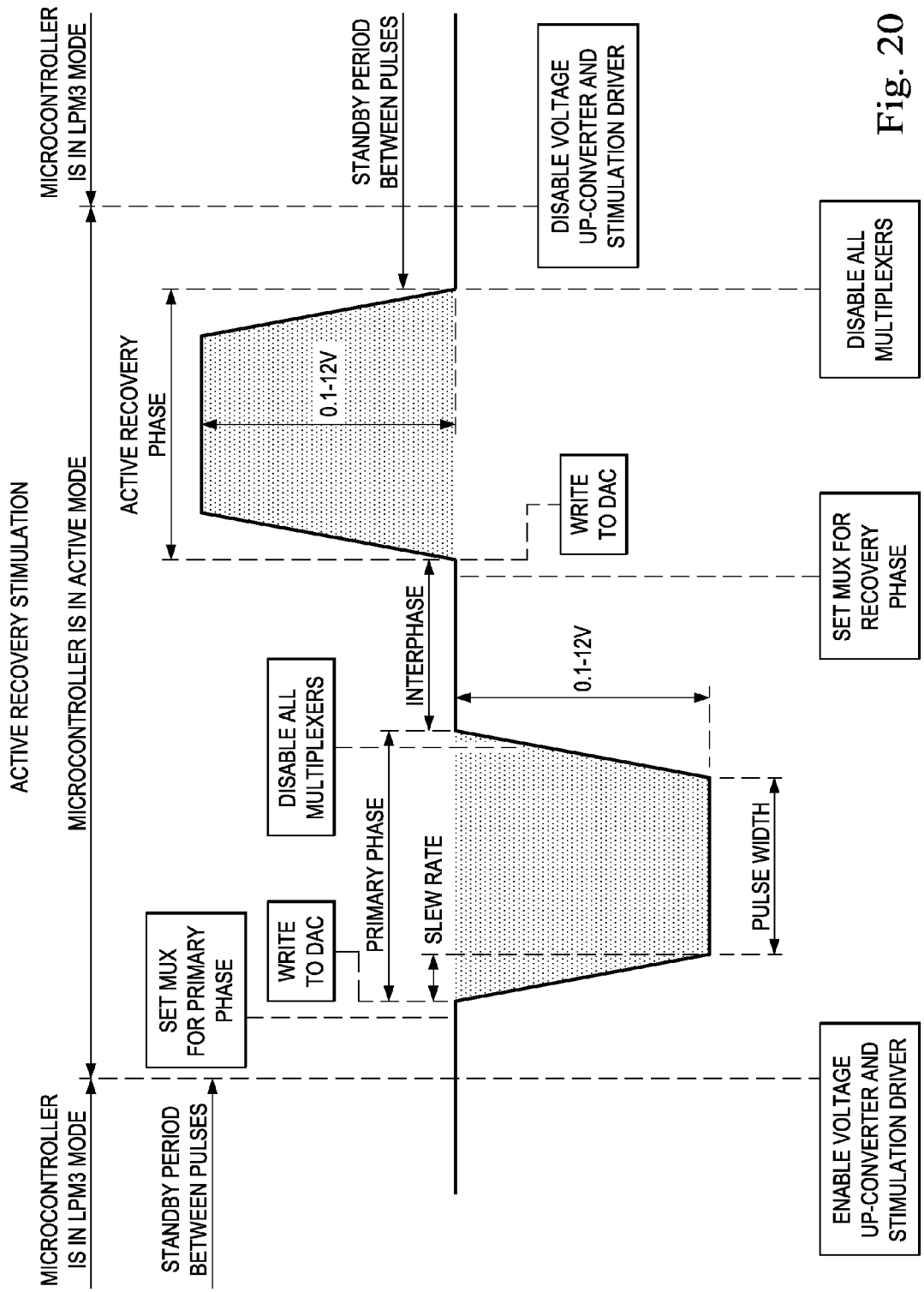
FIG. 20 illustrates the power-reduction approaches employed by a peripheral neurostimulator during an active recovery stimulation pulse according to an embodiment of the present disclosure.

Moreover, the microcontroller core 410 is turned off in the LPM3 mode. Meanwhile, the DMA unit 420 may be kept on (and is driven by the crystal oscillator 430) during the LPM3 mode to send instructions to various peripherals, such as the DAC. For example, the DMA unit 420 may be configured to write the digital waveform data to the DAC. When the writing of the digital waveform data into the DAC is complete, the DAC outputs the analog stimulation waveforms, i.e., the electrical stimulation pulse. Again, this process does not require the microcontroller core 410 to be running. As discussed above, the microcontroller core 410 is the main power-hog in the microcontroller 400 and consumes substantially more power than the DMA unit 420. Consequently, turning off the microcontroller core 410, coupled with the switching from the 10 Mhz main system clock to the 32.678 Khz clock of the crystal oscillator 430, allows the power consumption to be reduced from approximately 3 mA down to approximately 3 uA in some embodiments. In some embodiments, an interrupt signal generated by the timer unit 425 (shown in FIG. 7)—clocked by the 32.768 kHz crystal oscillator 430—may be used to wake the microcontroller 400 up from the LPM3 mode back to the active mode in time to generate the next pulse In addition, depending on the stimulation waveform type (active or passive recovery), additional measures are employed to reduce power consumption. To illustrate, two example waveforms representing two different types of a bi-phasic stimulation pulse are shown in FIGS. 19-20. Specifically, the waveform in FIG. 19 shows a stimulation pulse with a passive recovery, and the waveform in FIG. 20 shows a stimulation pulse with an active recovery. Generally, a bi-phasic stimulation pulse includes a primary phase, an interphase, and a recovery phase. The primary phase is a period of time during which the actual stimulation pulse is generated. The recovery phase is a period of time to allow charges on the electrodes to rebalance. The interphase is a period of time between the primary phase and the recovery phase. For stimulation pulses with a passive recovery phase, the charges are passively rebalanced over time. In comparison, for stimulation pulses with an active recovery phase, a "pulse" that is opposite in polarity (but substantially equal in amplitude) of the actual pulse (e.g., generated in the primary phase) is generated to allow the charges to balance more quickly. Therefore, the trade-off between passive recovery and active recovery is that passive recovery consumes less power but takes longer, and active recovery consumes more power but is quicker, which allows for stimulation at a higher frequency.

Referring now to FIG. 19, the primary phase, interphase, and the passive recovery phase are clearly illustrated for a stimulation pulse with passive recovery. In addition, portions of the standby period that is in between consecutive stimulation pulses are also illustrated. In some embodiments, the standby period may begin at the end of the recovery phase and may last until the beginning of the primary phase for the next pulse. It is understood that the standby period can be much longer than the actual pulse itself. For example, the time duration for an entire pulse—which includes the primary phase, interphase, and recovery phase—may last from about 2 milli-seconds to about 4 milli-seconds according to some embodiments. In comparison, the time duration for the standby period may last between about 1 milli-second to about 1 second. In other words, the standby period may be more than 4 to 10 times longer than the actual pulse in some embodiments.

For most conventional neurostimulators, once a microcontroller is turned on, it remains turned on during the stimulation pulses as well as in between the stimulation pulses. Stated differently, most conventional neurostimulators keep the microcontroller turned on even during the standby period. In comparison, the microcontroller 400 of the PNS device 200 is turned on only when necessary. As FIG. 19 illustrates, the microcontroller operates in the LPM3 power-conservation mode during most of the standby period between consecutive stimulation pulses. As discussed above, the microcontroller core 410 is turned off in the LPM3 mode, which reduces power consumption significantly as the microcontroller core 410 is a power-hungry device. Right before the pulse needs to be generated, the microcontroller 400 "wakes up" from the LPM3 power-conservation mode and begins to operate in the active mode (where the microcontroller core 410 is turned on). The waking of the microcontroller 400 may be done by a timer signal generated by the timer unit 425, for example.

In the embodiment shown in FIG. 19, the microcontroller 400 wakes up from the LPM3 power-conservation mode and begins to operate in the active mode about 100 micro-seconds before the start of the primary phase. This is done so that the microcontroller 400 can enable the voltage up-converter (e.g., a charge pump) 370 and the stimulation driver 450 discussed above with reference to FIG. 7 in preparation for the pulse generation. At some time after that, but still before the pulse is generated (before the start of the primary phase), the microcontroller 400 sets or configures the multiplexers 460 so that desired stimulation channels can be formed. In the embodiment shown in FIG. 19, the multiplexers 460 are configured about 10 micro-seconds before the start of the primary phase.

Either the DMA unit 420 or the microcontroller core 410 may be used to write the digital data for the stimulation waveform to the DAC. Once the data has been completely written into the DAC, the stimulation pulse is generated by the DAC, thereby defining the start of the primary phase of the pulse. The stimulation pulse coming out of the DAC is amplified by the stimulation driver 450 to achieve the target amplitude needed for the peripheral stimulation therapy. In the illustrated embodiment, the amplified pulse amplitude ranges from about 0.1 V to about 12 V. The stimulation driver 450 may also have a slew rate of about 2.3 V/micro-seconds in the illustrated embodiment.

The pulse width, or the time duration of the primary phase, may be programmably configured. In various embodiments, the pulse width may be in a range from about 20 micro-seconds to about 2000 micro-seconds. Right before (or at) the end of the primary phase and before the start of the interphase, the multiplexers 460 are also disabled in order to further reduce power consumption. In the illustrated embodiment, the multiplexers 460 are disabled about 1 micro-second before the start of the interphase.

In the illustrated embodiment, the interphase may last for about 20 micro-seconds. At the start of the interphase, or shortly after (e.g., a few micro-seconds), the voltage up-converter 370 is disabled to further reduce power consumption. The voltage up-converter 370 (e.g., a charge pump), when activated, supplies power to the stimulation driver 450 and the multiplexers 460 when the stimulation pulse calls for a higher voltage than what the battery 340 can supply. For example, in the present embodiment, when the stimulation pulse needs to have an amplitude higher than about 3.5 V or 4 V, the battery 340 cannot supply this high of voltage. The voltage up-converter 370 is then turned on to ensure that the compliance voltage is sufficiently high. For conventional neurostimulators, such voltage-converter (if it exists) is typically kept turned on to generate a constant high-voltage stimulation compliance voltage, regardless of the phase of the stimulation pulse. This causes power to be wasted needlessly. In comparison, the voltage up-converter 370 of the PNS device 200 can be enabled shortly before (e.g., a few microseconds) the stimulation pulse is generated and disabled just after (e.g., a few microseconds) the stimulation pulse is generated. By doing so, steady-state power consumption of the PNS device 200 is reduced significantly.

Similarly, the stimulation driver 450 can be enabled shortly before (e.g., a few microseconds) the stimulation pulse is generated and disabled shortly after (e.g., a few microseconds) the stimulation pulse is generated. Again, the timely enabling and disabling of the stimulation driver 450 prevents power from being wasted needlessly outside the primary phase of the stimulation pulse.

Shortly before the end of the interphase and before the start of the passive recovery phase, the multiplexers 460 are turned on but grounded. This allows the electrical charge that has been built up on the capacitors 465 to discharge back into the tissue. In the illustrated embodiment, the grounding of the multiplexers 460 occurs about 1 micro-second before the recovery phase. The recovery phase is passive because the built-up charges are just "passively" being discharged to perform charge balancing, so as to achieve zero voltage on the electrodes at the end of the passive recovery phase. In the illustrated embodiment, the passive recovery phase may last for about 2 to 6 milli-seconds.

At the end (or shortly after) of the passive recovery phase, the multiplexers 460 are disabled (e.g., they may go into a high impedance mode) in order to further reduce power consumption. This marks the end of one cycle of the bi-phasic pulse, and the standby period follows the end of the previous pulse (and before the start of the subsequent pulse). To further reduce power consumption, the timer unit 425 instructs the microcontroller 400 to enter or operate in the LPM3 mode again during the standby period. This process discussed above may repeat indefinitely for each passive stimulation pulse cycle until stimulation is shut off.

Referring now to FIG. 20, the operation of the PNS device 200 for active recovery stimulation shares many similarities with the passive recovery stimulation discussed above with reference to FIG. 19, with certain differences. In more detail, up to the point of the interphase, the operation/configuration of the microcontroller 400 and the various other components of the PNS device 200 are substantially identical for passive recovery stimulation and active recovery stimulation. However, whereas the voltage up-converter 370 and the stimulation driver 450 are disabled at or shortly after the start of the interphase for passive recovery stimulation, the voltage up-converter 370 and the stimulation driver 450 remain turned on during the interphase for active recovery stimulation. In addition, whereas the multiplexers 460 are grounded before the start of the recovery phase for passive recovery stimulation, the multiplexers 460 are actually configured before (e.g., about 1 milli-seconds before) the recovery phase for active recovery stimulation. These differences reflect the fact that another pulse needs to be generated during the recovery phase for active recovery stimulation.

For example, the microcontroller core 410 or the DMA unit 420 writes digital waveform data into the DAC during the interphase, and at the completion of this data writing process, the DAC outputs a stimulation pulse that is substantially equal in pulse width but opposite in polarity with the actual stimulation pulse generated in the primary phase. The generation of this "opposite" pulse corresponds to the active recovery phase. The active recovery phase is thus much shorter than the passive recovery phase, which may allow for a higher stimulation frequency.

Since the active recovery phase require pulse generation during the recovery phase, the microcontroller 400 operates in the active mode for the entire 3 phases of the stimulation pulse (i.e., the primary phase, the interphase, and the active recovery phase). Furthermore, the voltage up-converter 370 and the stimulation driver 450 remain turned on during the entire 3 phases of the stimulation pulse to ensure voltage compliance and to amplify the stimulation pulse outputted by the DAC.

At the end of the active recovery phase, or shortly thereafter (e.g., a few micro-seconds thereafter), the multiplexers 460 are disabled, and the voltage up-converter 370 and the stimulation driver 450 are also disabled. The microcontroller 400 also reverts back to the LPM3 power-conservation mode after the end of the active recovery phase. In other words, these power-consuming components are disabled in the standby period (or at least a substantial majority thereof) between consecutive pulses in order to conserve power. This process discussed above may repeat for each active recovery stimulation pulse indefinitely until stimulation is shut off.

It is understood that the active mode and the LPM3 power conservation mode are used as mere examples herein to illustrate certain aspects of the power reduction strategies of the PNS device 200. In other embodiments, any of the other power-conservation modes may also be employed to reduce power consumption. For example, in some embodiments, the microcontroller core 410 may be turned off during one or more of the phases within a pulse, and the DMA unit 420 may be used to perform other tasks instead of the microcontroller core 410, such as writing data to the DAC.

The above discussions pertain to power reduction achieved by selectively operating the microcontroller 400 in a power-conservation mode whenever appropriate, as well as timely disabling and enabling power-consuming components such as the voltage up-converter 370, the stimulation driver 450, and the multiplexers 460 throughout the different phases of the stimulation pulse. In other words, the PNS device 200 micro-manages the various power-consuming components within to ensure that no power is needlessly wasted.

Another example of the micromanagement used to conserve power pertains to disconnecting the voltage up-converter 370 from its load (e.g., the stimulation driver 450 and the multiplexers 460) between consecutive stimulation pulses (i.e., during the standby period). In more detail, the voltage up-converter 370 may employ an output capacitor to store charge. Even if the voltage up-converter 370 is turned off between the stimulation pulses (during the standby period), any load connected to the output capacitor may still drain the charge out of the output capacitor. In other words, the stimulation driver 450 and the multiplexers 460 herein may serve as the load that will cause the output capacitor of the voltage up-converter 370 to discharge. This means that when the voltage up-converter is turned on the next time, it will have to charge up the output capacitor again, thereby wasting power.

According to various embodiments of the present disclosure, the switch 480 (discussed above with reference to FIG. 7) can be used to disconnect the stimulation driver 450 and the multiplexers 460 (i.e., the load of the voltage up-converter 370) from the voltage up-converter during the standby period, even as the voltage up-converter 370, the stimulation driver 450, and the multiplexers 460 are turned off. By timely disconnecting the load from the voltage up-converter 370, energy (i.e., electrical charge) stored in the voltage up-converter 370 may be preserved for the next stimulation pulse.

It is understood that in some embodiments, the timer unit 425 (or the timer signals generated therefrom) may be used to control the timing for the micromanage tasks discussed above, i.e., switching the microcontroller 400 between the active mode and one of the power-conservation modes, enabling/disabling the voltage up-converter 370, the stimulation driver 450, and the multiplexers, disconnecting the load from the voltage up-converter 370, and/or writing to the DAC. The timer unit 425 may be programmed by firmware or software to perform these tasks.

It is also understood that although a typical bi-phasic pulse is used herein as an example of a stimulation pulse, the concepts discussed herein may apply to other types of stimulation pulses as well. For example, certain types of stimulation pulses may have a plurality of pulses in the primary phase before the interphase and the recovery phase. Even for these types of stimulation pulses, the microcontroller 400 may still switch its mode of operation in the standby period, and the other components such as the voltage up-converter and stimulation drive may still be micromanaged appropriately in order to reduce power consumption. Furthermore, although the embodiment shown in FIGS. 19-20 illustrate operating the microcontroller 400 in the active mode during the pulse generation, the microcontroller 400 may also operate in one or more of the other power-conservation modes (e.g., the LPM1 mode) even during the pulse generation in order to further reduce power consumption.

Figure 21:
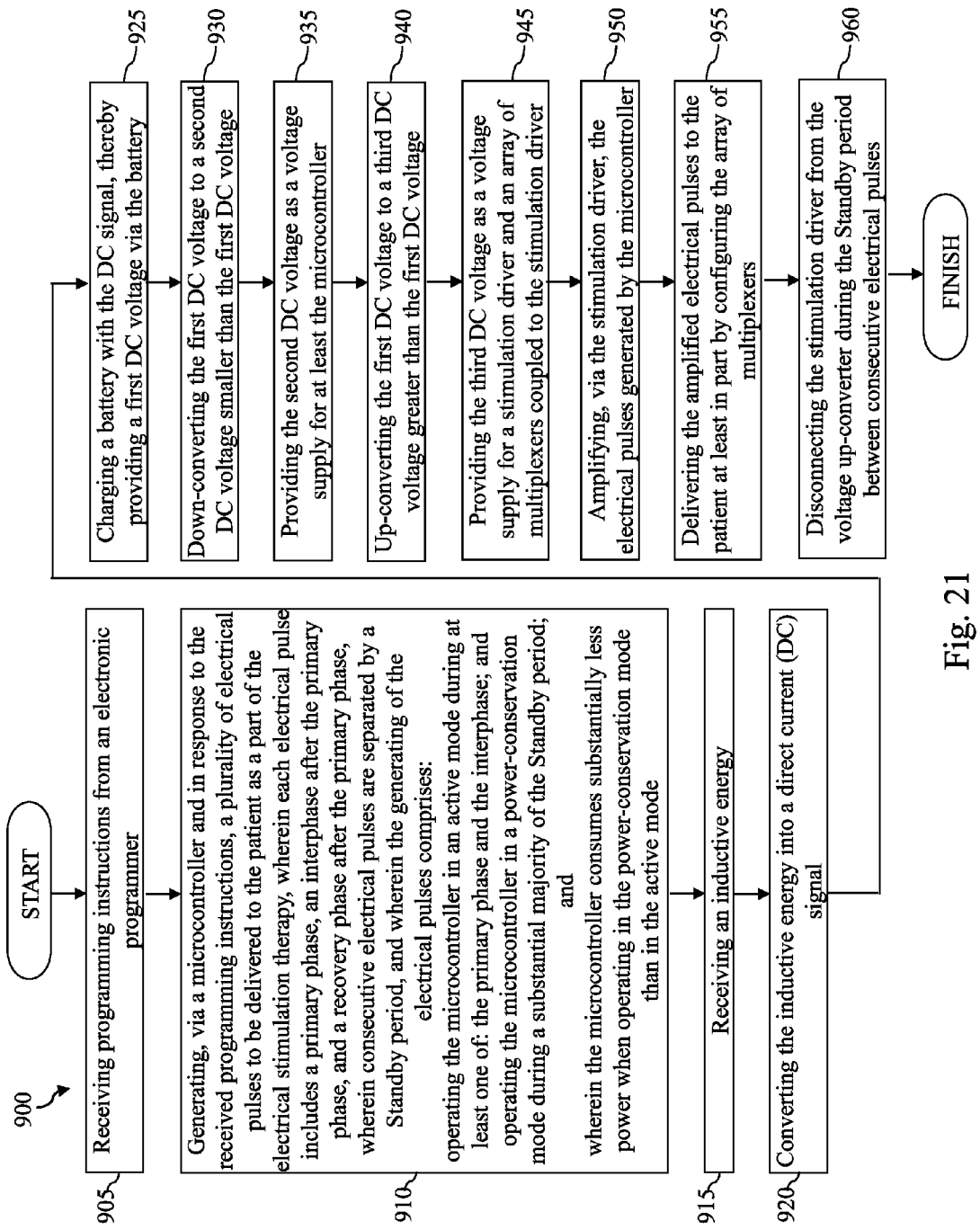
FIG. 21 is a simplified flowchart illustrating a method of reducing power consumption for a peripheral neurostimulator according to an embodiment of the present disclosure.

FIG. 21 is a simplified flowchart of a method 900 of providing an electrical stimulation therapy for a patient according to an embodiment of the present disclosure. The method 900 includes a step 905 of receiving programming instructions from an electronic programmer.

The method 900 includes a step 910 of generating, via a microcontroller and in response to the received programming instructions, a plurality of electrical pulses to be delivered to the patient as a part of the electrical stimulation therapy. Each electrical pulse includes a primary phase, an interphase after the primary phase, and a recovery phase after the primary phase. Consecutive electrical pulses are separated by a standby period. The step 910 of generating of the electrical pulses comprises: operating the microcontroller in an active mode during at least one of: the primary phase and the interphase; and operating the microcontroller in a power-conservation mode during a substantial majority of the standby period. The microcontroller consumes substantially less power when operating in the power-conservation mode than in the active mode. In some embodiments, the microcontroller is the microcontroller 400 of FIG. 7.

The method 900 includes a step 915 of receiving an inductive energy. In some embodiments, the inductive energy is received via a coil, for example by the conductive charging mechanism 320 of FIG. 7 (an embodiment of which is illustrated as the coil 700 of FIGS. 15A-15C).

The method 900 includes a step 920 of converting the inductive energy into a direct current (DC) signal. In some embodiments, the converting of the inductive energy is performed by the charging circuit 330 of FIG. 7.

The method 900 includes a step 925 of charging a battery with the DC signal, thereby providing a first DC voltage via the battery. In some embodiments, the battery is the battery 340 of FIG. 7, and the first voltage is the output voltage of the battery 340.

The method 900 includes a step 930 of down-converting the first DC voltage to a second DC voltage smaller than the first DC voltage. In some embodiments, the down-converting is performed by the voltage down-converter 360 of FIG. 7, and the second DC voltage is the output voltage of the voltage down-converter 360. In some embodiments, the voltage down-converter 360 includes a buck converter.

The method 900 includes a step 935 of providing the second DC voltage as a voltage supply for at least the microcontroller.

The method 900 includes a step 940 of up-converting the first DC voltage to a third DC voltage greater than the first DC voltage. In some embodiments, the up-converting is performed by the voltage up-converter 370 of FIG. 7, and the third DC voltage is the output voltage of the up-converter 370. In some embodiments, the voltage down-converter 370 includes a charge pump.

The method 900 includes a step 945 of providing the third DC voltage as a voltage supply for a stimulation driver and an array of multiplexers coupled to the stimulation driver. In some embodiments, the stimulation driver is the stimulation driver 450 of FIG. 7, and the array of multiplexers includes the multiplexers 460 of FIG. 7.

The method 900 includes a step 950 of amplifying, via the stimulation driver, the electrical pulses generated by the microcontroller.

The method 900 includes a step 955 of delivering the amplified electrical pulses to the patient at least in part by configuring the array of multiplexers.

The method 900 includes a step 960 of disconnecting the stimulation driver from the voltage up-converter during the standby period between consecutive electrical pulses. In some embodiments, the disconnecting is performed at least in part by the switch 480 of FIG. 7.

In some embodiments, the microcontroller of the method 900 contains a microcontroller core (e.g., the microcontroller core 410 of FIG. 7) and a direct memory access (DMA) unit (e.g., the DMA unit 420 of FIG. 7) that is separate from the microcontroller core and consumes substantially less power than the microcontroller core. In these embodiments, the operating of the microcontroller may comprises a step of turning on the microcontroller core in the active mode, turning off the microcontroller core in the power-conservation mode, and keeping the DMA unit turned on in the power-conservation mode. In some embodiments, the microcontroller contains a system clock that is running at a first frequency, and the stimulation circuitry further comprises an oscillator that is external to the microcontroller. The oscillator runs at a second frequency that is substantially lower than the first frequency. In these embodiments, the operating of the microcontroller comprises driving the microcontroller with the system clock in the active mode. The DMA unit is also driven with the oscillator in the power-conservation mode. In addition, the method 900 may include a step of generating an interrupt signal with a timer unit (e.g., the timer unit 425 of FIG. 7) that is clocked by the oscillator, and a step of waking up the microcontroller from the power-conservation mode via the interrupt signal immediately before a subsequent electrical pulse needs to be generated.

It is understood that the steps 905-960 need not necessarily be performed according to the sequence shown in FIG. 21. In fact, some of these steps may be performed concurrently, or even in an order different from what is shown in FIG. 21. It is also understood that additional process steps may be performed before, during, or after the steps 905-960. For example, as each electrical pulse may include either a passive recovery phase or an active recovery phase, different process steps may be performed depending on whether the electrical pulse has a passive recovery phase or an active recovery phase. If the electrical pulse has a passive recovery phase, then the method 900 may include a step of enabling the voltage up-converter and the array of multiplexers before the primary phase, a step of disabling the voltage up-converter and the array of multiplexers during the interphase, and a step of operating the microcontroller in the power-conservation mode during the passive recovery phase. If the electrical pulse as an active recovery phase, then the method 900 may include a step of enabling the voltage up-converter and the array of multiplexers before the primary phase, a step of disabling the voltage up-converter and the array of multiplexers after the active recovery phase, and a step of operating the microcontroller in the active mode during the active recovery phase. For reasons of simplicity, other additional steps are not discussed herein.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A medical device for providing an electrical stimulation therapy for a patient, the medical device comprising:
   telemetry circuitry configured to receive programming instructions via telecommunications conducted with an electronic programmer;
   stimulation circuitry configured to provide, in response to the received programming instructions, a plurality of electrical pulses to be delivered to the patient as a part, of the electrical stimulation therapy, wherein the stimulation circuitry contains a microcontroller configured to generate the electrical pulses, wherein each electrical pulse includes a primary phase, an interphase after the primary phase, and a passive recovery phase after the primary phase, and wherein consecutive electrical pulses are separated by a standby period, the microcontroller being further configured to:
      operate in an active mode during at least one of: the primary phase and the interphase;
      operate in a power-conservation mode during the passive recovery phase and during a substantial majority of the standby period, the microcontroller consuming substantially less power when operating in the power-conservation mode than in the active mode; and
   power supply circuitry configured to provide electrical power to the telemetry circuitry and the stimulation circuitry.

2. The medical device of claim 1, wherein the power-conservation mode is one of a plurality of available power-conservation modes in which the microcontroller can be operated.

3. The medical device of claim 1, wherein:
   the microcontroller contains a microcontroller core and a direct memory access (DMA) unit that is separate from the microcontroller core and consumes substantially less power than the microcontroller core;
   the microcontroller core is turned on when the microcontroller operates in the active mode and is turned off when the microcontroller operates in the power-conservation mode; and
   the DMA unit remains turned on when the microcontroller operates in the power-conservation mode.

4. The medical device of claim 3, wherein:
   the microcontroller contains a system clock that is running at a first frequency;
   the stimulation circuitry further comprises an oscillator that is external to the microcontroller, the oscillator running at a second frequency that is substantially lower than the first frequency;
   the microcontroller is driven by the system clock when operating in the active mode; and
   the DMA unit is driven by the oscillator when the microcontroller operates in the power-conservation mode.

5. The medical device of claim 4, wherein when operating in the power-conservation mode, the microcontroller is configured to be woken up by an interrupt signal immediately before a subsequent electrical pulse needs to be generated, such that the microcontroller operates in the active mode after being woken up, wherein the interrupt signal is generated by a timer clocked by the oscillator.

6. The medical device of claim 1, wherein:
   the power supply circuitry comprises:
      an inductive charging mechanism configured to receive an inductive energy;
      a charging circuit configured to convert the inductive energy into a direct current (DC) signal;
      a battery charged by the charging circuit to provide a first DC voltage;
      a voltage down-converter that down-converts the first DC voltage to a second DC voltage smaller than the first DC voltage, the second DC voltage being a voltage supply for at least the microcontroller; and
      a voltage up-converter that up-converts the first DC voltage to a third DC voltage that is greater than the first DC voltage, the third voltage being a voltage supply for the stimulation circuitry; and
   the stimulation circuitry further comprises:
      a stimulation driver that amplifies the electrical pulses generated by the microcontroller; and an array of multiplexers coupled between the stimulation driver and an external lead that includes a plurality of electrodes configured to deliver the electrical stimulation therapy to the patient.

7. The medical device of claim 6, further comprising a switch coupled between the voltage up-converter and the stimulation driver, wherein the switch is configured to disconnect the stimulation driver from the voltage up-converter during the standby period in between consecutive electrical pulses.

8. The medical device of claim 6, wherein, for each pulse:
the voltage up-converter and the array of multiplexers are enabled before the primary phase and disabled during the interphase.

9. A medical system for providing an electrical stimulation therapy for a patient, the medical system comprising:
an electronic programmer configured to generate stimulation programming instructions for an implantable pulse generator (IPG); and
the IPG, wherein the IPG comprises:
telemetry circuitry configured to receive the programming instructions via telecommunications conducted with the electronic programmer;
stimulation circuitry configured to provide, in response to the received programming instructions, a plurality of electrical pulses to be delivered to the patient as a part of the electrical stimulation therapy, wherein the stimulation circuitry contains a microcontroller configured to generate the electrical pulses, wherein each electrical pulse includes a primary phase, an interphase after the primary phase, and a passive recovery phase after the primary phase, and wherein consecutive electrical pulses are separated by a standby period, the microcontroller being further configured to:
operate in an active mode during at least one of: the primary phase and the interphase;
operate in a power-conservation mode during the passive recovery phase and during a substantial majority of the standby period, the microcontroller consuming substantially less power when operating in the power-conservation mode than in the active mode; and
power supply circuitry configured to provide electrical power to the telemetry circuitry and the stimulation circuitry.

10. The medical system of claim 9, further comprising: an implantable lead configured to be attached to the IPG, wherein the implantable lead contains a plurality of electrodes configured to deliver the electrical pulses generated by the IPG to a peripheral nerve of the patient.

11. The medical system of claim 9, wherein:
the power supply circuitry comprises:
an inductive charging mechanism configured to receive an inductive energy;
a charging circuit configured to convert the inductive energy into a direct current (DC) signal;
a battery charged by the charging circuit to provide a first DC voltage;
a voltage down-converter that down-converts the first DC voltage to a second DC voltage smaller than the first DC voltage, the second DC voltage being a voltage supply for at least the microcontroller; and
a voltage up-converter that up-converts the first DC voltage to a third DC voltage that is greater than the first DC voltage, the third DC voltage being a voltage supply for the stimulation circuitry; and
the stimulation circuitry further comprises:
a stimulation driver that amplifies the electrical pulses generated by the microcontroller; and
an array of multiplexers coupled between the stimulation driver and an external lead that includes a plurality of electrodes configured to deliver the electrical stimulation therapy to the patient.

12. The medical system of claim 11, further comprising a switch coupled between the voltage up-converter and the stimulation driver, wherein the switch is configured to disconnect the stimulation driver from the voltage up-converter during the standby period in between consecutive electrical pulses.

13. The medical system of claim 11, wherein, for each pulse:
the voltage up-converter and the array of multiplexers are enabled before the primary phase and disabled during the interphase, and the microcontroller is configured to operate in the power-conservation mode during the passive recovery phase.

14. A method of providing an electrical stimulation therapy for a patient, the method comprising:
receiving programming instructions from an electronic programmer; and
generating, via a microcontroller and in response to the received programming instructions, a plurality of electrical pulses to be delivered to the patient as a part of the electrical stimulation therapy, wherein each electrical pulse includes a primary phase, an interphase after the primary phase, and a passive recovery phase after the primary phase, wherein consecutive electrical pulses are separated by a standby period, and wherein the generating of the electrical pulses comprises:
operating the microcontroller in an active mode during at least one of: the primary phase and the interphase;
operating the microcontroller in a power-conservation mode during the passive recovery phase and during a substantial majority of the standby period; and
wherein the microcontroller consumes substantially less power when operating in the power-conservation mode than in the active mode.

15. The method of claim 14, wherein:
the microcontroller contains a microcontroller core and a direct memory access (DMA) unit that is separate from the microcontroller core and consumes substantially less power than the microcontroller core;
the operating of the microcontroller comprises:
turning on the microcontroller core in the active mode;
turning off the microcontroller core in the power-conservation mode; and
keeping the DMA unit turned on in the power-conservation mode.

16. The method of claim 15, wherein:
the microcontroller contains a system clock that is running at a first frequency;
the microcontroller is a part of a stimulation circuitry that further comprises an oscillator that is external to the microcontroller, the oscillator running at a second frequency that is substantially lower than the first frequency;
the operating of the microcontroller comprises driving the microcontroller with the system clock in the active mode; and
driving the DMA unit with the oscillator in the power-conservation mode.

17. The method of claim 16, further comprising:
generating an interrupt signal with a timer unit that is clocked by the oscillator; and waking up the microcontroller from the power-conservation mode via the interrupt signal immediately before a subsequent electrical pulse needs to be generated.

18. The method of claim 14, further comprising:
receiving an inductive energy;
converting the inductive energy into a direct current (DC) signal;
charging a battery with the DC signal, thereby providing a first DC voltage via the battery;
down-converting the first DC voltage to a second DC voltage smaller than the first DC voltage;
providing the second DC voltage as a voltage supply for at least the microcontroller;
up-converting the first DC voltage to a third DC voltage greater than the first DC voltage;
providing the third DC voltage as a voltage supply for a stimulation driver and an array of multiplexers coupled to the stimulation driver;
amplifying, via the stimulation driver, the electrical pulses generated by the microcontroller; and
delivering the amplified electrical pulses to the patient at least in part by configuring the array of multiplexers.

19. The method of claim 18, further comprising: disconnecting the stimulation driver from the voltage up-converter during the standby period between consecutive electrical pulses.

20. The method of claim 18, further comprising, for each pulse:
enabling the voltage up-converter and the array of multiplexers before the primary phase;
disabling the voltage up-converter and the array of multiplexers during the interphase; and
operating the microcontroller in the power-conservation mode during the passive recovery phase.

* * * * *

UNITED STATES PATENT AND TRADEMARK OFFICE
CERTIFICATE OF CORRECTION

PATENT NO. : 9,744,347 B2  
APPLICATION NO. : 14/321234  
DATED : August 29, 2017  
INVENTOR(S) : Joey Chen, Kerry Bradley and Leslie Halberg Page 1 of 1

It is certified that error appears in the above-identified patent and that said Letters Patent is hereby corrected as shown below:

Column 35, Line 63 (Claim 1, Line 9) after the word "part" delete the ","

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*